US012357355B2

(12) United States Patent
Fauth et al.

(10) Patent No.: US 12,357,355 B2
(45) Date of Patent: Jul. 15, 2025

(54) BONE FIXATION DEVICES, SYSTEMS, METHODS, AND INSTRUMENTS

(71) Applicant: RTG Scientific, LLC, Austin, TX (US)

(72) Inventors: Andrew Fauth, North Logan, UT (US); Peter Mangone, Asheville, NC (US); Bruce Hoffman, Smithfield, UT (US); Corey Johnson, Rochester, MN (US); Richard Justin Hyer, Hyrum, UT (US)

(73) Assignee: RTG Scientific, LLC, Austin, TX (US)

( * ) Notice: Subject to any disclaimer, the term of this patent is extended or adjusted under 35 U.S.C. 154(b) by 382 days.

(21) Appl. No.: 17/877,922

(22) Filed: Jul. 30, 2022

(65) Prior Publication Data
US 2023/0047553 A1    Feb. 16, 2023

Related U.S. Application Data

(60) Provisional application No. 63/231,429, filed on Aug. 10, 2021.

(51) Int. Cl.
*A61B 17/90* (2006.01)
*A61B 17/064* (2006.01)
(Continued)

(52) U.S. Cl.
CPC ...... *A61B 17/8014* (2013.01); *A61B 17/0642* (2013.01); *A61B 17/8625* (2013.01);
(Continued)

(58) Field of Classification Search
CPC .......................... A61B 17/8014; A61B 17/90
See application file for complete search history.

(56) References Cited

U.S. PATENT DOCUMENTS 3,848,276 A    11/1974  Martinez
4,810,149 A    3/1989   Lee et al.
(Continued)

FOREIGN PATENT DOCUMENTS

GB    2033755 A       5/1980
WO    2004098442 A1   11/2004
(Continued)

OTHER PUBLICATIONS

International Search Report dated Aug. 10, 2023 for corresponding PCT/US2023/020900.
(Continued)

*Primary Examiner* — Olivia C Chang
(74) *Attorney, Agent, or Firm* — David Meibos; Maywood IP Law

(57) ABSTRACT

A bone disunion instrument system may include a first bone pin, a second bone pin, and a guide block. The guide block may include first and second bone pin holes to receive the first and second bone pins, and a window intermediate the first and second bone pin holes. The first bone pin may be anchored in a first bone portion and inserted through the first bone pin hole, and the second bone pin may be anchored in a second bone portion and inserted through the second bone pin hole to impart a compression or distraction force on a bone disunion between the first and second bone portions. The window formed through the guide block may provide access for an implant placed through the window to stabilize the bone disunion while the bone disunion is placed under a compression or distraction force.

26 Claims, 26 Drawing Sheets

(51) Int. Cl.
*A61B 17/80* (2006.01)
*A61B 17/86* (2006.01)
*A61F 2/44* (2006.01)
*A61B 17/68* (2006.01)
*A61F 2/28* (2006.01)
*A61F 2/30* (2006.01)

(52) U.S. Cl.
CPC ...... *A61B 17/8635* (2013.01); *A61B 17/8695* (2013.01); *A61B 17/90* (2021.08); *A61F 2/446* (2013.01); *A61B 2017/681* (2013.01); *A61B 2017/8655* (2013.01); *A61F 2002/2835* (2013.01); *A61F 2002/30593* (2013.01); *A61F 2002/3085* (2013.01); *A61F 2002/3092* (2013.01); *A61F 2310/00011* (2013.01)

(56) References Cited

U.S. PATENT DOCUMENTS

| | | | |
|---|---|---|---|
| 5,964,768 | A | 10/1999 | Huebner |
| 6,800,078 | B2 | 10/2004 | Reed |
| 7,537,603 | B2 | 5/2009 | Huebner et al. |
| 8,337,205 | B2 | 12/2012 | Reed |
| 8,602,781 | B2 | 12/2013 | Reed |
| 8,875,399 | B2 | 11/2014 | Reed |
| 9,079,263 | B2 | 7/2015 | Reed |
| 9,526,547 | B2 | 12/2016 | Reed |
| 9,687,319 | B2 | 6/2017 | Reed |
| 9,782,209 | B2 | 10/2017 | Reed |
| 9,901,379 | B2 | 2/2018 | Reed |
| 10,085,782 | B2 | 10/2018 | Reed |
| 10,265,177 | B2 | 4/2019 | Quinn et al. |
| 10,441,385 | B2 | 10/2019 | Reed |
| 10,639,086 | B2 | 5/2020 | Reed |
| 10,687,877 | B2 | 6/2020 | Lavigne et al. |
| 2003/0088248 | A1 | 5/2003 | Reed |
| 2006/0149265 | A1 | 7/2006 | James et al. |
| 2006/0204930 | A1 | 9/2006 | Sul |
| 2007/0233123 | A1 | 10/2007 | Ahmad et al. |
| 2009/0069852 | A1 | 3/2009 | Farris et al. |
| 2009/0305189 | A1 | 12/2009 | Scortecci et al. |
| 2010/0094358 | A1 | 4/2010 | Moore et al. |
| 2010/0121327 | A1 | 5/2010 | Velikov |
| 2011/0288650 | A1 | 11/2011 | Ries et al. |
| 2013/0253517 | A1 | 9/2013 | Mitchell et al. |
| 2014/0023990 | A1 | 1/2014 | Zadeh |
| 2014/0056460 | A1 | 2/2014 | Barnes |
| 2014/0058460 | A1 | 2/2014 | Reed |
| 2014/0329202 | A1 | 11/2014 | Zadeh |
| 2015/0230843 | A1 | 8/2015 | Palmer et al. |
| 2016/0100870 | A1 | 4/2016 | Lavigne et al. |
| 2018/0303529 | A1 | 10/2018 | Zastrozna |
| 2018/0335070 | A1 | 11/2018 | May |
| 2019/0038426 | A1 | 2/2019 | Ek |
| 2019/0105131 | A1 | 4/2019 | Barton et al. |
| 2019/0223917 | A1 | 7/2019 | Gray et al. |
| 2019/0262047 | A1 | 8/2019 | Sommers et al. |
| 2019/0358039 | A1 | 11/2019 | Ducharme et al. |
| 2021/0113249 | A1* | 4/2021 | Shoemaker ............ A61L 31/06 |
| 2021/0259842 | A1 | 8/2021 | Feng et al. |
| 2022/0249148 | A1 | 8/2022 | Hyer et al. |

FOREIGN PATENT DOCUMENTS

| | | |
|---|---|---|
| WO | 2007074498 B1 | 1/2008 |
| WO | 2019238085 A1 | 12/2019 |
| WO | 2020224657 A1 | 11/2020 |

OTHER PUBLICATIONS

International Search Report dated Jul. 5, 2023 for corresponding PCT/US2023/018561.
International Search Report dated Jan. 9, 2023 for corresponding PCT Application No. PCT/US2022/038975.
U.S. Appl. No. 10/085,782, filed Oct. 2, 2018, Reed.
Supplementary European Search Report mailed Dec. 23, 2024 for corresponding European Patent Application No. 22753293.4.

* cited by examiner

BONE FIXATION DEVICES, SYSTEMS, METHODS, AND INSTRUMENTS

CROSS-REFERENCE TO RELATED APPLICATIONS

This application claims the benefit of U.S. Provisional Patent Application Ser. No. 63/231,429 filed on Aug. 10, 2021, entitled "BONE FIXATION DEVICES, SYSTEMS, METHODS, AND INSTRUMENTS." The foregoing document is hereby incorporated by reference in its entirety.

TECHNICAL FIELD

The present disclosure relates to bone fixation devices, systems, methods, and instruments. More specifically, the present disclosure relates to bone fixation devices, systems, methods, and instruments for stabilizing disunions between two or more adjacent bones or bone portions, such as bone joints, bone fractures, bone abutments, etc.

BACKGROUND

Surgical procedures involving fasteners implanted in bone to correct a disunion between one or more bone portions can become loose over time due to multi-axial forces and off-axis loading scenarios that may be applied to the fastener during the healing/fusion process. Traditional bone fastener thread designs may not provide sufficient fixation to overcome these multi-axial forces and off-axis loading scenarios.

Accordingly, bone fixation fasteners with improved thread and compression designs for increasing bone fixation and load sharing between a bone/fastener interface experiencing multi-axial and off-loading conditions would be desirable.

SUMMARY

The various bone fixation devices, systems, and methods of the present disclosure have been developed in response to the present state of the art, and in particular, in response to the problems and needs in the art that have not yet been fully solved by currently available bone fixation devices, systems, and methods. In some embodiments, the bone fixation devices, systems, and methods of the present disclosure may provide improved bone fixation and load sharing between a bone/fastener interface under multi-axial and off-loading conditions.

In some embodiments, a bone disunion instrument system may include a first bone pin having a first proximal end and a first distal end configured to anchor in a first bone portion, a second bone pin having a second proximal end and a second distal end configured to anchor in a second bone portion, and a guide block. The second bone portion may be positioned adjacent the first bone portion and a bone disunion may be formed intermediate the first bone portion and the second bone portion. The guide block may include a first bone pin hole configured to receive the first bone pin therethrough, a second bone pin hole configured to receive the second bone pin therethrough, and a window formed through the guide block intermediate the first bone pin hole and the second bone pin hole. The first bone pin may be anchored in the first bone portion and inserted through the first bone pin hole, and the second bone pin may be anchored in the second bone portion and inserted through the second bone pin hole. The first bone pin hole may impart a first force on the first bone pin along a first direction to compress or distract the first bone portion with respect to the second bone portion. The second bone pin hole may impart a second force on the second bone pin along a second direction to compress or distract the second bone portion with respect to the first bone portion. The window may be configured to provide access for an implant placed through the window to stabilize the bone disunion during compression or distraction of the bone disunion.

In some embodiments, the guide block may include at least one of: a first inferior lead-in feature formed about the first bone pin hole on an inferior surface of the guide block; a second inferior lead-in feature formed about the second bone pin hole on the inferior surface of the guide block; a first superior lead-in feature formed about the first bone pin hole on a superior surface of the guide block; and a second superior lead-in feature formed about the second bone pin hole on the superior surface of the guide block.

In some embodiments, a first longitudinal axis of the first bone pin hole may be parallel with a second longitudinal axis of the second bone pin hole.

In some embodiments, the first bone pin hole and the second bone pin hole may be separated from each other by a first distance to compress the first bone portion and the second bone portion toward each other when the first bone pin is anchored in the first bone portion and inserted through the first bone pin hole, and the second bone pin is anchored in the second bone portion and inserted through the second bone pin hole.

In some embodiments, the first bone pin hole and the second bone pin hole may be separated from each other by a second distance to distract the first bone portion and the second bone portion away from each other when the first bone pin is anchored in the first bone portion and inserted through the first bone pin hole, and the second bone pin is anchored in the second bone portion and inserted through the second bone pin hole.

In some embodiments, the first bone pin hole and the second bone pin hole may be separated from each other by a third distance to hold the first bone portion and the second bone portion in a neutral position with respect to each other when the first bone pin is anchored in the first bone portion and inserted through the first bone pin hole, and the second bone pin is anchored in the second bone portion and inserted through the second bone pin hole.

In some embodiments, the bone disunion instrument system may also include an insert guide and a spade guide. The insert guide may be configured to be at least partially received within the window, and the insert guide may include a guide hole formed therethrough. The spade guide may include a spade portion at a distal end of the spade guide and a pin portion at a proximal end of the spade guide. The insert guide may be at least partially receivable within the window, the spade portion may be inserted into the bone disunion between the first bone portion and the second bone portion, and the pin portion may be inserted through the guide hole. The first bone pin hole may be configured to guide the first bone pin into the first bone portion along a first trajectory defined by an orientation of the pin portion relative to the guide hole, and the second bone pin hole may be configured to guide the second bone pin into the second bone portion along a second trajectory defined by the orientation of the pin portion relative to the guide hole.

In some embodiments, a bone disunion instrument system may include a first bone pin having a first proximal end and a first distal end configured to anchor in a first bone portion, a second bone pin having a second proximal end and a second distal end configured to anchor in a second bone portion, a spade guide, a placement block, and an implant insertion block. The second bone portion may be positioned adjacent the first bone portion and a bone disunion may be formed intermediate the first bone portion and the second bone portion. The spade guide may include a spade portion at a distal end of the spade guide, and a pin portion at a proximal end of the spade guide. The placement block may include a first bone pin hole configured to receive the first bone pin therethrough, a second bone pin hole configured to receive the second bone pin therethrough, and a placement block hole intermediate the first bone pin hole and the second bone pin hole. The spade portion of the spade guide may be inserted into the bone disunion between the first bone portion and the second bone portion, and the pin portion of the spade guide may be inserted through the placement block hole. The first bone pin hole may be configured to guide the first bone pin into the first bone portion along a first trajectory defined by an orientation of the pin portion relative to the placement block hole, and the second bone pin hole may be configured to guide the second bone pin into the second bone portion along a second trajectory defined by the orientation of the pin portion relative to the placement block hole. The implant insertion block may include a third bone pin hole, a fourth bone pin hole, and a window formed through the implant insertion block intermediate the third bone pin hole and the fourth bone pin hole. The first bone pin may be anchored in the first bone portion and inserted through the third bone pin hole, and the second bone pin may be anchored in the second bone portion and inserted through the fourth bone pin hole. The window may be configured to provide access for an implant placed through the window to stabilize the bone disunion.

In some embodiments, the placement block may include at least one of: a first inferior lead-in feature formed about the first bone pin hole on an inferior surface of the placement block; a second inferior lead-in feature formed about the second bone pin hole on the inferior surface of the placement block; a first superior lead-in feature formed about the first bone pin hole on a superior surface of the placement block; and a second superior lead-in feature formed about the second bone pin hole on the superior surface of the placement block.

In some embodiments, a first longitudinal axis of the first bone pin hole may be parallel with a second longitudinal axis of the second bone pin hole.

In some embodiments, the spade portion may include a first substantially flat surface and a second substantially flat surface opposite the first substantially flat surface. The first substantially flat surface may be configured to engage a first surface of the first bone portion within the bone disunion, and the second substantially flat surface may be configured to engage a second surface of the second bone portion within the bone disunion to indicate an orientation of the bone disunion with the pin portion of the spade guide.

In some embodiments, the implant insertion block may include at least one of: a first inferior lead-in feature formed about the first bone pin hole on an inferior surface of the implant insertion block; a second inferior lead-in feature formed about the second bone pin hole on the inferior surface of the implant insertion block; a first superior lead-in feature formed about the first bone pin hole on a superior surface of the implant insertion block; and a second superior lead-in feature formed about the second bone pin hole on the superior surface of the implant insertion block.

In some embodiments, the third bone pin hole may be parallel with the fourth bone pin hole.

In some embodiments, the first bone pin hole and the second bone pin hole may be separated from each other by a first distance to compress the first bone portion and the second bone portion toward each other when the first bone pin is anchored in the first bone portion and inserted through the first bone pin hole, and the second bone pin is anchored in the second bone portion and inserted through the second bone pin hole.

In some embodiments, a method of stabilizing a bone disunion intermediate a first bone portion and a second bone portion may include compressing or distracting the bone disunion and inserting an implant into the bone disunion through a window formed in the guide block to stabilize the bone disunion during compression or distraction of the bone disunion, compressing or distracting the bone disunion may include inserting a proximal end of a first bone pin into a first bone pin hole of a guide block to impart a first force on the first bone pin along a first direction to compress or distract the first bone portion with respect to the second bone portion, and inserting a proximal end of a second bone pin into a second bone pin hole of the guide block to impart a second force on the second bone pin along a second direction to compress or distract the second bone portion with respect to the first bone portion.

In some embodiments, the method may also include inserting a spade portion of a spade guide into the bone disunion, engaging a first surface of the first bone portion with a first substantially flat surface of the spade portion, and engaging a second surface of the second bone portion with a second substantially flat surface of the spade portion. A pin portion of the spade guide may extend away from the bone disunion to indicate an orientation of the bone disunion relative to the first bone portion and the second bone portion.

In some embodiments, the method may also include positioning the first bone pin relative to the orientation of the bone disunion by inserting a distal end of the first bone pin into the first bone pin hole of the guide block and anchoring the distal end of the first bone pin into the first bone portion while the pin portion of the spade guide extends through a window formed in the guide block. The method may also include positioning the second bone pin relative to the orientation of the bone disunion by inserting a distal end of the second bone pin into the second bone pin hole of the guide block and anchoring the distal end of the second bone pin into the second bone portion while the pin portion of the spade guide extends through the window formed in the guide block.

In some embodiments, the guide block may comprise a first guide block, and compressing the bone disunion may include inserting the proximal end of the first bone pin into the first bone pin hole of the first guide block to impart the first force on the first bone pin along the first direction to compress the first bone portion with respect to the second bone portion, and inserting the proximal end of the second bone pin into the second bone pin hole of the first guide block to impart the second force on the second bone pin along the second direction to compress the second bone portion with respect to the first bone portion.

In some embodiments, the guide block may comprise a second guide block, and distracting the bone disunion may include inserting the proximal end of the first bone pin into the first bone pin hole of the second guide block to impart the first force on the first bone pin along the first direction to distract the first bone portion with respect to the second bone portion, and inserting the proximal end of the second bone pin into the second bone pin hole of the second guide block to impart the second force on the second bone pin along the second direction to compress the second bone portion with respect to the first bone portion.

In some embodiments, compressing the bone disunion may include rotating the guide block to a first position and inserting the proximal end of the second bone pin into a converging pin hole of the guide block to impart a compression force on the bone disunion, and distracting the bone disunion may include rotating the guide block to a second position and inserting the proximal end of the second bone pin into a diverging bone pin hole of the guide block to impart a distraction force on the bone disunion.

These and other features and advantages of the present disclosure will become more fully apparent from the following description and appended claims or may be learned by the practice of the bone fixation devices, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which.

Figure 1A:
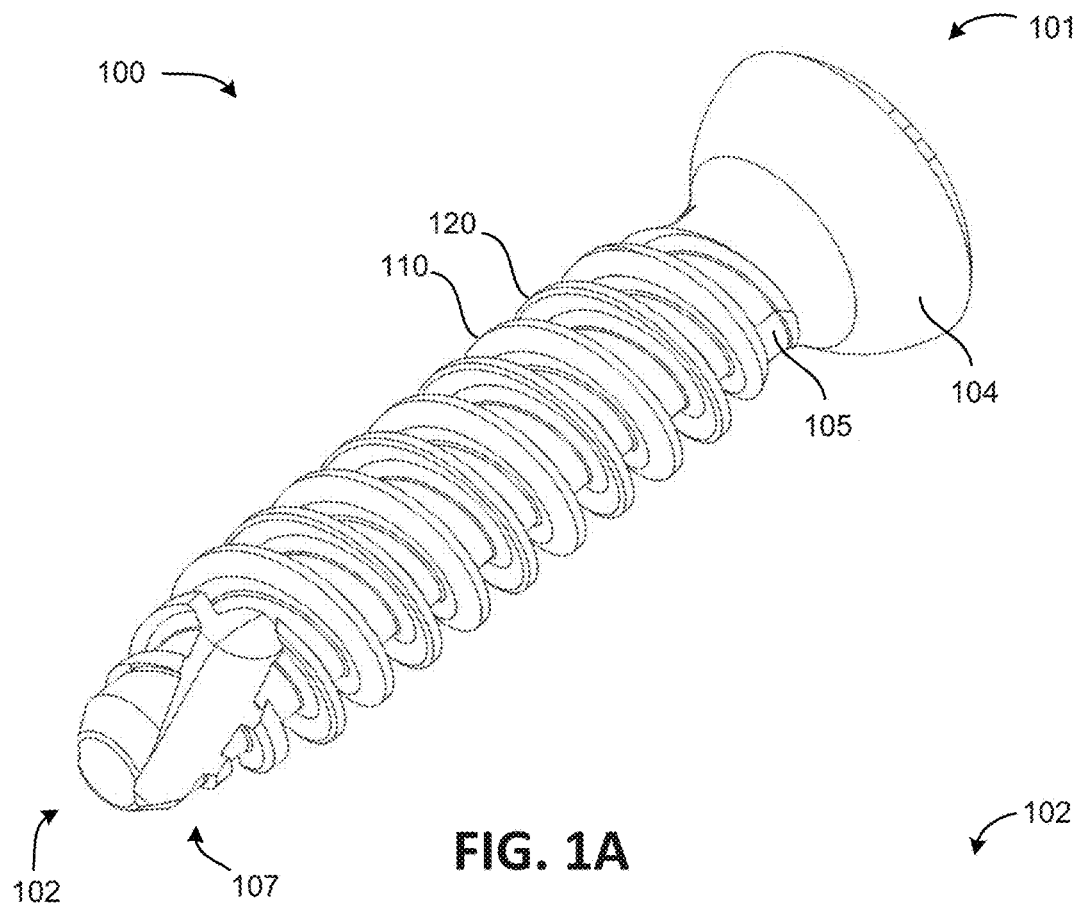
FIG. 1A illustrates a front perspective view of a fastener, according to an embodiment of the present disclosure.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the devices, systems, and methods, as represented in the drawings, is not intended to limit the scope of the present disclosure but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. *Varus* means deviation of the distal part of the leg below the knee inward, resulting in a bowlegged appearance. Valgus means deviation of the distal part of the leg below the knee outward, resulting in a knock-kneed appearance.

Figure 1B:
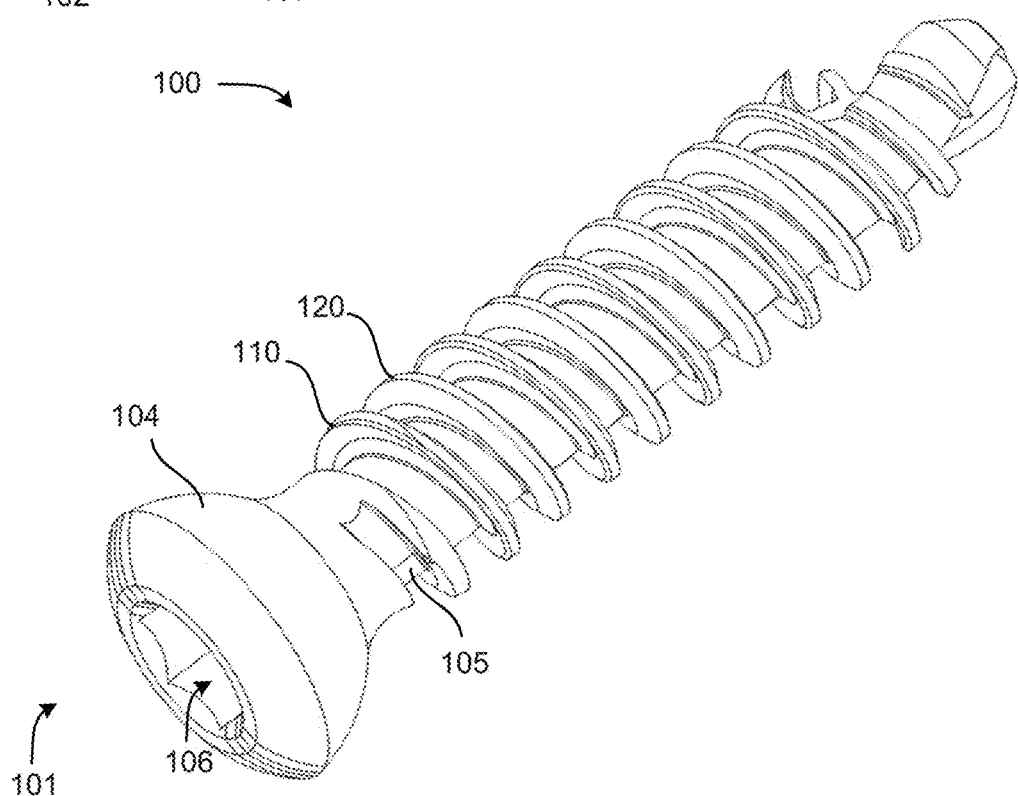
FIG. 1B illustrates a rear perspective view of the fastener of FIG. 1A.
Figure 1C:
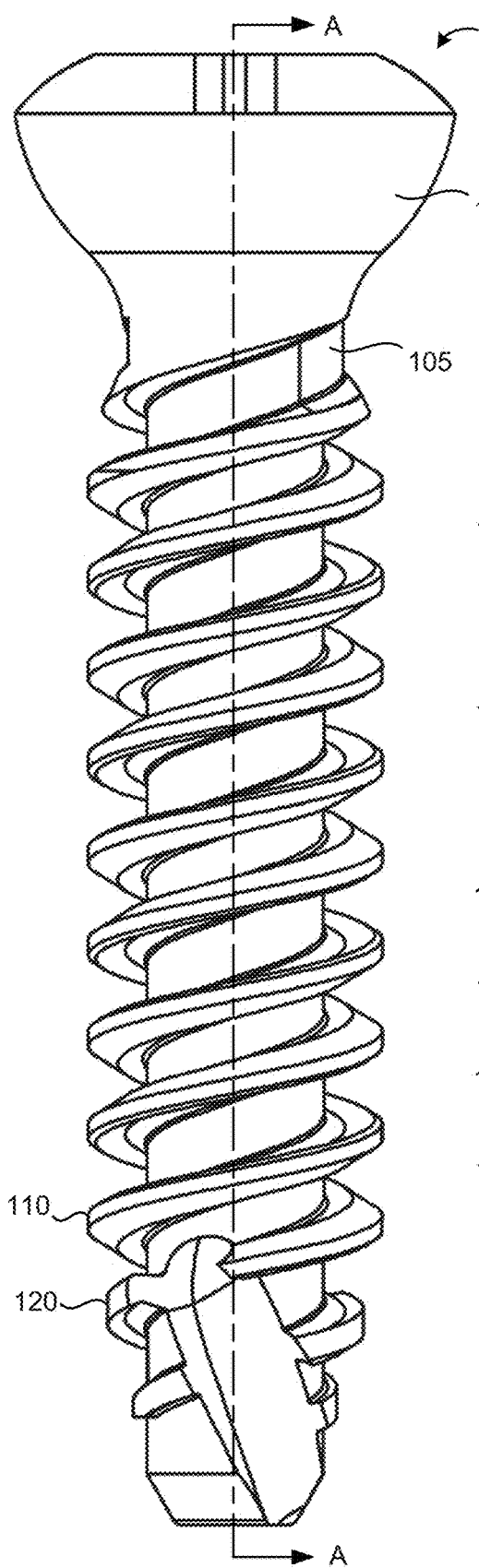
FIG. 1C illustrates a side view of the fastener of FIG. 1A.
Figure 1D:
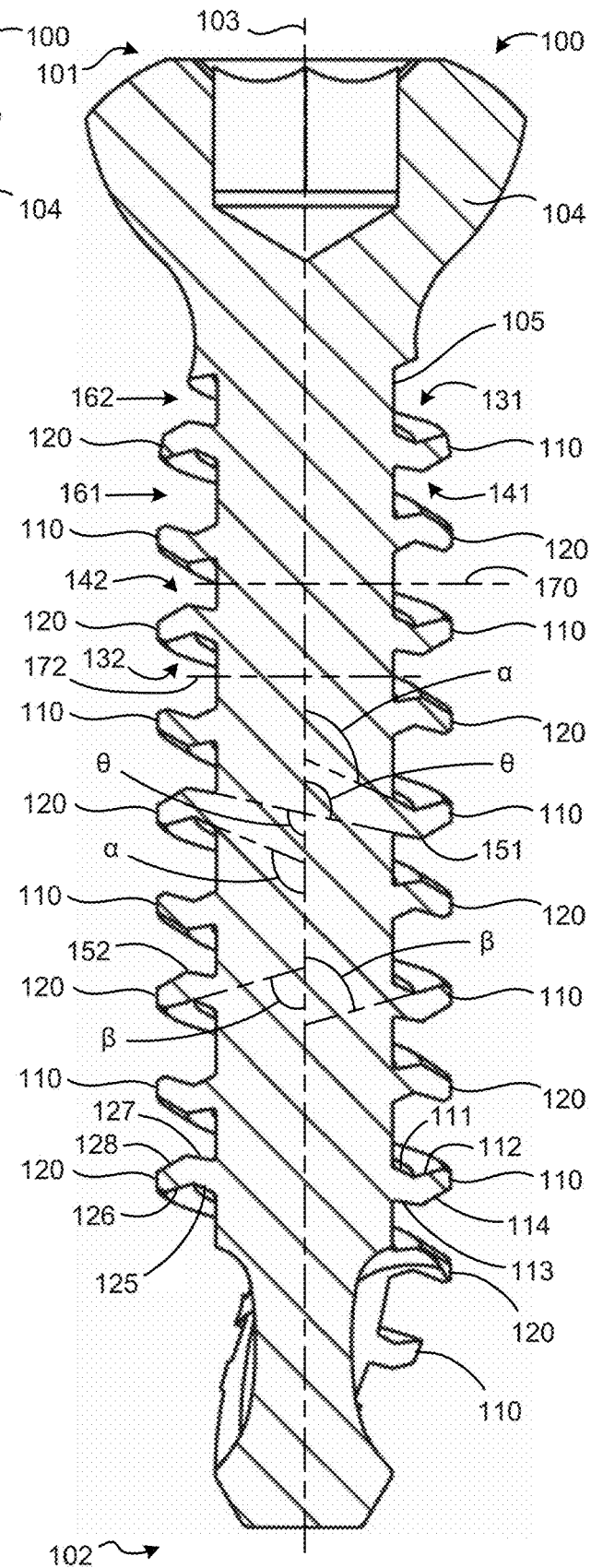
FIG. 1D illustrates a cross-sectional side view of the fastener of FIG. 1C, taken along the line A-A.

FIGS. 1A-1D illustrate various views of a bone screw, bone implant, implantable bone anchor, bone disunion fastener, or fastener 100, according to an example of the present disclosure. Specifically, FIG. 1A is a front perspective view of the fastener 100, FIG. 1B is a rear perspective view of the fastener 100, FIG. 1C is a side view of the fastener 100, and FIG. 1D is a cross-sectional side view of the fastener 100 taken along the line A-A in FIG. 1C.

In general, the fastener 100 may include a shaft 105 having a proximal end 101, a distal end 102, and a longitudinal axis 103. The fastener 100 may also include a head 104 located at the proximal end 101 of the shaft 105, a torque connection interface 106 formed in/on the head 104 (in either a male/female configuration), and a self-tapping feature 107 formed in the distal end 102 of the shaft 105.

In some embodiments, the fastener 100 may include a first helical thread 110 disposed about the shaft 105, and a second helical thread 120 disposed about the shaft 105 adjacent the first helical thread 110.

In some embodiments, the fastener 100 may include a "dual start" or "dual lead" thread configuration comprising the first helical thread 110 and the second helical thread 120.

In some embodiments, a depth of the first helical thread 110 and/or the second helical thread 120 with respect to the shaft 105 may define a major diameter vs. a minor diameter of the shaft 105 alone.

In some embodiments, a major diameter and/or a minor diameter of the fastener 100 may be constant or substantially constant along the entire length of the fastener, or along a majority of the length of the fastener. In these embodiments, a constant minor diameter may help avoid blowout of narrow/delicate bones (e.g., a pedicle) when inserting a fastener into a bone. In some embodiments, a pilot hole may first be drilled into a narrow/delicate bone and then a fastener having a similar minor diameter in comparison to the diameter of the pilot hole may be chosen to avoid blowout when inserting the fastener into the bone, as will be discussed in more detail below.

In some embodiments, a depth of the first helical thread 110 and/or the second helical thread 120 with respect to the shaft 105 may vary along a length of the shaft 105 to define one or more major diameters of the fastener 100 and/or one or more regions along the fastener 100 may comprise one or more continuously variable major diameters.

In some embodiments, a thickness of the shaft 105 may vary along a length of the shaft 105 to define one or more minor diameters of the fastener 100, and/or one or more regions along the fastener 100 may comprise one or more continuously variable minor diameters.

In some embodiments, a thickness/height/width/length/pitch/angle/shape, etc., of the first helical thread 110 and/or the second helical thread 120 (or any additional helical thread) may vary along a length of the shaft 105. For example, a thickness/height/width/length/pitch/angle/shape, etc., of the first helical thread 110 and/or the second helical thread 120 may be greater towards the tip of the fastener and thinner towards the head of the fastener (or vice versa) in either a discrete or continuously variable fashion, etc.

In some embodiments, the major and/or minor diameters may increase toward a proximal end or head of a fastener in order to increase bone compaction as the fastener is terminally inserted into the bone/tissue.

In some embodiments, a pitch of the first helical thread 110 and/or the second helical thread 120 may vary along a length of the fastener 100.

In some embodiments, the fastener 100 may include a plurality of helical threads disposed about the shaft 105. However, it will also be understood that any of the fasteners disclosed or contemplated herein may include a single helical thread disposed about the shaft of the fastener. Moreover, the fastener 100 may comprise a nested plurality of helical threads having different lengths (not shown). As one non-limiting example, the fastener 100 may include a first helical thread 110 that is longer than a second helical thread 120, such that the fastener 100 comprises dual threading along a first portion of the shaft 105 and single threading along a second portion of the shaft 105.

In some embodiments, the plurality of helical threads may include three helical threads comprising a "triple start" or "triple lead" thread configuration (not shown).

In some embodiments, the plurality of helical threads may include four helical threads comprising a "quadruple start" or "quadruple lead" thread configuration (not shown).

In some embodiments, the plurality of helical threads may include more than four helical threads (not shown).

In some embodiments, the fastener 100 may include first threading with any of the shapes disclosed herein oriented toward one of the proximal end and the distal end of the fastener 100, with the first threading located proximate the distal end of the fastener 100, as well as second threading with any of the shapes disclosed herein oriented toward the other one of the proximal end and the distal end of the fastener 100, with the second threading located proximate the head of the fastener 100 (not shown).

In some embodiments, the fastener 100 may include multiple threading (e.g., dual helical threading, etc.) with any of the shapes disclosed herein located proximate one of the proximal end and the distal end of the fastener 100, as well as single threading with any of the shapes disclosed herein with the second threading located proximate the other of the proximal end and the distal end of the fastener 100.

In some embodiments, the first helical thread 110 may include a plurality of first concave undercut surfaces 131 and a plurality of first convex undercut surfaces 141.

In some embodiments, the second helical thread 120 may include a plurality of second concave undercut surfaces 132 and a plurality of second convex undercut surfaces 142.

In some embodiments, when the fastener 100 is viewed in section along a plane that intersects the longitudinal axis 103 of the shaft 105 (e.g., see FIG. 1D), the plurality of first concave undercut surfaces 131 and the plurality of second convex undercut surfaces 142 may be oriented toward (i.e., point toward) the proximal end 101 of the shaft 105.

In some embodiments, the plurality of first convex undercut surfaces 141 and the plurality of second concave undercut surfaces 132 may be oriented toward (i.e., point toward) the distal end 102 of the shaft 105.

In some embodiments, at least one of the plurality of first concave undercut surfaces 131, the plurality of first convex undercut surfaces 141, the plurality of second concave undercut surfaces 132, and the plurality of second convex undercut surfaces 142 may comprise at least one substantially flat surface.

In some embodiments, when the fastener 100 is viewed in section along a plane intersecting the longitudinal axis 103 of the shaft 105, the first helical thread 110 may comprise a plurality of first bent shapes (comprising at least one surface that is angled relative to the longitudinal axis 103 of the shaft 105 and/or at least one undercut surface) with a plurality of first intermediate portions 151 that are oriented toward (i.e., point toward) the distal end 102 of the shaft 105. This may be referred to as "standard" threading, having a "standard" orientation.

In some embodiments, when the fastener 100 is viewed in section along a plane intersecting the longitudinal axis 103 of the shaft 105, the second helical thread 120 may comprise a plurality of second bent shapes (comprising at least one surface that is angled relative to the longitudinal axis 103 of the shaft 105 and/or at least one undercut surface) with a plurality of second intermediate portions 152 that are oriented toward (i.e., point toward) the proximal end 101 of the shaft 105. This may be referred to as "inverted" threading, having an "inverted" orientation.

In some embodiments, one or more helical threads may morph/transition between a standard orientation and an inverted orientation along a shaft of a fastener.

In some embodiments, at least one of the plurality of first concave undercut surfaces 131, the plurality of first convex undercut surfaces 141, the plurality of second concave undercut surfaces 132, and the plurality of second convex undercut surfaces 142 may comprise at least one curved surface.

As shown in FIG. 1D, the proximally-oriented and distally-oriented surfaces of the first helical thread 110 (i.e., the first concave undercut surfaces 131 and the first convex undercut surfaces 141 in the fastener 100 of FIG. 1D) may not have mirror symmetry relative to each other about any plane perpendicular to the longitudinal axis 103 of the fastener 100. Rather, the first concave undercut surfaces 131 and the first convex undercut surfaces 141 may be generally parallel to each other. The same may be true for the second helical thread 120, in which the second concave undercut surfaces 132 and the second convex undercut surfaces 142 may not have mirror symmetry relative to each other but may be generally parallel to each other.

Conversely, as also shown in FIG. 1D, the proximally-oriented surfaces of the first helical thread 110 may have mirror symmetry relative to the distally-oriented surfaces of the second helical thread 120. Specifically, the first concave undercut surfaces 131 may have mirror symmetry relative to the second convex undercut surfaces 142 about a plane 170 that bisects the space between them and lies perpendicular to the longitudinal axis 103.

Similarly, the distally-oriented surfaces of the first helical thread 110 may have mirror symmetry relative to the proximally-oriented surfaces of the second helical thread 120. Specifically, the second concave undercut surfaces 132 may have mirror symmetry relative to the first convex undercut surfaces 141 about a plane 172 that bisects the space between them and lies perpendicular to the longitudinal axis 103.

This mirror symmetry may be present along most of the length of the first helical thread 110 and the second helical thread 120, with symmetry across different planes arranged between adjacent turns of the first helical thread 110 and the second helical thread 120 along the length of the longitudinal axis 103. Such mirror symmetry may help more effectively capture bone between the first helical thread 110 and the second helical thread 120 and may also facilitate manufacture of the fastener 100.

Figure 2:
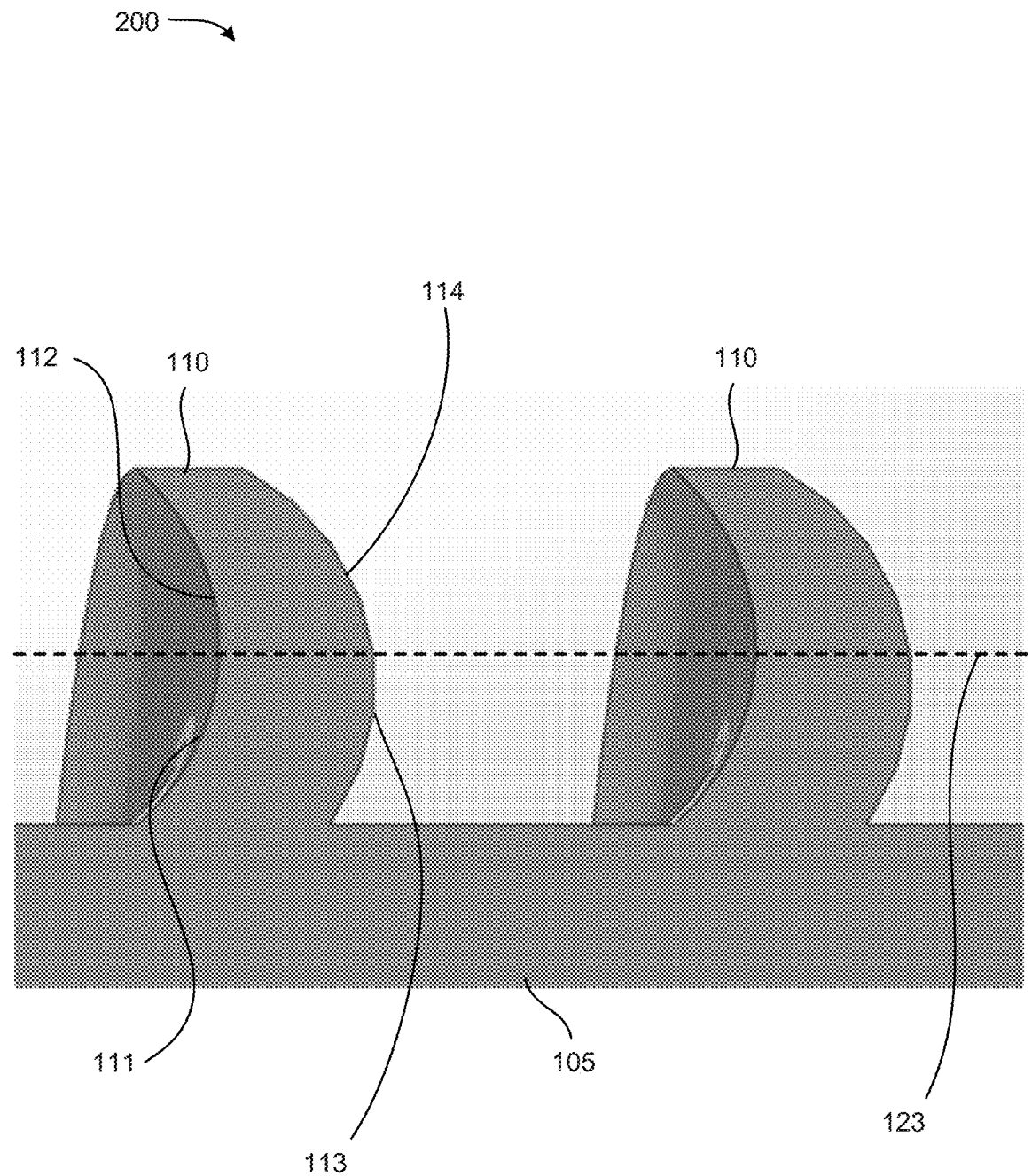
FIG. 2 illustrates a partial cross-sectional side view of a fastener comprising crescent-shaped threading, according to an embodiment of the present disclosure.

In some embodiments, when the fastener 100 is viewed in section along a plane intersecting the longitudinal axis 103 of the shaft 105, the first helical thread 110 may include at least one partial crescent shape that is oriented toward (i.e., points toward) the distal end 102 of the shaft 105 and/or the proximal end 101 of the shaft 105. FIG. 2 illustrates a partial cross-sectional view of a fastener 200 comprising crescent shapes, as one non-limiting example of such an embodiment.

In some embodiments (not shown), when the fastener 100 is viewed in section along a plane intersecting the longitudinal axis 103 of the shaft 105, the first helical thread 110 may include at least one partial crescent shape that is oriented toward (i.e., points toward) the distal end 102 of the shaft 105, and the second helical thread 120 may include at least one partial crescent shape that is oriented toward (i.e., points toward) the proximal end 101 of the shaft 105.

In some embodiments (not shown), the first helical thread 110 may include a first plurality of partial crescent shapes that are oriented toward (i.e., point toward) the distal end 102 of the shaft 105, and the second helical thread 120 may include a second plurality of partial crescent shapes that are oriented toward (i.e., point toward) the proximal end 101 of the shaft 105.

In some embodiments (not shown), the first plurality of partial crescent shapes and the second plurality of partial crescent shapes may be arranged in alternating succession along the shaft 105 of the fastener 100.

In some embodiments, the first helical thread 110 may be bisected by the line 123 shown in FIG. 2 with each crescent shape including a plurality of first undercut surfaces 111, a plurality of second undercut surfaces 112, a plurality of third undercut surfaces 113, and a plurality of fourth open surfaces 114 similar to the helical threading shown in FIG. 1D, except with curved surfaces in place of flat surfaces.

In some embodiments, the plurality of first undercut surfaces 111 and the plurality of second undercut surfaces 112 may comprise concave curved surfaces. However, it will be understood that portions of the plurality of first undercut surfaces 111 and/or portions of the plurality of second undercut surfaces 112 may also comprise convex curved surfaces and/or flat surfaces (not shown in FIG. 2).

In some embodiments, the plurality of third undercut surfaces 113 and the plurality of fourth open surfaces 114 may comprise convex curved surfaces. However, it will be understood that portions of the plurality of third undercut surfaces 113 and the plurality of fourth open surfaces 114 may also comprise concave curved surfaces and/or flat surfaces (not shown in FIG. 2).

In some embodiments, the plurality of third undercut surfaces 113 and the plurality of fourth open surfaces 114 may be replaced by a ramped surface (such as that utilized in a standard buttress thread design) without any undercuts (not shown in FIG. 2). Likewise, any of the other thread designs disclosed herein may utilize a ramped or buttress thread design on at least one side of the helical thread.

In some embodiments, a fastener may have only standard threads or only inverted threads. The type of threads that are desired may depend on the type and/or magnitude of loads to be applied to the fastener. For example, a screw loaded axially away from the bone in which it is implanted may advantageously have a standard thread, while a screw loaded axially toward the bone in which it is implanted may advantageously have an inverted thread. A screw that may experience multi-axial loading and/or off-loading conditions may advantageously include at least one standard thread and at least one inverted thread in order to increase bone fixation and load sharing between a bone/fastener interface during multi-axial and off-loading conditions to reduce high bone strain and distribute multi-axial forces applied to the bone in a load-sharing, rather than load-bearing, configuration. Shear loads and/or bending moments may also be optimally resisted with any chosen combination of threading, threading morphology, and/or threading variations contemplated herein to optimally resist shear loads, bending moments, multi-axial loading, off-loading conditions, etc.

In some embodiments, fasteners with standard threads may be used in conjunction with fasteners with inverted threads in order to accommodate different loading patterns.

In some embodiments, a single fastener may have both standard and inverted threads, like the fastener 100. Such a combination of threads may help the fastener 100 remain in place with unknown and/or varying loading patterns.

In some embodiments, the geometry of the threading of a fastener (with standard and/or inverted threads) may be varied to suit the fastener for a particular loading scheme. For example, the number of threads, the number of thread starts, the pitch of the threading, the lead(s) of the threading, the shape(s) of the threading, any dimension(s) associated with the threading (e.g., any length(s)/width(s)/height(s)/inflection point(s), etc., associated with the threading), the major diameter(s), the minor diameter(s), any angulation/angles associated with any surfaces of the threading, the "handedness" of the threading (e.g., right-handed vs. left-handed), etc., may be varied accordingly to suit any specific medium of installation, loading pattern, desired radial loading force, pull-out strength, application, procedure, etc., that may be involved.

In some embodiments, the material(s) of any portion of a bone implant, joint replacement implant, fastener, bone disunion fastener, etc., described herein may include, but are not limited to: metals (e.g., titanium, cobalt, stainless steel, etc.), metal alloys, plastics, polymers, ceramics, PEEK, UHMWPE, composites, additive particles, textured surfaces, biologics, biomaterials, bone, etc.

In some embodiments, any of the fasteners or implants described herein may include additional features such as: self-tapping features, locking features (e.g., locking threading formed on a portion of the fastener, such as threading located on or near a head of the fastener), opening(s), cannulation(s), fenestration(s), any style of fastener head (or no fastener head at all), any style of torque connection interface (or no torque connection interface at all), etc.

In some embodiments, the opening(s), cannulation(s), fenestration(s), etc., formed in any of the fasteners or implants described herein may be configured to receive any suitable bone cement or bone augment material therein to facilitate bone in-growth, bone fusion, etc.

In some embodiments, a tap (not shown) may be utilized to pre-form threading in a bone or bone augment material according to any threading shape that is disclosed or contemplated herein. In this manner, taps with any suitable shape may be utilized in conjunction with any fastener described or contemplated herein to match or substantially match the threading geometry of a given fastener or bone implant.

In some embodiments, a minor diameter of the fastener may be selected to match, or substantially match, a diameter of a pilot hole that is formed in a bone to avoid bone blowout when the fastener is inserted into the pilot hole.

Additionally, or alternatively thereto, the type of threads and/or thread geometry may be varied based on the type of bone in which the fastener is to be anchored. For example, fasteners anchored in osteoporotic bone may fare better with standard or inverted threads, or when the pitch, major diameter, and/or minor diameter are increased or decreased, or when the angulation of thread surfaces is adjusted, etc.

In some embodiments, a surgical kit may include multiple fasteners/implants with any of the different fasteners/implants and thread options described or contemplated herein. The surgeon may select the appropriate fasteners/implants from the kit based on the particular loads to be applied and/or the quality of bone in which the fastener/implants are to be anchored.

Continuing with FIG. 1D, in some embodiments the first helical thread 110 may include a plurality of first undercut surfaces 111, a plurality of second undercut surfaces 112, a plurality of third undercut surfaces 113, and a plurality of fourth open surfaces 114.

In some embodiments, the second helical thread 120 may include a plurality of fifth undercut surfaces 125, a plurality of sixth undercut surfaces 126, a plurality of seventh undercut surfaces 127, and a plurality of eighth open surfaces 128.

In some embodiments, one or more of the plurality of first undercut surfaces 111, the plurality of second undercut surfaces 112, the plurality of third undercut surfaces 113, the plurality of fourth open surfaces 114, the plurality of fifth undercut surfaces 125, the plurality of sixth undercut surfaces 126, the plurality of seventh undercut surfaces 127, and the plurality of eighth open surfaces 128 may comprise at least one flat or substantially flat surface.

In some embodiments, the plurality of first undercut surfaces 111, the plurality of third undercut surfaces 113, the plurality of sixth undercut surfaces 126, and the plurality of eighth open surfaces 128 may be angled towards the distal end 102 of the shaft 105.

In some embodiments, the plurality of second undercut surfaces 112, the plurality of fourth open surfaces 114, the plurality of fifth undercut surfaces 125, and the plurality of seventh undercut surfaces 127 may be angled towards the proximal end 101 of the shaft 105.

In some embodiments, when the fastener 100 is viewed in section along a plane that intersects the longitudinal axis 103 of the shaft 105 (as shown in FIG. 1D), the first helical thread 110 may include at least one chevron shape that is oriented toward (i.e., points toward) the distal end 102 of the shaft 105. Likewise, the second helical thread 120 may also include at least one chevron shape that is oriented toward (i.e., points toward) the proximal end 101 of the shaft 105.

In some embodiments, when the fastener 100 is viewed in section along a plane that intersects the longitudinal axis 103 of the shaft 105 (as shown in FIG. 1D), the first helical thread 110 may include a first plurality of chevron shapes that are oriented toward (i.e., point toward) the distal end 102 of the shaft 105. Likewise, the second helical thread 120 may include a second plurality of chevron shapes that are oriented toward (i.e., point toward) the proximal end 101 of the shaft 105.

In some embodiments, the first plurality of chevron shapes and the second plurality of chevron shapes may be arranged in alternating succession along the shaft 105 of the fastener 100, (e.g., see FIG. 1D).

In some embodiments, a plurality of first interlocking spaces 161 and a plurality of second interlocking spaces 162 may be formed between the first helical thread 110 and the second helical thread 120 along the shaft 105 of the fastener 100.

In some embodiments, the plurality of first interlocking spaces 161 may be formed intermediate the first concave undercut surfaces 131 and the second concave undercut surfaces 132.

In some embodiments, the plurality of second interlocking spaces 162 may be formed intermediate the first convex undercut surfaces 141 and the second convex undercut surfaces 142.

In some embodiments, the plurality of first interlocking spaces 161 may be larger in size than the plurality of second interlocking spaces.

In some embodiments, the plurality of first interlocking spaces 161 and the plurality of second interlocking spaces 162 may be shaped and/or configured to interlock with bone/other tissues received therein to increase fixation of the fastener 100 within the bone/other tissues and provide additional resistance against multi-axial forces that may be applied to the fastener 100 and/or the bone/other tissues.

In some embodiments, the plurality of second undercut surfaces 112 and the plurality of sixth undercut surfaces 126 may be angled toward each other to trap bone/bone augment material within the plurality of first interlocking spaces 161 in order to increase fixation and resistance against multi-axial forces.

In some embodiments, the plurality of third undercut surfaces 113 and the plurality of seventh undercut surfaces 127 may be angled toward each other to trap bone/other tissues within the plurality of second interlocking spaces 162 in order to increase fixation and resistance against multi-axial forces.

In some embodiments, the plurality of first undercut surfaces 111 and the plurality of fifth undercut surfaces 125 may each form an angle α with respect to the longitudinal axis 103 of the shaft 105, as shown in FIG. 1D.

In some embodiments, the angle α may be greater than 90 degrees.

In some embodiments, the plurality of second undercut surfaces 112 and the plurality of sixth undercut surfaces 126 may each form an angle β with respect to the longitudinal axis 103 of the shaft 105.

In some embodiments, the angle θ may be less than 90 degrees.

In some embodiments, the plurality of third undercut surfaces 113 and the plurality of seventh undercut surfaces 127 may each form an angle θ with respect to the longitudinal axis 103 of the shaft 105.

In some embodiments, the angle θ may be approximately 90 degrees.

In some embodiments, the angle θ may be greater than 90 degrees.

It will be understood that any fastener/implant described or contemplated herein may include any thread configuration, feature, or morphology described or contemplated herein to achieve optimal fixation within a given bone/tissue. Moreover, it will also be understood that any fastener/implant described or contemplated herein may be utilized in conjunction with (or within) any system, method, or instrumentation described or contemplated herein.

Figure 3A:
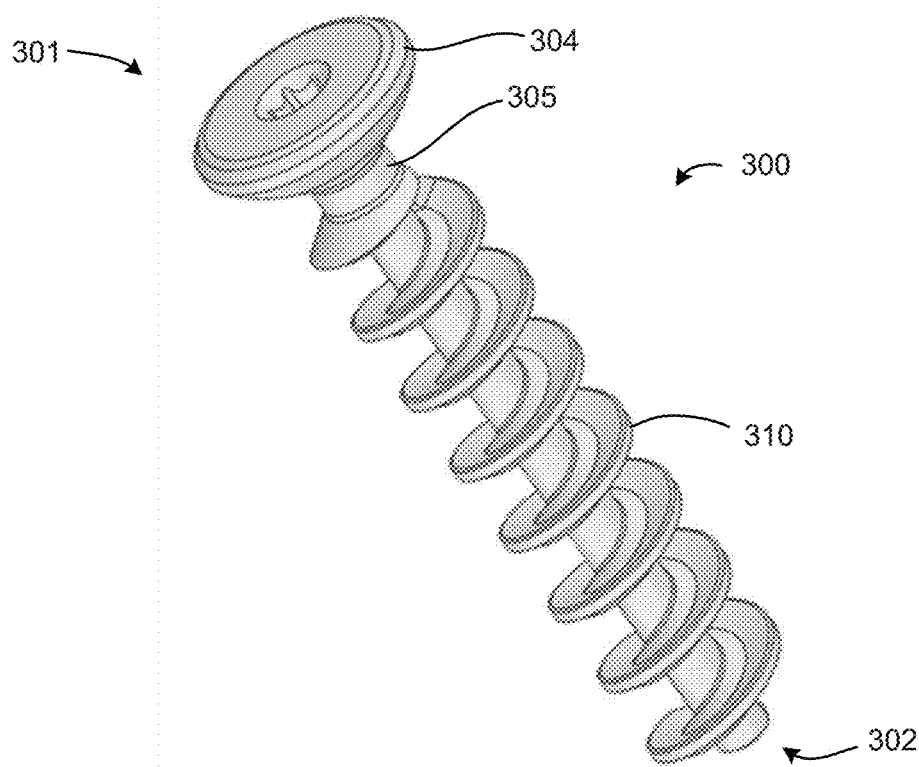
FIG. 3A illustrates a perspective side view of a fastener, according to another embodiment of the present disclosure.
Figure 3B:
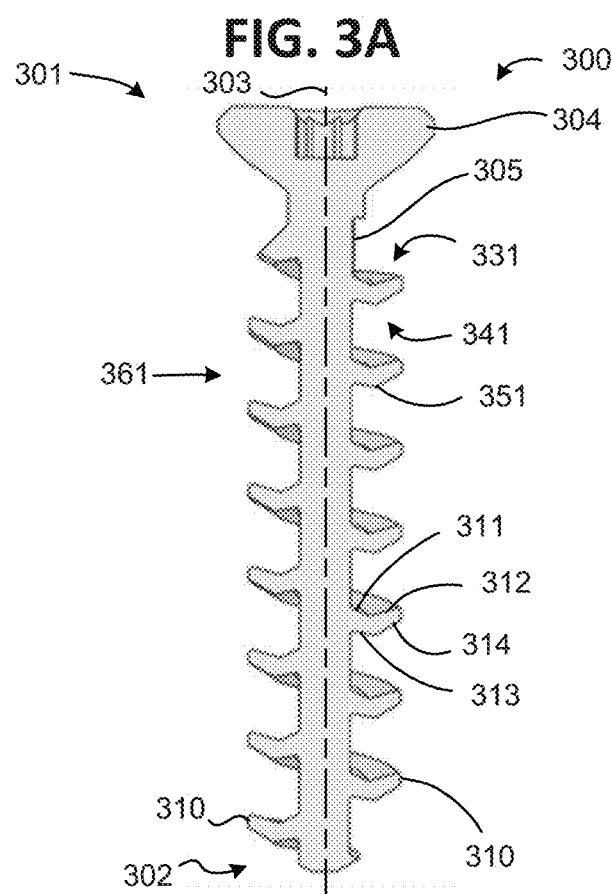
FIG. 3B illustrates a cross-sectional side view of the fastener of FIG. 3A.
Figure 4:
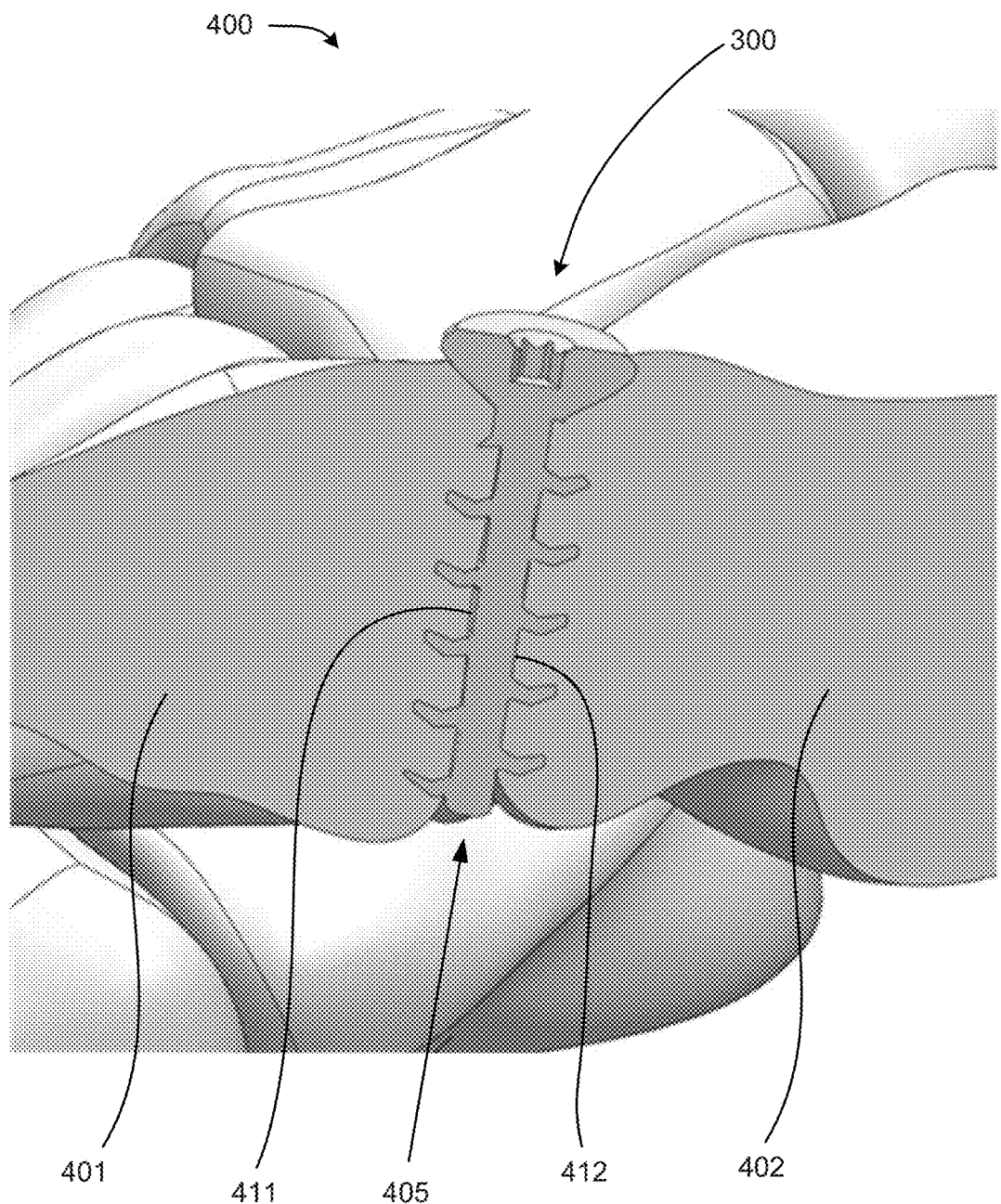
FIG. 4 illustrates a cross-sectional side view of the fastener of FIG. 3A implanted in a bone joint.

FIGS. 3A-4 illustrate various views of a bone disunion fastener or fastener 300, according to another example of the present disclosure. Specifically, FIG. 3A is a perspective side view of the fastener 300, FIG. 3B is a cross-sectional side view of the fastener 300, and FIG. 4 is a cross-sectional side view of the fastener 300 installed in a bone joint 400.

In general, the fastener 300 may include a fastener shaft or shaft 305 having a proximal end 301, a distal end 302, and a longitudinal axis 303, as well as a head 304 disposed at the proximal end 301 of the shaft 305 and a helical thread 310 disposed about the shaft 305 along the longitudinal axis 303.

In some embodiments, a depth of the helical thread 310 with respect to the shaft 305 may define a major diameter vs. a minor diameter of the shaft 305 alone.

In some embodiments, the major diameter, the minor diameter, and/or a pitch of the helical thread 310 may be constant or substantially constant along a length of the fastener 300.

In some embodiments, the helical thread 310 may include one or more concave undercut surfaces 331 and/or one or more convex undercut surfaces 341.

In some embodiments, the one or more concave undercut surfaces 331 may be angled towards one of the proximal end 301 and the distal end 302 of the shaft 305, and the one or more convex undercut surfaces 341 may be angled towards the other one of the proximal end 301 and the distal end 302 of the shaft 305.

In some embodiments, the one or more concave undercut surfaces 331 may be angled towards the proximal end 301 of the shaft 305 and the one or more convex undercut surfaces 341 may be angled towards the distal end 302 of the shaft 305.

In some embodiments, the one or more concave undercut surfaces 331 and/or the one or more convex undercut surfaces 341 may include a plurality of flat surfaces that are angled relative to each other.

In some embodiments, when the fastener 300 is implanted along a disunion 405 between a first bone portion 401 and a second bone portion 402, the one or more concave undercut surfaces 331 may be shaped to resist at least one force transmitted between the first bone portion 401 and the second bone portion 402 to stabilize the disunion 405, as shown in FIG. 4.

As used herein, the term "disunion" between one or more bone portions may include bone fractures, bone gaps, bone cracks, bone joint spaces, bone abutments, etc., between one or more bone portions.

In some embodiments, the helical thread 310 may include one or more first undercut surfaces 311 and one or more second undercut surfaces 312.

In some embodiments, the one or more first undercut surfaces 311 may be angled toward the proximal end 301 of the shaft 305, and one or more second undercut surfaces 312 may be angled toward the distal end 302 of the shaft 305.

In some embodiments, the helical thread 310 may also include one or more third undercut surfaces 313 and one or more fourth open surfaces 314. However, it will be understood that in other embodiments the one or more third undercut surfaces 313 and the one or more fourth open surfaces 314 may be replaced with any other shaped surface or surfaces (e.g., any buttress type thread shape, any flat surface that is angled toward or away from the one or more concave undercut surfaces 331, or angled 90 degrees with respect thereto, any curved surface that is generally oriented toward or away from the one or more concave undercut surfaces, etc.) without departing from the spirit or scope of the present disclosure. However, it will also be understood that the fastener 300 may (or may not) include any thread configuration, feature, or morphology described or contemplated herein with respect to any fastener/implant to achieve optimal fixation within a given bone, tissue, bone cement, bone augment material, etc. For example, in some embodiments the helical thread 310 may comprise standard or inverted threading, a "dual start" thread configuration, tapered helical threading, etc. Moreover, it will also be understood that the fastener 300 may be utilized in conjunction with (or within) any system, method, procedure, or instrumentation described or contemplated herein.

In some embodiments, when the fastener 300 is viewed in section along a plane intersecting the longitudinal axis 303 of the shaft 305, the helical thread 310 may include at least one chevron shape oriented toward one of the proximal end 301 and the distal end 302 of the shaft 305.

In some embodiments, when the fastener 300 is viewed in section along a plane intersecting the longitudinal axis 303 of the shaft 305, the helical thread 310 may include a plurality of chevron shapes oriented toward one of the proximal end 301 and the distal end 302 of the shaft 305.

In some embodiments, when the fastener 300 is viewed in section along a plane intersecting the longitudinal axis 303 of the shaft 305, the helical thread 310 may include at least one partial crescent shape oriented toward the proximal end 301 or the distal end 302 of the shaft 305.

In some embodiments, when the fastener 300 is viewed in section along a plane intersecting the longitudinal axis 303 of the shaft 305, the helical thread 310 may include a plurality of partial crescent shapes oriented toward one of the proximal end 301 and the distal end 302 of the shaft 305.

In some embodiments, when the fastener 300 is implanted across or along a disunion between two or more bones or bone portions (e.g., such as a bone fracture, a bone joint, bone abutments, etc.), the one or more concave undercut surfaces 331 may be oriented toward one of the proximal end 301 and the distal end 302 of the fastener 300, and the one or more convex undercut surfaces 341 may be oriented toward the other one of the proximal end 301 and the distal end 302 of the fastener 300. In this manner, the unique shape and configuration of the helical thread 310 can help mitigate or prevent loosening of the fastener 300 over time due to multi-axial forces and off-axis loading scenarios that may be applied to the fastener 300 along the disunion during the healing process.

In some embodiments, one or more interlocking spaces 361 may be formed between adjacent thread portions of the helical thread 310 along the shaft 305 of the fastener 300.

In some embodiments, the one or more interlocking spaces 361 may be shaped and/or configured to interlock with bone/other tissues received therein to increase fixation of the fastener 300 within the bone/other tissues and provide additional resistance against multi-axial forces that may be applied to the fastener 300 and/or the bone/other tissues.

In some embodiments, when the fastener 300 is viewed in section along a plane intersecting the longitudinal axis 303 of the shaft 305, the helical thread 310 may include one or more bent shapes (comprising at least one surface that is angled relative to the longitudinal axis 303 of the shaft 305 and/or at least one undercut surface) with one or more intermediate portions 351 that are oriented toward (i.e., point toward) one of the proximal end 301 and the distal end 302 of the shaft 305.

In some embodiments, at least one of: the one or more concave undercut surfaces 331, the one or more convex undercut surfaces 341, the one or more first undercut surfaces 311, the one or more second undercut surfaces 312, the one or more third undercut surfaces 313, and/or the one or more fourth open surfaces 314 may comprise at least one substantially flat surface.

In some embodiments, at least one of: the one or more concave undercut surfaces 331, the one or more convex undercut surfaces 341, the one or more first undercut surfaces 311, the one or more second undercut surfaces 312, the one or more third undercut surfaces 313, and/or the one or more fourth open surfaces 314 may comprise at least one curved surface.

Referring to FIG. 4, in some embodiments, when the fastener 300 is implanted along the disunion 405 formed between the first bone portion 401 and the second bone portion 402 (e.g., within a bone joint 400, a bone fracture, bone abutments, etc.), the one or more first undercut surfaces 311 may be angled towards one of the proximal end 301 and the distal end 302 of the shaft 305, the one or more second undercut surfaces 312 may be angled towards the other one of the proximal end 301 and the distal end 302 of the shaft 305, and the first and second undercut surfaces may be configured to resist at least one force transmitted between the first bone portion 401 and the second bone portion 402 to stabilize the disunion 405 between the first and second bone portions.

In some embodiments, the fastener 300 (or any other fastener/implant disclosed or contemplated herein) may be inserted across the disunion 405, along the disunion 405, and/or into that space defining the disunion 405 between two or more bone portions (or other anatomical structures), such that the helical thread 310 may engage the two or more bone portions (or other anatomical structures) radially with respect to the longitudinal axis 303 of the fastener 300 in order to resist at least one force that transmitted between the two or more bone portions during the healing process to stabilize the disunion 405.

In some embodiments, the one or more first undercut surfaces 311 may be angled towards the distal end 302 of the shaft 305 and the one or more second undercut surfaces 312 may be angled towards the proximal end 301 of the shaft 305.

In some embodiments, when the fastener 300 is viewed in section along a plane intersecting the longitudinal axis 303 of the shaft 305, the helical thread 310 may include at least one chevron shape oriented toward one of the proximal end 301 and the distal end 302 of the shaft 305.

In some embodiments, the helical thread 310 may include a plurality of chevron shapes oriented toward one of the proximal end 301 and the distal end 302 of the shaft 305.

In some embodiments, when the fastener 300 is viewed in section along a plane intersecting the longitudinal axis 303 of the shaft 305, the helical thread 310 may include at least one partial crescent shape oriented toward one of the proximal end 301 and the distal end 302 of the shaft 305.

In some embodiments, the helical thread 310 may include a plurality of partial crescent shapes oriented toward one of the proximal end 301 and the distal end 302 of the shaft 305.

In some embodiments, the fastener 300 (or any other fastener/implant disclosed or contemplated herein) may be utilized to hold two or more bone portions, bone fragments, anatomical surfaces, etc., in relative position with respect to each other, either temporarily, or indefinitely.

For example, a complex or comminuted fracture may include a bone that is broken in multiple places, which typically results in multiple fracture lines, bone fragments, crushed bone portions, etc., with multiple small bone pieces. Before a surgeon can apply definitive fixation to repair the complex fracture and promote healing in the correct orientation/position/shape, the pieces of bone may need to be reduced or set back into position and close proximity with respect to each other so healing can eventually occur in the correct orientation/position/shape. Traditional methods for reducing complex/comminuted fractures may include traditional clamps, wires, pins, K-wires, bone screws, etc., to reduce the complex/comminuted fractures until a more definitive fixation may be employed (e.g., with bone plates, intramedullary nails, etc.). However, utilization of traditional clamps, wires, pins, K-wires, bone screws, etc., typically results in additional bone loss given the small, asymmetric bone fragments (with poor surfaces) that are typically present in complex/comminuted fractures and inserting these traditional devices through the bone fragments will result in less untouched bone for use during later/more definitive fixation.

In contrast, the fasteners/implants described or contemplated herein may be utilized within or along a bone disunion to preserve bone by holding two or more bone pieces relative to each other within or along the bone disunion, allowing the helical thread geometry to penetrate opposing surfaces of the bone portions and interlock with each bone portion to hold them in relative position with respect to each other. Thus, by placing the fastener/implant directly in the disunion, fracture, gap, etc., the bone portions are preserved in volume and integrity, and can still offer additional space (and easier access to this additional space) for traditional fixation fasteners/implants that penetrate through the bone portions to provide additional fixation during a temporary fixation stage and/or a later more definitive fixation stage. The fasteners/implants described or contemplated herein may then be removed from the disunion after the temporary reduction stage has been completed, or they may be kept in place indefinitely as desired. In this manner, the fasteners/implants described or contemplated herein may provide more efficient reduction, better space utilization to allow for additional bone fixation devices, and/or better stabilization of bone portions in comparison to traditional clamps, wires, pins, K-wires, bone screws, etc.

Referring now to FIGS. 6A-7B, 11A, and 11B the fastener 300 may be combined with a bone staple or bone staple plate 610 to create bone disunion fastener or bone disunion assembly 600 that may provide additional stability for a disunion between two or more bone portions.

In some embodiments, the bone staple plate 610 may include a bridge 620 having a first end 621, a second end 622, and a middle portion 625 extending between the first end 621 and the second end 622 of the bridge 620.

In some embodiments, the middle portion 625 may include an opening or aperture 626 configured to receive the shaft 305 of the fastener 300 therethrough.

In some embodiments, the aperture 626 may be configured to engage the head 304 of the fastener 300 to couple the bone staple plate 610 with the fastener 300.

Figure 11A:
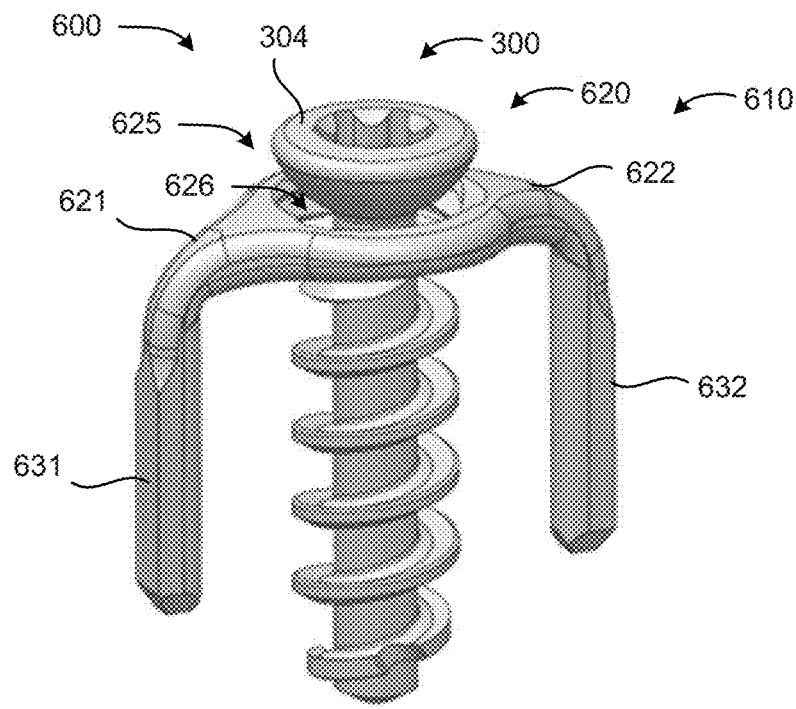
FIG. 11A illustrates a perspective side view of a fastener assembly, according to another embodiment of the present disclosure.

In some embodiments, the aperture 626 and/or the head 304 may each comprise partial spherical shapes that may be smooth, shaped, or otherwise configured to engage each other and provide polyaxial fixation of the head 304 with respect to the aperture 626 (e.g., see FIG. 11A).

Figure 11B:
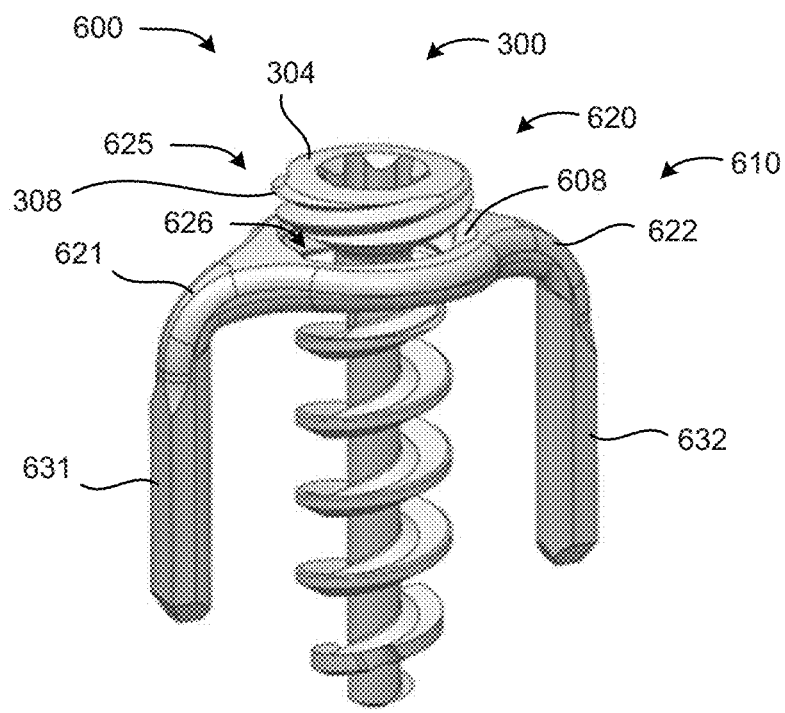
FIG. 11B illustrates a perspective side view of the fastener assembly of FIG. 11A with locking features.

In some embodiments, the head 304 may include a first locking feature 308 (e.g., a first locking thread, as one non-limiting example) and the middle portion 625 or aperture 626 may include a second locking feature 608 (e.g., a second locking thread, as one non-limiting example) that may be configured to engage each other to lock the head 304 of the fastener 300 to the bone staple plate 610 (e.g., see FIG. 11B). However, it will also be understood that any style of locking feature may be utilized with the fasteners/implants described or contemplated herein without departing from the spirit or scope of the present disclosure.

In some embodiments, the head 304 may include a locking feature and the aperture 626 may include a non-locking feature (e.g., a smooth partial spherical shape, as one non-limiting example).

In some embodiments, the head 304 may include a non-locking feature (e.g., a smooth partial spherical shape, as one non-limiting example) and the aperture 626 may include a locking feature.

In some embodiments, the first end 621 may include a first bone-engaging feature and the second end 622 may include a second bone-engaging feature.

In some embodiments, at least one of the first bone-engaging feature and the second bone-engaging feature may comprise at least one of: one or more roughened surfaces, one or more teeth, one or more blades, and one or more ribs, and one or more legs.

In some embodiments, the bone staple plate 610 may include a first leg 631 projecting away from the first end 621 of the bridge 620 along a first inferior direction, and a second leg 632 projecting inferiorly away from the second end 622 of the bridge 620 along a second inferior direction.

In some embodiments, the first inferior direction may be substantially parallel to the second inferior direction.

In some embodiments, when the fastener 300 is implanted along a disunion 405 that is formed between a first bone portion 401 and a second bone portion 402, the head 304 of the fastener 300 may engage the middle portion 625 of the bridge 620 to couple the fastener 300 and/or the shaft 305 of the fastener 300 with the bone staple plate 610.

In some embodiments, when the fastener 300 is implanted along a disunion 405 that is formed between a first bone portion 401 and a second bone portion 402, the first bone-engaging feature may engage the first bone portion 401 to couple the first end 621 of the bone staple plate 610 to the first bone portion 401.

In some embodiments, when the fastener 300 is implanted along a disunion 405 that is formed between a first bone portion 401 and a second bone portion 402, the second bone-engaging feature may engage the second bone portion 402 to couple the second end 622 of the bone staple plate 610 to the second bone portion 402.

In some embodiments, when the fastener 300 is implanted along a disunion 405 that is formed between a first bone portion 401 and a second bone portion 402, the bone staple plate 610 coupled to the first bone portion 401 and the second bone portion 402 may resist at least one force transmitted between the first bone portion 401 and the second bone portion 402 to stabilize the disunion 405.

In some embodiments, when the fastener 300 is implanted along a disunion 405 that is formed between a first bone portion 401 and a second bone portion 402, the first leg 631 of the bone staple plate 610 may penetrate the first bone portion 401 to couple the bone staple plate 610 to the first bone portion 401, and the second leg 632 of the bone staple plate 610 may penetrate the second bone portion 402 to couple the bone staple plate 610 to the second bone portion 402.

Figure 7A:
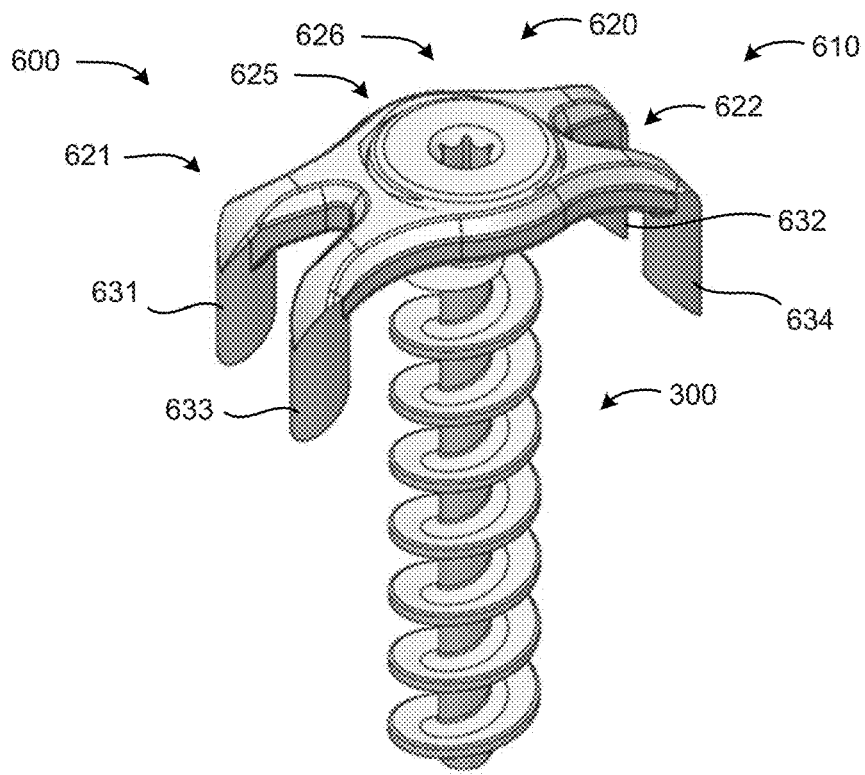
FIG. 7A illustrates a perspective side view of a fastener assembly, according to another embodiment of the present disclosure.
Figure 7B:
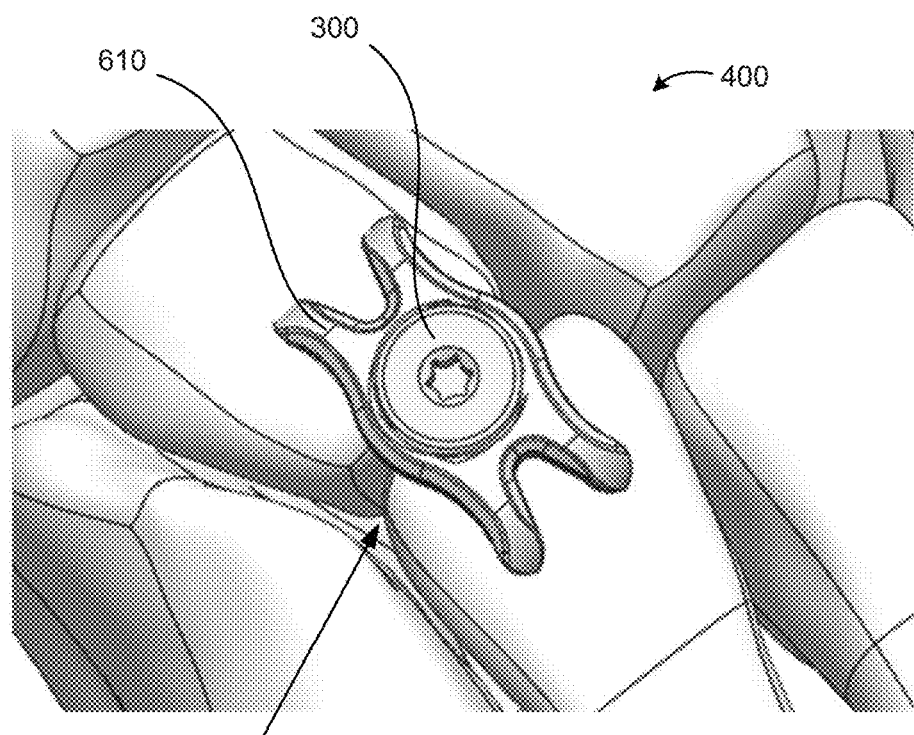
FIG. 7B illustrates a perspective top view of the fastener assembly of FIG. 7A installed in a bone joint.

In some embodiments, the bone staple plate 610 may further include a third leg 633 projecting away from the first end 621 of the bridge 620 along a third inferior direction and a fourth leg 634 projecting inferiorly away from the second end 622 of the bridge 620 along a fourth inferior direction (e.g., see FIG. 7A).

In some embodiments, the first inferior direction, the second inferior direction, the third inferior direction, and/or the fourth inferior direction may be substantially parallel to each other.

In some embodiments, a distal surface of the bridge 620 may be contoured/curved to fit a contour of a bone.

In some embodiments, the bone staple plate 610 may provide improved rotational stability and the fastener 300 may provide flexural stability for the bone disunion fastener or bone disunion assembly 600.

In some embodiments, the bone staple plate 610 may include a first leg 631 projecting away from the first end 621 of the bridge 620 along a first inferior direction, and the second end 622 of the bridge 620 may comprise one or more attachment features (not shown).

In some embodiments, the one or more attachment features may be configured to engage the second bone portion 402 to couple the bone staple plate 610 to the second bone portion 402.

In some embodiments, the one or more attachment features may comprise a roughened surface (not shown) configured to engage the second bone portion 402 to secure the second end 622 of the bridge 620 to the second bone portion 402 via a friction fit.

In some embodiments, the one or more attachment features may comprise a blade (not shown) configured to engage the second bone portion 402 to secure the second end 622 of the bridge 620 to the second bone portion 402.

In some embodiments, the one or more attachment features may comprise one or more ribs (not shown) configured to engage the second bone portion 402 to secure the second end 622 of the bridge 620 to the second bone portion 402.

In some embodiments, the one or more attachment features may comprise one or more teeth (not shown) configured to engage the second bone portion 402 to secure the second end 622 of the bridge 620 to the second bone portion 402.

In some embodiments, the one or more attachment features may comprise a second leg 632 configured to penetrate the second bone portion 402 to couple the bone staple plate 610 to the second bone portion 402.

In some embodiments, the first leg 631 may comprise a first plurality of legs projecting away from the first end 621 of the bridge 620 inferiorly, and the second leg 632 may comprise a second plurality of legs projecting away from the second end 622 of the bridge 620 inferiorly.

In some embodiments, the first and second plurality of legs may project substantially parallel to each other.

Figure 8A:
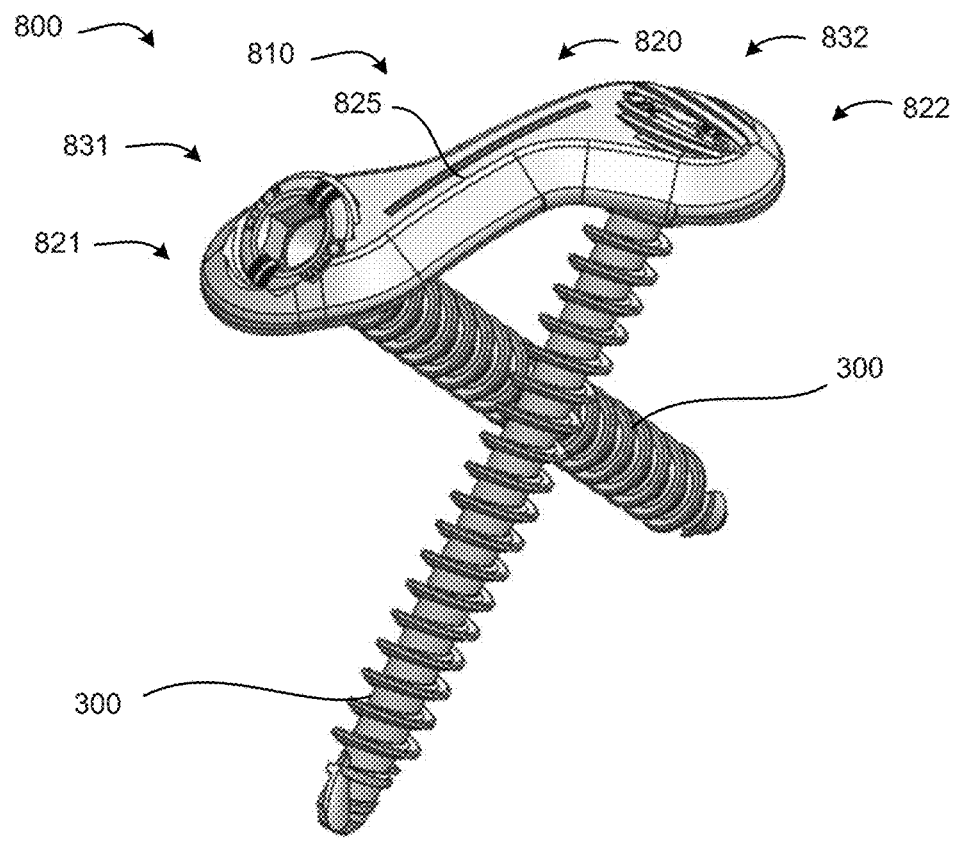
FIG. 8A illustrates a perspective side view of a fastener assembly, according to another embodiment of the present disclosure.
Figure 8B:
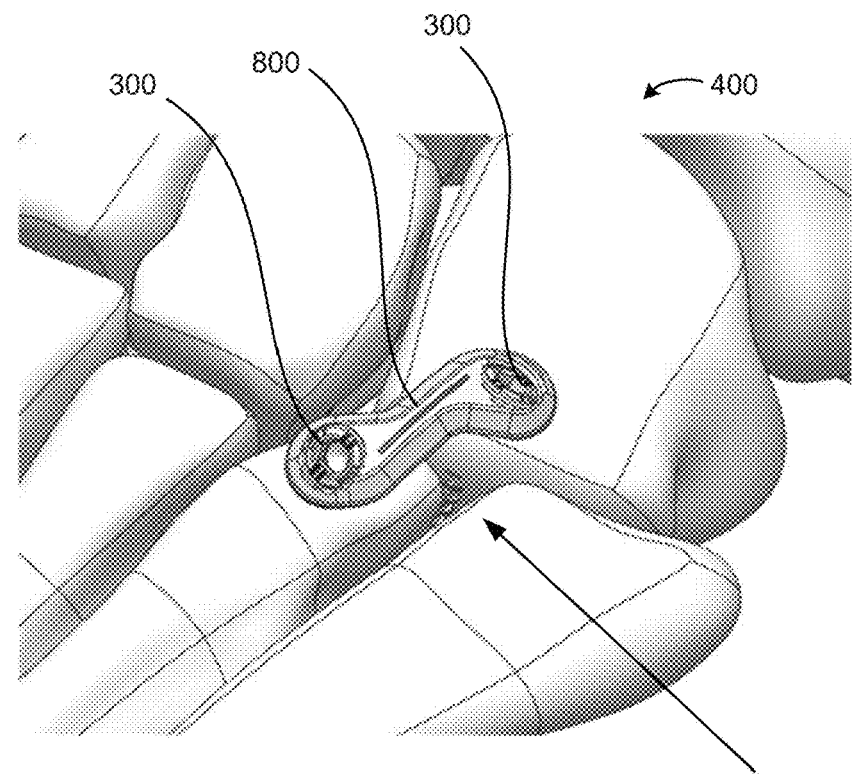
FIG. 8B illustrates a perspective top view of the fastener assembly of FIG. 8A installed in a bone joint.

Referring to FIGS. 8A and 8B, a bone disunion fastener or bone disunion assembly 800 may generally comprise a first bone disunion fastener, a second bone disunion fastener, and a bone plate or bone disunion plate 810. The bone disunion assembly 800 may utilize a crossed fastener design to stabilize a disunion 405 between two or more bone portions.

In some embodiments, the first bone disunion fastener and/or the second bone disunion fastener may comprise fasteners similar to the fastener 300 previously discussed herein.

In some embodiments, the bone disunion plate 810 may include a bridge 820 with a first end 821 including a first opening or first aperture 831 that may be configured to engage the first head of the first bone disunion fastener, a second end 822 including a second opening or second aperture 832 that may be configured to engage the second head of the second bone disunion fastener, and a middle portion 825 that may extend between the first end 821 and the second end 822 of the bridge 820.

In some embodiments, the first end 821 and/or the second end 822 may include at least one bone-engaging feature configured to couple with the first bone portion 401 and/or the second bone portion 402.

In some embodiments, the at least one bone-engaging feature may include at least one of: one or more roughened surfaces, one or more teeth, one or more blades, and one or more ribs, and one or more legs.

In some embodiments, when the bone disunion assembly 800 is implanted across a disunion 405 formed between a first bone portion 401 and a second bone portion 402, the first bone disunion fastener may penetrate through the first aperture 831 of the bridge 820, through the first bone portion 401, and into the second bone portion 402. Likewise, the second bone disunion fastener may penetrate through the second aperture 832 of the bridge 820, through the second bone portion 402, and into the first bone portion 401 in order to stabilize and/or compress the disunion 405 between the first and second bone portions.

In some embodiments, the bone disunion plate 810 may be contoured/curved to fit a contour of a bone.

In some embodiments, the first bone disunion fastener may form a first angle with respect to the bone disunion plate 810, and the second bone disunion fastener may form a second angle with respect to the bone disunion plate 810.

In some embodiments, the first angle and the second angle may be congruent with each other.

In some embodiments, the first angle and the second angle may be non-congruent with each other.

In some embodiments, the first angle and the second angle may be chosen such that a point of crossing between the first bone disunion fastener and the second bone disunion fastener may reside within a selected one of: the first bone portion 401, the second bone portion 402, and the disunion 405. In this manner, one or more stress concentrations that may occur at the point of crossing may be selectively located within the first bone portion 401, the second bone portion 402, and/or the disunion 405 in order to ameliorate the effects of the one or more stress concentrations, as desired.

Figure 5A:
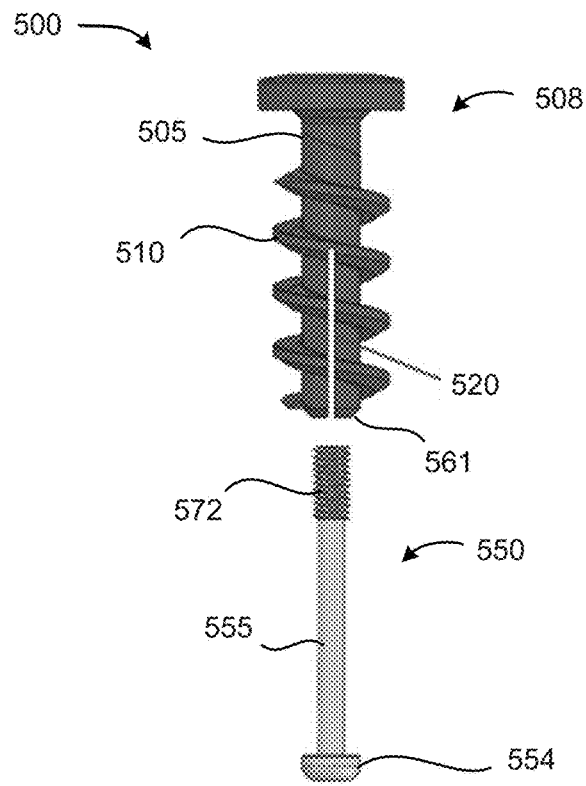
FIG. 5A illustrates an exploded view of a fastener assembly, according to another embodiment of the present disclosure.
Figure 5B:
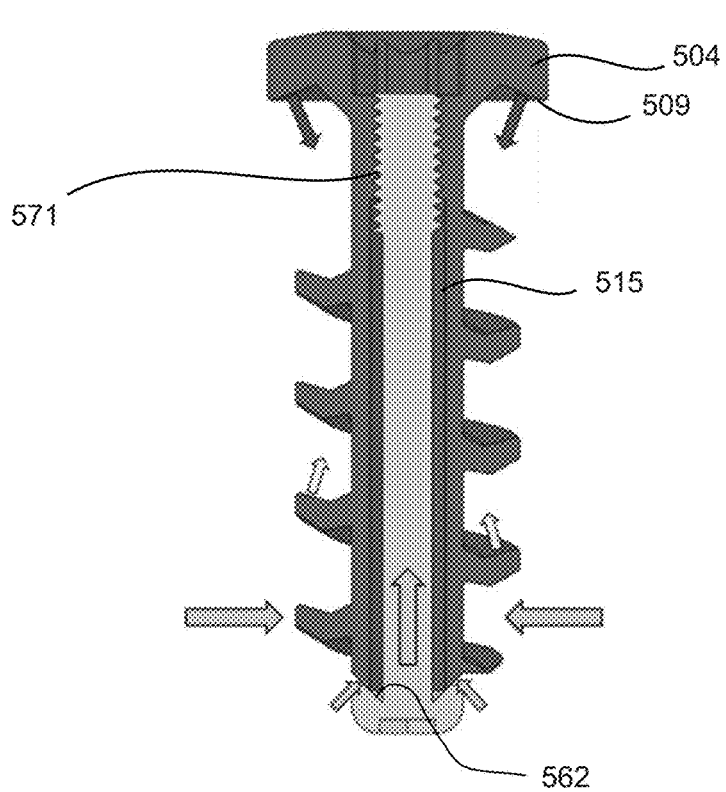
FIG. 5B illustrates a cross-sectional side view of the fastener assembly of FIG. 5A, after assembly.
Figure 5C:
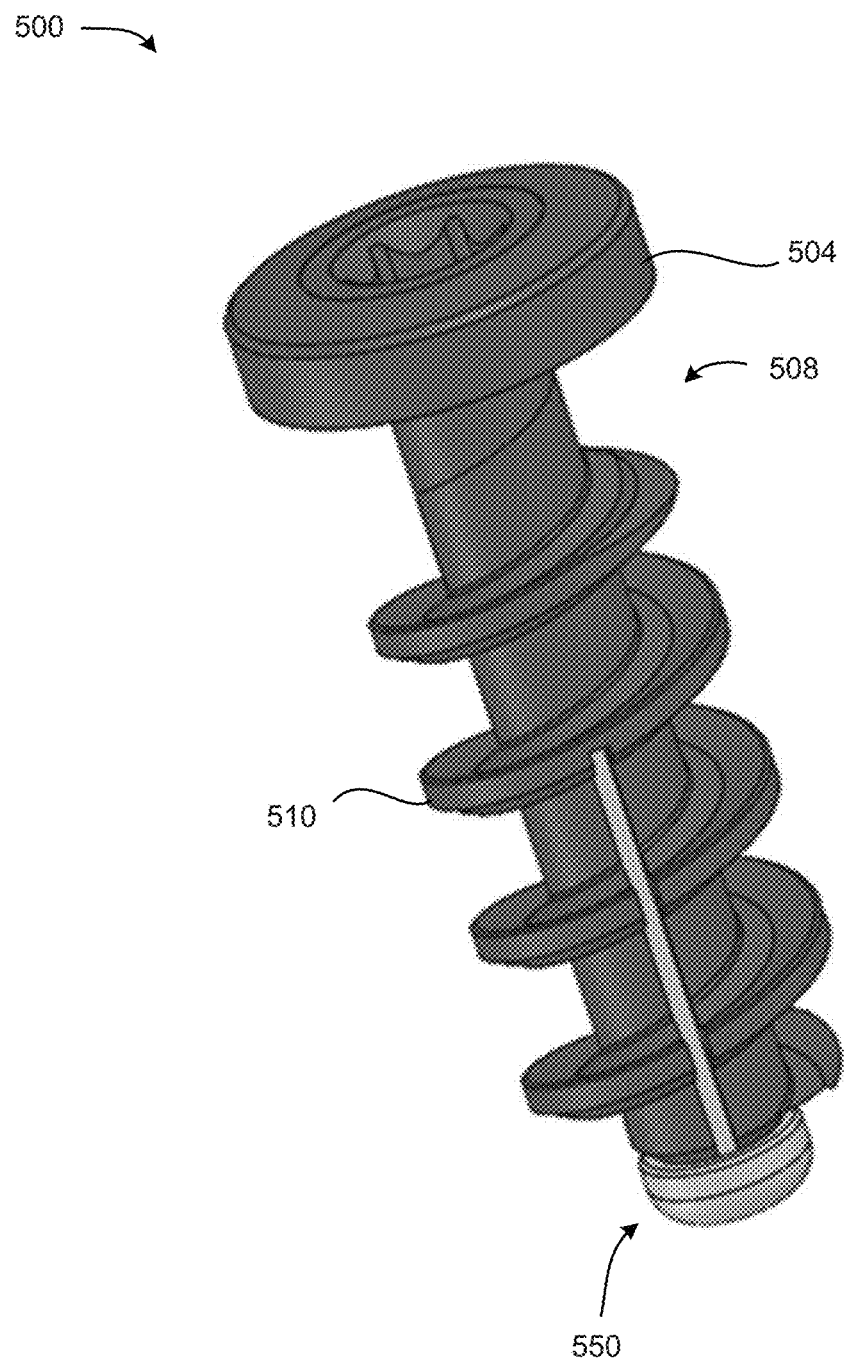
FIG. 5C illustrates a perspective side view of the fastener assembly of FIG. 5A, after assembly.
Figure 6A:
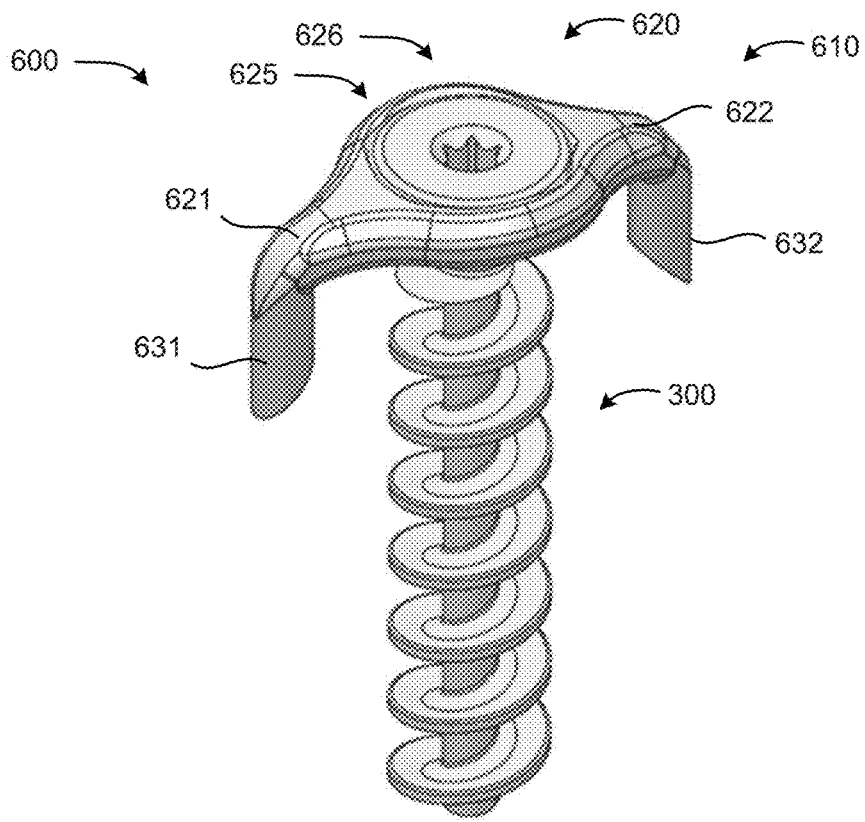
FIG. 6A illustrates a perspective side view of a fastener assembly, according to another embodiment of the present disclosure.
Figure 6B:
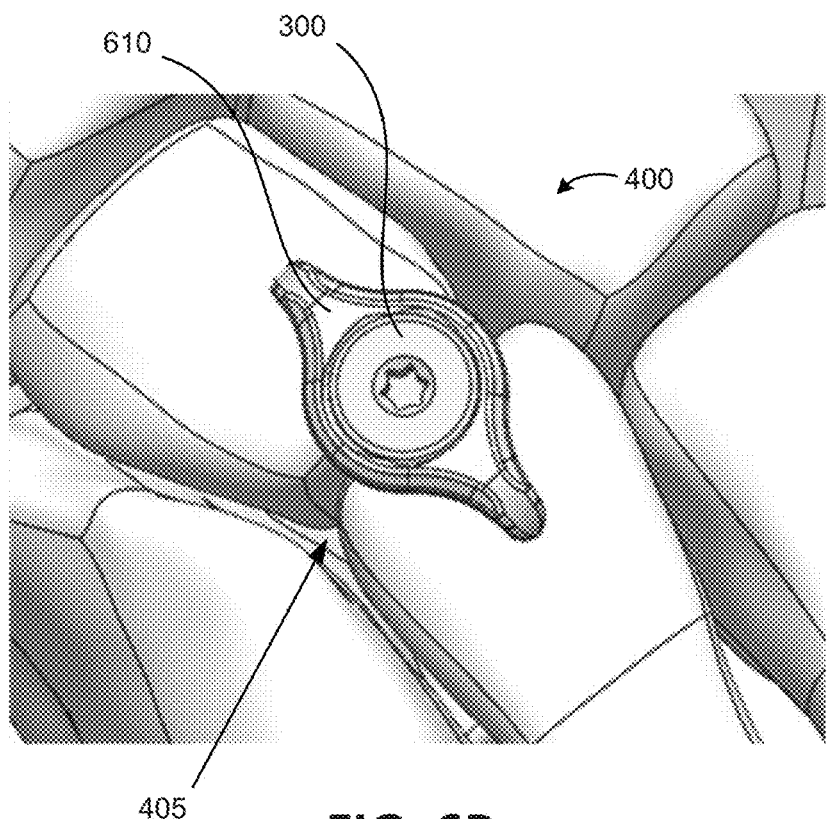
FIG. 6B illustrates a perspective top view of the fastener assembly of FIG. 6A installed in a bone joint.

Referring to FIGS. 5A-5C, a bone disunion fastener or bone disunion assembly 500 may include a split fastener, compressible fastener shaft, or bone disunion fastener 508 couplable with a fastener insert, compression member, or insert member 550, forming a compression system configured to move the compressible fastener shaft from a first non-compressed state to a second compressed state.

In some embodiments, the bone disunion fastener 508 may include a compressible fastener shaft or fastener shaft 505 comprising a proximal end, a distal end, a longitudinal axis, an inner bore 515 within the fastener shaft 505, and at least one collet feature 520 that may be configured to allow the fastener shaft 505 to compress in a radial direction and/or a longitudinal direction.

In some embodiments, the bone disunion fastener 508 may also include a fastener head 504 disposed at the proximal end of the fastener shaft 505 and a helical thread 510 disposed about the fastener shaft 505 along the longitudinal axis.

In some embodiments, the helical thread 510 may include at least one concave undercut surface oriented toward one of the proximal end and the distal end of the fastener shaft 505.

In some embodiments, the insert member 550 may include a compression member shaft or insert shaft 555 configured to be received within the inner bore 515 of the fastener shaft 505.

In some embodiments, the insert shaft 555 may include a proximal end, a distal end, a longitudinal axis, and a compression member head or insert head 554 disposed at the proximal end of the insert shaft 555.

In some embodiments, the compression system may include the inner bore 515 formed within the compressible fastener shaft, the at least one collet feature 520 formed in the compressible fastener shaft about the inner bore 515, and the compression member configured to move the at least one collet feature 520 radially toward the longitudinal axis of the compressible fastener shaft and move the compressible fastener shaft from the first non-compressed state to the second compressed state.

In some embodiments, the compression member may be removably couplable with the compressible fastener shaft and the compression member may engage the distal end of the compressible fastener shaft to move the at least one collet feature radially and compress the compressible fastener shaft.

In some embodiments, when the bone disunion fastener 508 is implanted along a disunion 405 formed between a first bone portion 401 and a second bone portion 402, the compression system may move the compressible fastener shaft from the first non-compressed state to the second compressed state.

In some embodiments, when the bone disunion fastener 508 is implanted along a disunion 405 formed between a first bone portion 401 and a second bone portion 402, the insert head 554 may engage the distal end of the fastener shaft 505 and compress the fastener shaft 505 along at least one of a radial direction and a longitudinal direction.

In some embodiments, when the bone disunion fastener 508 is implanted along a disunion 405 formed between a first bone portion 401 and a second bone portion 402, the fastener head 504 may engage and compress an external surface of the first and second bone portions across the disunion 405 along a first direction.

In some embodiments, when the bone disunion fastener 508 is implanted along a disunion 405 formed between a first bone portion 401 and a second bone portion 402, the at least one concave undercut surface of the helical thread 510 may engage and compress at least one internal surface of the first and second bone portions across the disunion 405 along a second direction, substantially opposite the first direction, to resist at least one force transmitted between the first bone portion 401 and the second bone portion 402 to stabilize the disunion.

In some embodiments, when the bone disunion fastener 508 is implanted along a disunion 405 formed between a first bone portion 401 and a second bone portion 402, the concave undercut surface may compress the first bone portion 401 toward the second bone portion 402 to resist at least one force transmitted between the first bone portion 401 and the second bone portion 402 to stabilize the disunion 405.

In some embodiments, a distal end of the fastener head 504 may include a concave shape or a concave surface 509.

In some embodiments, a distal end of the fastener shaft 505 may include a first chamfered surface 561.

In some embodiments, a distal end of the insert head 554 may include a second chamfered surface 562.

In some embodiments, the second chamfered surface 562 of the insert head 554 may be configured to engage the first chamfered surface 561 of the fastener shaft 505 and move the at least one collet feature 520 radially and compress the fastener shaft 505 along at least one of a radial direction and/or a longitudinal direction.

In some embodiments, the first chamfered surface 561 may comprise a convex surface.

In some embodiments, the second chamfered surface may comprise a concave surface.

In some embodiments, the at least one collet feature 520 may comprise one or more slots formed in the fastener shaft 505 along the longitudinal axis of the fastener shaft 505.

In some embodiments, the inner bore may include an internal thread 571.

In some embodiments, the insert shaft may include an external thread 572 configured to engage the internal thread 571 of the inner bore 515 to couple the insert member 550 to the bone disunion fastener 508 and compress the fastener shaft 505 along at least one of the radial direction and the longitudinal direction. In this manner, the insert head 554 may compress a distal portion of the fastener shaft inwardly causing the at least one undercut surface oriented toward the fastener head 504 to compress bone toward the fastener head 504 while the fastener head 504 compresses bone under its concave surface 509 toward the at least one undercut surface, as shown in FIG. 5B. Thus, the bone disunion assembly 500 utilizes an active compression force to increase fixation and stabilize the disunion 405.

In some embodiments, an external surface of the first and second bone portions across the disunion may be shaped with a suitable tool (not shown) to include a mating geometry corresponding to the concave surface 509 of the fastener head 504.

In some embodiments, the concave surface 509 of the fastener head 504 may be configured to draw the two bone portions together as the bone disunion assembly 500 is installed in the disunion 405 and tightened.

In some embodiments, the at least one concave undercut surface of the helical thread 510 may be configured to draw the two bone portions together as the bone disunion assembly 500 is installed in the disunion 405 and tightened.

Figure 9A:
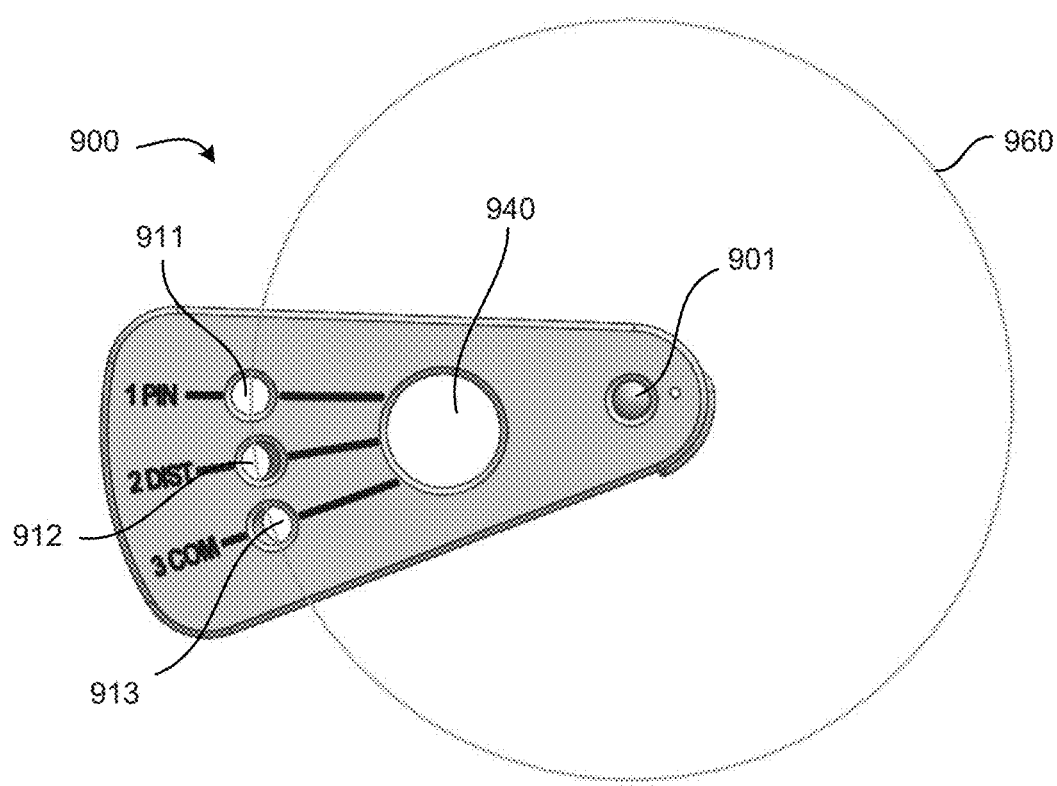
FIG. 9A illustrates a top view of a distraction-compression block, according to an embodiment of the present disclosure.
Figure 9B:
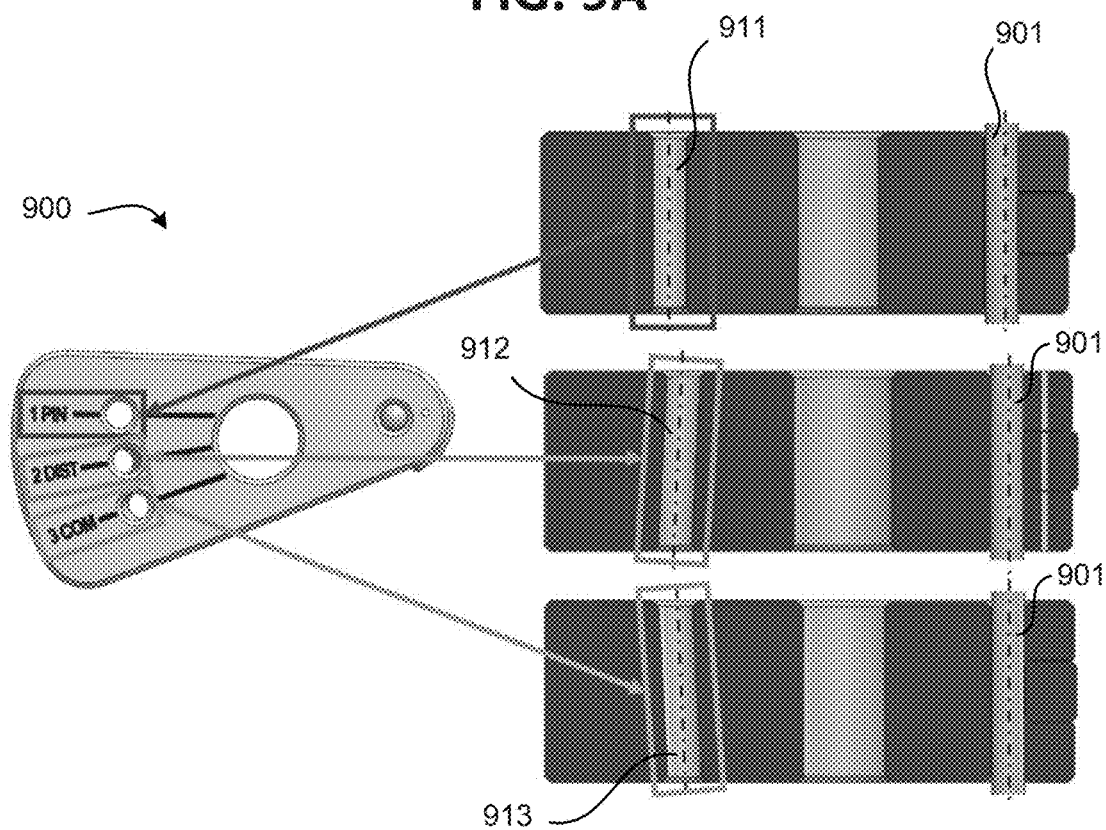
FIG. 9B illustrates various cross-sectional side views of the distraction-compression block of FIG. 9A.
Figure 10:
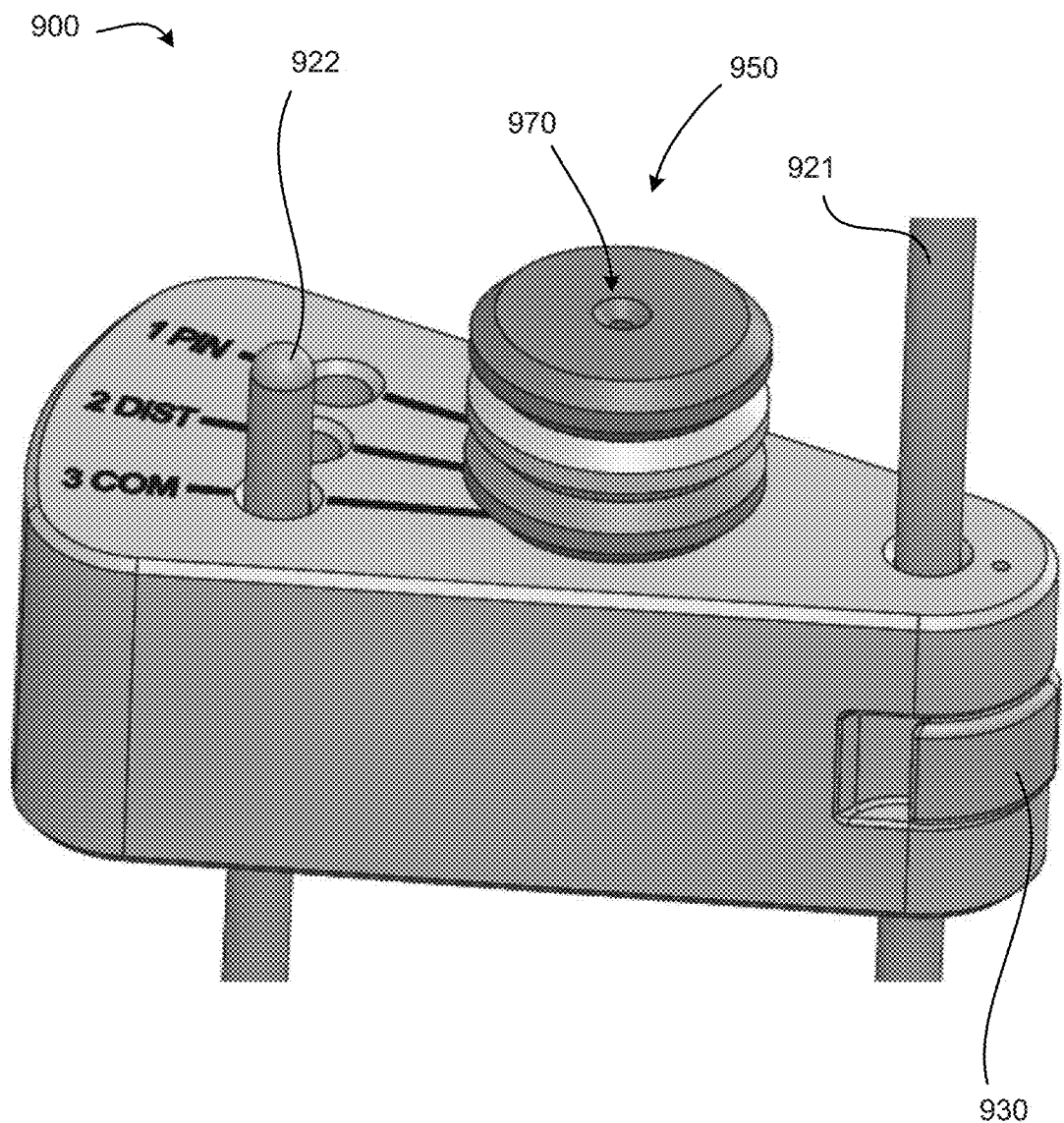
FIG. 10 illustrates a perspective top view of the distraction-compression block of FIG. 9A coupled with one or more insert guides.

FIGS. 9A-10 illustrate various views of a bone disunion instrument system that may include a first bone pin 921, a second bone pin 922, and a distraction-compression block 900, according to an embodiment of the present disclosure. The distraction-compression block 900 may also be referred to herein as a guide block, a placement block, or implant insertion block. FIGS. 9A and 9B show top views of the distraction-compression block 900, FIG. 9B shows various cross-sectional side views of the distraction-compression block 900, and FIG. 10 illustrates a perspective top view of the distraction-compression block 900 with one or more insert guides 950.

In some embodiments, the first bone pin 921 may include a first proximal end 931 (e.g., see FIG. 13) and a first distal end 941 configured to anchor in a first bone portion (such as the first bone portion 401 shown in FIG. 4), and the second bone pin 922 may include a second proximal end 932 and a second distal end 942 configured to anchor in a second bone portion such as the second bone portion 402 shown in FIG. 4). The second bone portion may be positioned adjacent the first bone portion and a bone disunion may be formed intermediate the first bone portion and the second bone portion.

In some embodiments, the distraction-compression block 900 may be configured to aid the preparation and fusion of a bone disunion (such as a bone joint, bone fracture, etc.) during a surgical procedure by utilizing the distraction-compression block 900 in combination with the first bone pin 921 and the second bone pin 922 to distract a bone disunion during surface preparation, then compress the bone disunion (and/or hold the bone disunion under compression) to install a suitable implant into the bone disunion to fix/fuse the bone disunion.

In some embodiments, the distraction-compression block 900 may include a first bone pin hole or first pin hole 901, one or more second bone pin holes (e.g., a parallel pin hole 911, a diverging pin hole 912, and a converging pin hole 913), a window or central aperture 940 formed through the distraction-compression block 900 intermediate the first pin hole 901 and the one or more second bone pin holes, and a locking feature 930.

In some embodiments, the parallel pin hole 911, the diverging pin hole 912, and the converging pin hole 913 may be arranged along a circle 960 to allow for simple rotation of the distraction-compression block 900 between successive steps in the surgical procedure.

In some embodiments, longitudinal axes of the first pin hole 901 and the parallel pin hole 911 may be substantially parallel to each other in general orientation.

In some embodiments, a longitudinal axis or distal end of the diverging pin hole 912 may diverge away from the longitudinal axis of the first pin hole 901 in general orientation.

In some embodiments, a longitudinal axis or distal end of the converging pin hole 913 may converge toward the longitudinal axis of the first pin hole 901 in general orientation.

In some embodiments, the first bone pin 921 may be longer than the second bone pin 922.

In some embodiments, the first bone pin 921 may be inserted into a first bone portion on a first side of a bone disunion (e.g., a bone fracture, a bone joint such as the disunion 405 shown in FIG. 4, etc.). The first bone pin 921 may then be inserted into the first pin hole 901 of the distraction-compression block 900. The second bone pin 922 may then be inserted through the parallel pin hole 911 of the distraction-compression block 900 and into a second bone portion on a second side of the bone joint.

In some embodiments, the distraction-compression block 900 may then be slid up the first bone pin 921 and off the shorter second bone pin 922.

In some embodiments, the distraction-compression block 900 may then be rotated to the "2 DIST" or diverging pin hole 912 location and slid back down over the second bone pin 922. Because the distal end of the diverging pin hole 912 diverges away from the first pin hole, distraction of the bone joint will occur as the distraction-compression block 900 is slid down over the first and second bone pins toward the joint. Moreover, the further the distraction-compression block 900 is slid down the first and second bone pins toward the joint, the more distraction may be achieved.

In some embodiments, a locking feature 930 (such as a cam or a frictional surface finish inside the first pin hole 901, etc.) may be utilized to hold the distraction-compression block 900 in place on the first and second bone pins in order to maintain a desired distraction position.

In some embodiments, while the joint is held in the desired distracted position, bone surfaces on both sides of the joint may be accessed and prepared for fixation/fusion. After this bone preparation step is complete, the locking feature 930 may then be released and the distraction-compression block 900 may be slid back up to release the second bone pin 922 from the diverging pin hole 912.

In some embodiments, the distraction-compression block 900 may then be rotated to the "3 COM" or converging pin hole 913 position and the second bone pin 922 may be inserted therein. Because the distal end of the converging pin hole 913 converges toward the first pin hole 901, compression will occur as the distraction-compression block 900 is slid down the first and second bone pins toward the joint. Moreover, the further the distraction-compression block 900 is slid down the first and second bone pins toward the joint, the more compression may be achieved.

In some embodiments, the locking feature 930 may then be utilized to hold the distraction-compression block 900 in place on the first and second bone pins in order to maintain a desired compression position.

In some embodiments, the desired compression position may be maintained while subsequent steps in the surgical procedure are performed (e.g., fixation steps including, but not limited to: drilling, tapping, inserting the implant, etc.).

In some embodiments, the distraction-compression block 900 may also include one or more insert guides 950. In some embodiments, the one or more insert guides 950 may include one or more guide holes 970 formed therethrough.

In some embodiments, the one or more insert guides 950 may be at least partially received within or inserted into the central aperture 940 and/or positioned directly over the joint in order to guide placement of a preliminary guide pin or spade guide 1400 (e.g., see FIG. 14) to ensure proper joint orientation before the first bone pin 921 is inserted into the first bone portion, as will be discussed below in more detail with reference to FIGS. 12A-14.

In some embodiments, the one or more insert guides 950 may also be utilized to facilitate other steps in the surgical procedure such as a guide for drilling, tapping, inserting an implant, etc.

In some embodiments comprising a bone staple, a bone plate, or any other additional implant structure described or contemplated herein, the one or more insert guides 950 may be configured to accommodate placement of these structures through the window and/or around the distraction-compression block 900 while the joint is held in a desired compression or distraction position.

In some embodiments, when the first bone pin 921 is anchored in the first bone portion and inserted through the first pin hole 901, and the second bone pin 922 is anchored in the second bone portion and inserted through the converging pin hole 913, the first pin hole 901 may impart a first force on the first bone pin 921 along a first direction toward the converging pin hole 913 to compress the first bone portion toward the second bone portion. Likewise, the converging pin hole 913 may impart a second force on the second bone pin 922 along a second direction toward the first pin hole 901 to compress the second bone portion toward the first bone portion. In this manner, the window or central aperture 940 may be configured to provide access for an implant (e.g., any of the implants disclosed or contemplated herein) to be placed through the central aperture 940 and into/proximate the bone disunion while the bone disunion is under compression (or distraction), in order to stabilize, fixate, or fuse the bone disunion via the implant that is placed into/proximate the bone disunion.

As used herein, the terms "stabilizing" or "to stabilize" may include long-term or short-term stabilization of a bone disunion via one or more implants (and/or implant instruments) that are implanted in or near one or more of the bones or bone portions comprising the bone disunion.

In some embodiments, when the first bone pin 921 is anchored in the first bone portion and inserted through the first pin hole 901, and the second bone pin 922 is anchored in the second bone portion and inserted through the diverging pin hole 912, the first pin hole 901 may impart a first force on the first bone pin 921 along a first direction away from the diverging pin hole 912 to distract the first bone portion away from the second bone portion. Likewise, the diverging pin hole 912 may impart a second force on the second bone pin 922 along a second direction away from the first pin hole 901 to distract the second bone portion away from the first bone portion. In this manner, the window or central aperture 940 may be configured to provide access for an implant (e.g., any of the implants disclosed or contemplated herein) to be placed through the central aperture 940 and into the bone disunion while the bone disunion is under distraction (or compression), in order to stabilize the bone disunion.

Figure 12A:
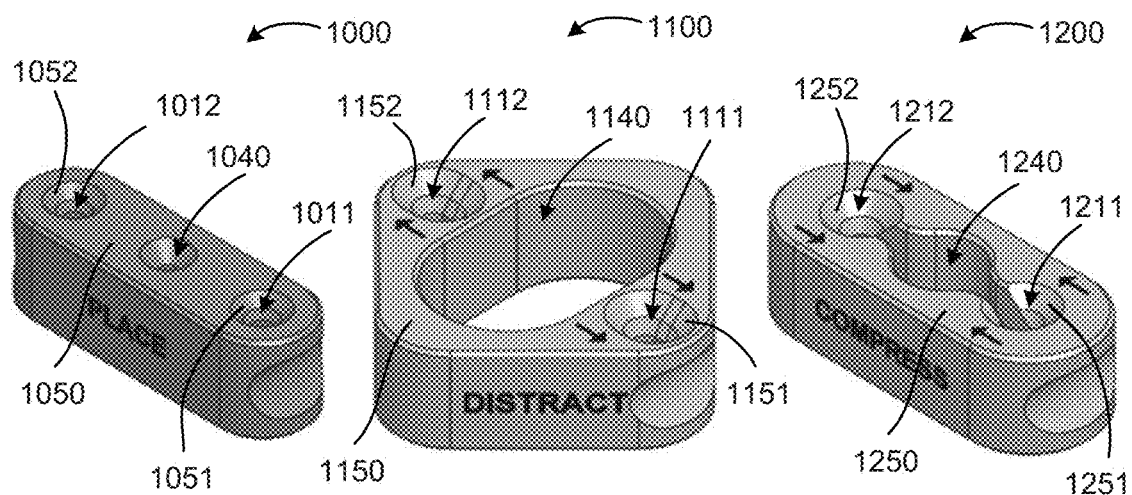
FIG. 12A illustrates perspective top views of a placement block, a distraction block, and a compression block, according to embodiments of the present disclosure.
Figure 12B:
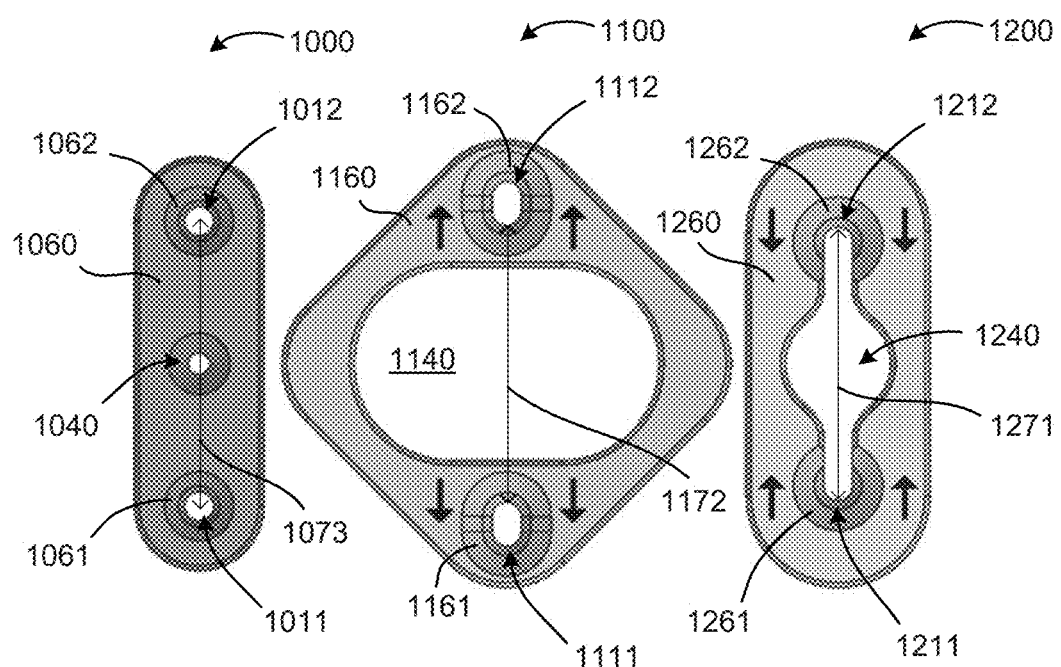
FIG. 12B illustrates bottom views of the placement block, distraction block, and compression block of FIG. 12A.
Figure 13:
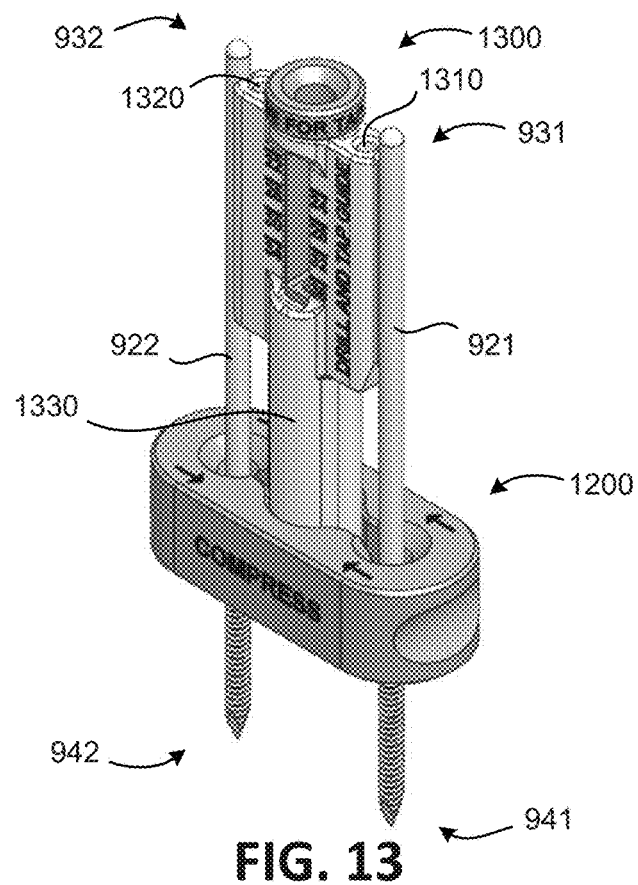
FIG. 13 illustrates a perspective side view of the compression block of FIG. 12A in combination with a guide tool.
Figure 14:
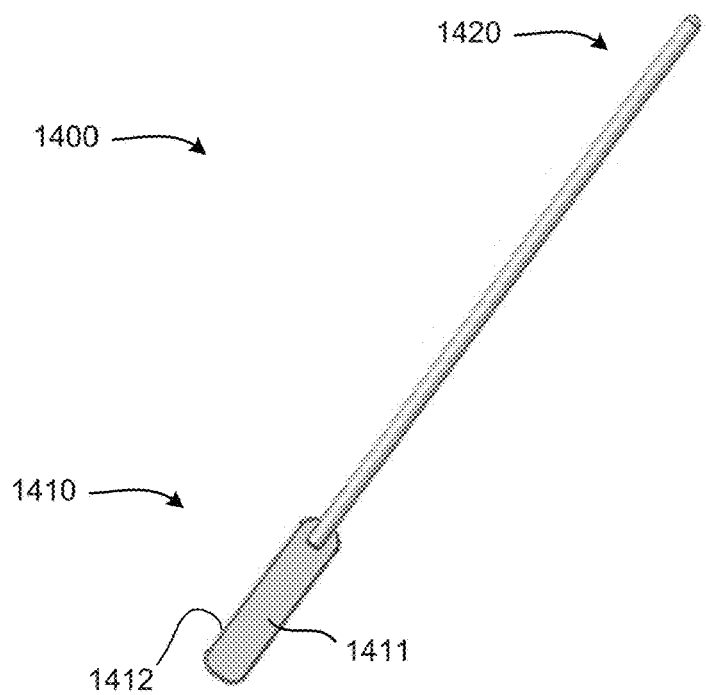
FIG. 14 illustrates a side view of a spade guide, according to an embodiment of the present disclosure.

FIGS. 12A-14 illustrate various components for one or more bone disunion instrument systems, according to embodiments of the present disclosure. Specifically, FIGS. 12A and 12B show perspective top views and bottom views of a guide block, implant insertion block, or placement block 1000, a guide block, implant insertion block, or distraction block 1100, and a guide block, implant insertion block, or compression block 1200, according to embodiments of the present disclosure. FIG. 13 shows a perspective side view of the compression block 1200 of FIG. 12A in combination with a guide tool 1300, and FIG. 14 shows a side view of a spade guide 1400.

The placement block 1000, the distraction block 1100, and/or the compression block 1200 may also be referred to herein as a block, a guide block, or an implant insertion block.

The placement block 1000, distraction block 1100, and compression block 1200 may be configured to aid the preparation and fusion of a bone disunion (such as a bone joint, bone fracture, etc.) during a surgical procedure by utilizing each block in combination with the first bone pin 921 and the second bone pin 922 to: place the first bone pin 921 and the second bone pin 922 on either side of a bone disunion, distract the bone disunion during surface preparation, then compress the bone disunion (and/or hold the bone disunion under compression) to install a suitable implant (e.g., any of the implants described or contemplated herein) into the bone disunion to stabilize/fix/fuse the bone disunion.

In some embodiments, the placement block 1000 may include a first bone pin hole 1011, a second bone pin hole 1012, a placement block hole or placement block window 1040, a superior surface 1050, an inferior surface 1060, a first inferior lead-in feature 1061, a second inferior lead-in feature 1062, a first superior lead-in feature 1051, and a second superior lead-in feature 1052.

As defined herein, the term "lead-in feature" can include any shape or structure proximate a bone pin hole that is formed through any guide block disclosed or contemplated herein that may facilitate or guide insertion of one or more bone pins into the bone pin hole. For example, lead-in features may include, but are not limited to, chamfered edges having any shape or size (e.g., circular shaped chamfered edges, conical shaped elliptical shaped chamfered edges, parabolic shaped chamfered edges, etc.), bone pin holes having more than one radius/shape, and the like.

In some embodiments, the distraction block 1100 may include a first bone pin hole 1111, a second bone pin hole 1112, a distraction block hole or distraction block window 1140, a superior surface 1150, an inferior surface 1160, a first inferior lead-in feature 1161, a second inferior lead-in feature 1162, a first superior lead-in feature 1151, and a second superior lead-in feature 1152.

In some embodiments, the compression block 1200 may include a first bone pin hole 1211, a second bone pin hole 1212, a compression block hole or compression block window 1240, a superior surface 1250, an inferior surface 1260, a first inferior lead-in feature 1261, a second inferior lead-in feature 1262, a first superior lead-in feature 1251, and a second superior lead-in feature 1252.

In some embodiments, the compression block window 1240 and one or more of the first bone pin hole 1211 and the second bone pin hole 1212 may be joined together, as shown in FIGS. 12A and 12B. However, it will be understood that the windows of any guide block disclosed or contemplated herein may assume any shape, size, configuration, etc. Moreover, the windows of any guide block disclosed or contemplated herein may be fully or partially bounded by one or more sidewalls of the guide block.

In some embodiments, each of the placement block 1000, the distraction block 1100, and the compression block 1200 may (or may not) include a locking feature (not shown), as previously described herein with respect to FIGS. 9A-10.

In some embodiments, when the first bone pin 921 is anchored in the first bone portion and inserted through the first bone pin hole 1211 of the compression block 1200, and the second bone pin 922 is anchored in the second bone portion and inserted through the second bone pin hole 1212 of the compression block 1200, the first bone pin hole 1211 may impart a first force on the first bone pin 921 along a first direction toward the second bone pin hole 1212 to compress the first bone portion toward the second bone portion. Likewise, the second bone pin hole 1212 may impart a second force on the second bone pin 922 along a second direction toward the first bone pin hole 1211 to compress the second bone portion toward the first bone portion. In this manner, the compression block window 1240 may be configured to provide access for an implant (e.g., any of the implants disclosed or contemplated herein) to be placed through the compression block window 1240 and into the bone disunion while the bone disunion is under compression, to stabilize the bone disunion.

In some embodiments, when the first bone pin 921 is anchored in the first bone portion and inserted through the first bone pin hole 1111 of the distraction block 1100, and the second bone pin 922 is anchored in the second bone portion and inserted through the second bone pin hole 1112 of the distraction block 1100, the first bone pin hole 1111 may impart a first force on the first bone pin 921 along a first direction away from the second bone pin hole 1112 to distract the first bone portion away from the second bone portion. Likewise, the second bone pin hole 1112 may impart a second force on the second bone pin 922 along a second direction away from the first bone pin hole 1111 to distract the second bone portion away from the first bone portion. In this manner, the distraction block window 1140 may be configured to provide access for an implant (e.g., any of the implants disclosed or contemplated herein) to be placed through the distraction block window 1140 and into the bone disunion while the bone disunion is under distraction, to stabilize the bone disunion.

In some embodiments, longitudinal axes of the first bone pin hole 1211 and the second bone pin hole 1212 of the compression block 1200 may be substantially parallel to each other in general orientation. However, it will also be understood that the longitudinal axes of the first bone pin hole 1211 and the second bone pin hole 1212 of the compression block 1200 may diverge away from and/or converge toward each other.

In some embodiments, longitudinal axes of the first bone pin hole 1111 and the second bone pin hole 1112 of the distraction block 1100 may be substantially parallel to each other in general orientation. However, it will also be understood that the longitudinal axes of the first bone pin hole 1111 and the second bone pin hole 1112 of the distraction block 1100 may diverge away from and/or converge toward each other.

In some embodiments, longitudinal axes of the first bone pin hole 1011 and the second bone pin hole 1012 of the placement block 1000 may be substantially parallel to each other in general orientation. However, it will also be understood that the longitudinal axes of the first bone pin hole 1011 and the second bone pin hole 1012 of the placement block 1000 may diverge away from and/or converge toward each other.

In some embodiments, each of the bone pin holes formed in each guide block of FIGS. 12A-12B may be straight-slotted and/or parallel with one another. However, these parallel bone pin holes may also be selectively spaced apart from each other to produce a desired compression force, distraction force, and/or neutral position (e.g., no force at all) between the first bone pin 921 and the second bone pin 922. In these embodiments, the bone pin holes may also include lead-in features around the bone pin holes (on an inferior surface of the block, a superior surface of block, or both, as previously described herein) to help facilitate insertion of the first and second bone pins into the bone pin holes.

In some embodiments, the first bone pin hole 1211 and the second bone pin hole 1212 of the compression block 1200 may be separated from each other by a first distance 1271 to compress the first bone portion and the second bone portion toward each other when the first bone pin 921 is anchored in the first bone portion and inserted through the first bone pin hole 1211, and the second bone pin 922 is anchored in the second bone portion and inserted through the second bone pin hole 1212.

In some embodiments, the first bone pin hole 1111 and the second bone pin hole 1112 of the distraction block 1100 may be separated from each other by a second distance 1172 to distract the first bone portion and the second bone portion away from each other when the first bone pin 921 is anchored in the first bone portion and inserted through the first bone pin hole 1111, and the second bone pin 922 is anchored in the second bone portion and inserted through the second bone pin hole 1112.

In some embodiments, the first bone pin hole 1011 and the second bone pin hole 1012 of the placement block 1000 may be separated from each other by a third distance 1073 to hold the first bone portion and the second bone portion in a neutral position with respect to each other when the first bone pin 921 is anchored in the first bone portion and inserted through the first bone pin hole 1011, and the second bone pin 922 is anchored in the second bone portion and inserted through the second bone pin hole 1012.

FIG. 14 shows a side view of a spade guide 1400, according to an embodiment of the present disclosure. The spade guide 1400 may generally include a spade portion 1410 at a distal end of the spade guide 1400, and a pin portion 1420 at a proximal end of the spade guide 1400.

In some embodiments, the spade portion 1410 may be inserted into a bone disunion (such as a bone fracture, a bone joint, etc.). In this manner, the pin portion 1420 of the spade guide 1400 may generally indicate a longitudinal direction or optimal fastener/implant trajectory relative to the bone disunion/joint based on the spade portion 1410 placed within the bone disunion.

In some embodiments, the spade portion 1410 may include a first substantially flat surface 1411, and a second substantially flat surface 1412 opposite the first substantially flat surface 1411.

In some embodiments, the first substantially flat surface 1411 of the spade portion 1410 may be configured to engage a first surface (e.g., see first surface 411 in FIG. 4) of the first bone portion within the bone disunion, and the second substantially flat surface 1412 of the spade portion 1410 may be configured to engage a second surface (e.g., see second surface 412 in FIG. 4) of the second bone portion within the bone disunion to indicate an orientation of the bone disunion via the pin portion 1420 of the spade guide 1400 projecting away from the bone disunion along the orientation of the bone disunion.

In some embodiments, the pin portion 1420 of the spade guide 1400 may be received through the placement block window 1040 of the placement block 1000 to guide initial placement of the first bone pin 921 and the second bone pin 922 into the bone portions via the first bone pin hole 1011 and the second bone pin hole 1012 of the placement block 1000. However, in other embodiments the windows of the distraction block 1100 and/or the compression block 1200 may be configured to receive one or more insert guides (not shown) similar in function to the one or more insert guides 950 shown in FIG. 10. In this manner, the pin portion 1420 of the spade guide 1400 may be utilized to orient the placement of the first bone pin 921 and the second bone pin 922 relative to the bone disunion in conjunction with the distraction block 1100 and/or the compression block 1200, omitting the placement block 1000.

In some embodiments, when the spade portion 1410 is inserted into the bone disunion between the first bone portion and the second bone portion, the pin portion 1420 projecting away from the bone disunion is inserted through the placement block window 1040, and the inferior surface 1060 of the placement block 1000 is placed adjacent the first bone portion and the second bone portion, the first bone pin hole 1011 may guide the first bone pin 921 into the first bone portion along a first trajectory defined by an orientation of the pin portion 1420 relative to the placement block window 1040, and the second bone pin hole 1012 may guide the second bone pin 922 into the second bone portion along a second trajectory defined by the orientation of the pin portion 1420 relative to the placement block window 1040. However, in other embodiments, when the spade portion 1410 is inserted into the bone disunion between the first bone portion and the second bone portion and the pin portion 1420 projecting away from the bone disunion is inserted through the one or more guide holes 970 formed through the one or more insert guides 950 placed within the central aperture 940 (e.g., see FIGS. 9A-10), the first pin hole 901 may guide the first bone pin 921 into the first bone portion along a first trajectory defined by an orientation of the pin portion 1420 of the spade guide 1400 relative to the one or more guide holes 970, and the parallel pin hole 911 may guide the second bone pin 922 into the second bone portion along a second trajectory defined by the orientation of the pin portion 1420 of the spade guide 1400 relative to the one or more guide holes 970.

In some embodiments, the placement block 1000 may then be removed from the first and second bone pins fixed/anchored to the first and second bone portions, the spade guide 1400 may be removed from the bone disunion/joint, and the distraction block 1100 may be placed over the first and second bone pins to distract the first bone portion 401 and the second bone portion 402 away from each other. In some embodiments, the further the distraction block 1100 is slid down the first and second bone pins toward the bone disunion/joint, the more distraction may be achieved.

In some embodiments, while the bone disunion/joint is held in the desired distracted position, bone surfaces on both sides of the bone disunion/joint may be accessed and prepared for fixation/fusion (e.g., rasping, filing, straightening/flattening, cleaning the bone surfaces on both sides of the bone disunion/joint, etc.). After this bone preparation step is complete, the distraction block 1100 may be slid back up and off the first and second bone pins.

In some embodiments, the compression block 1200 may then be placed over the first and second bone pins to compress the first bone portion 401 and the second bone portion 402 toward each other. In some embodiments, the further the compression block 1200 is slid down the first and second bone pins toward the bone disunion/joint, the more compression may be achieved.

In some embodiments, a locking feature (e.g., see locking feature 930) may be utilized to hold the compression block 1200 in place on the first and second bone pins to maintain a desired compression position.

In some embodiments, the desired compression position may be maintained while subsequent steps in the surgical procedure are performed (e.g., fixation steps including, but not limited to: drilling, tapping, inserting the implant through a window of the guide block, etc.). For example, FIG. 13 shows a guide tool 1300 placed within the compression block window 1240 of the compression block 1200 to guide a drilling tool, tapping tool, and/or insertion tool, etc., (not shown) with respect to the bone disunion/joint. The guide tool 1300 may be utilized to prepare a bone disunion to receive any of the implants/fasteners that are described or contemplated herein.

In some embodiments, the guide tool 1300 may be configured to guide a tapping tool (not shown) to form a tapped bone thread in the bone disunion/joint.

In some embodiments, the bone disunion/joint may be tapped with a tapping tool (not shown) having a full helical thread height to form a fully tapped bone thread in the bone disunion/joint.

In some embodiments, the bone disunion/joint may be tapped with a tapping tool (not shown) having a partial helical thread height to form a partially tapped bone thread in a first step, and the fastener/implant may include self-tapping or partial self-tapping features that can cut the rest of the helical thread height in the bone disunion/joint, thereby allowing the fastener/implant to secure to virgin-cut bone. In some embodiments, the fastener/implant may include self-tapping features that can cut the entire helical thread height in the bone disunion/joint, thereby omitting the need for any tapping tool.

In some embodiments, the guide tool 1300 may include a first offset drill guide 1310 and a second offset drill guide 1320. The first offset drill guide 1310 may be configured to guide a drill tool (not shown) to form a first pilot hole in the first bone portion to receive a first leg of a bone staple (e.g., see FIG. 6A), and the second offset drill guide 1320 may be configured to guide the drill tool to form a second pilot hole in the second bone portion to receive a second leg of the bone staple. Moreover, a central bore 1330 of the guide tool 1300 may be utilized to guide the drill tool (with or without an additional sleeve that may be placed within the central bore 1330) to form a pilot hole in the bone disunion to receive any fastener/implant disclosed or contemplated herein (e.g., see fastener 300 shown in FIGS. 6A, 4, etc.).

Figure 22:
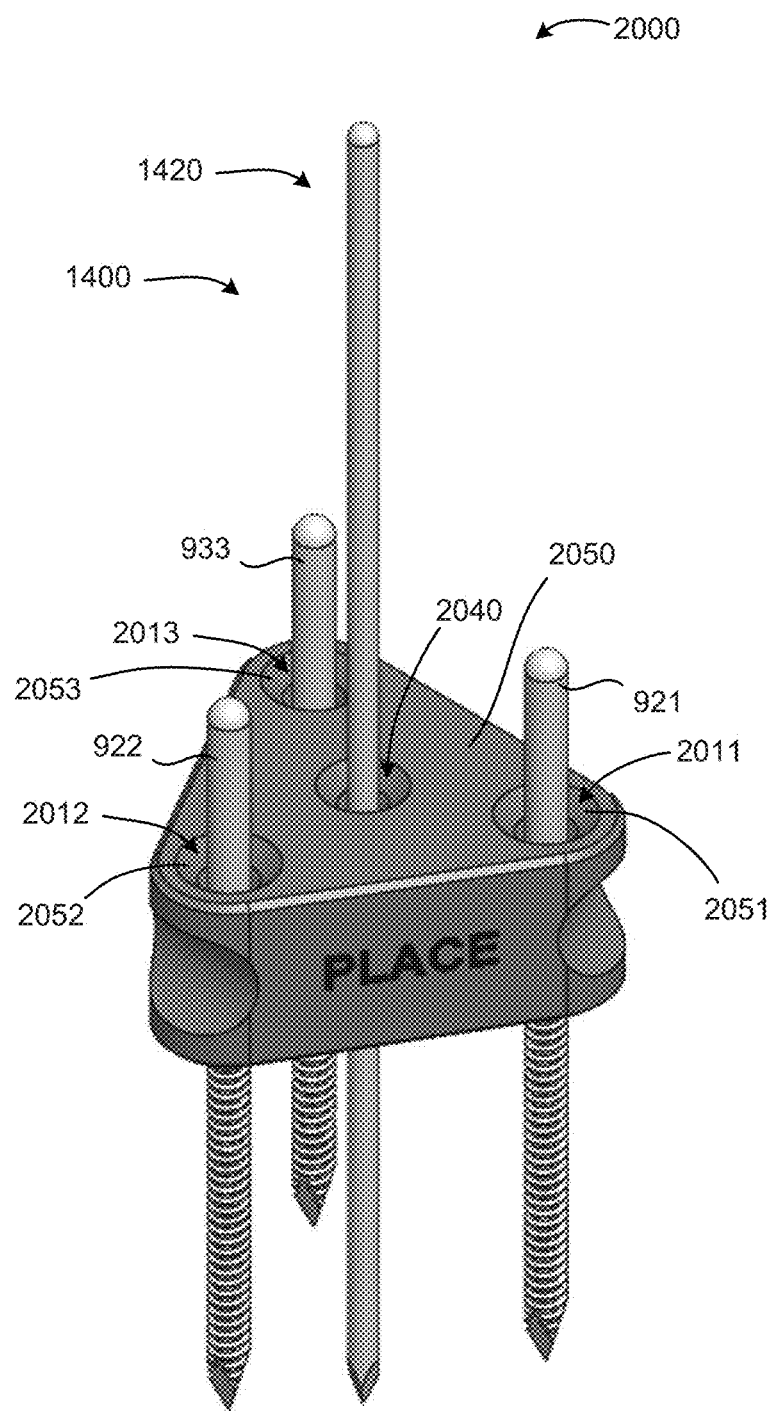
FIG. 22 illustrates a perspective top view of a placement block, according to another embodiment of the present disclosure.
Figure 23:
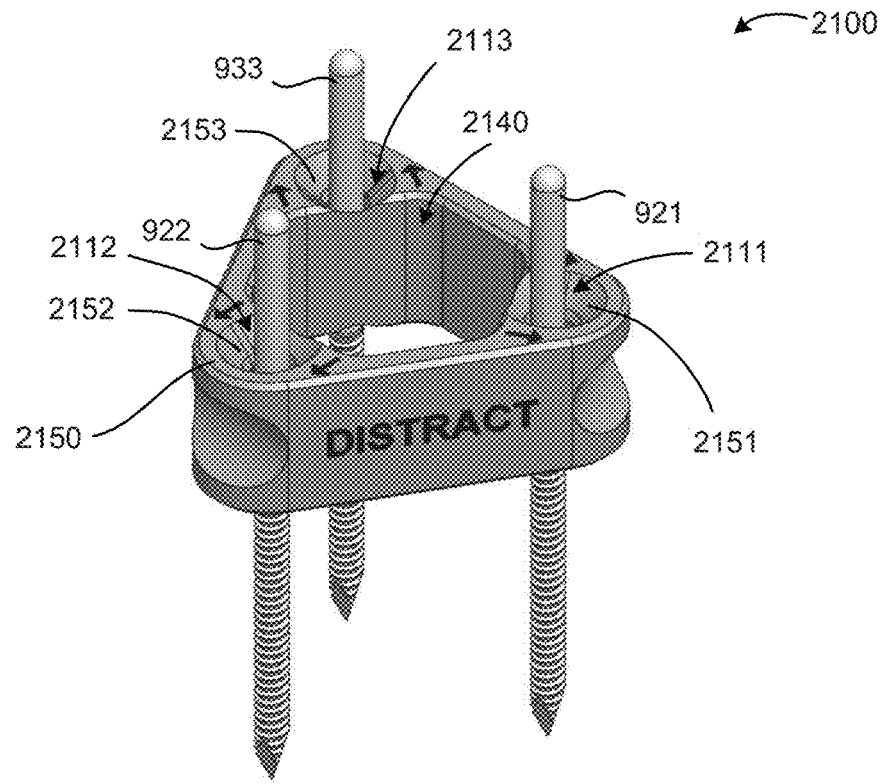
FIG. 23 illustrates a perspective top view of a distraction block, according to another embodiment of the present disclosure.
Figure 24:
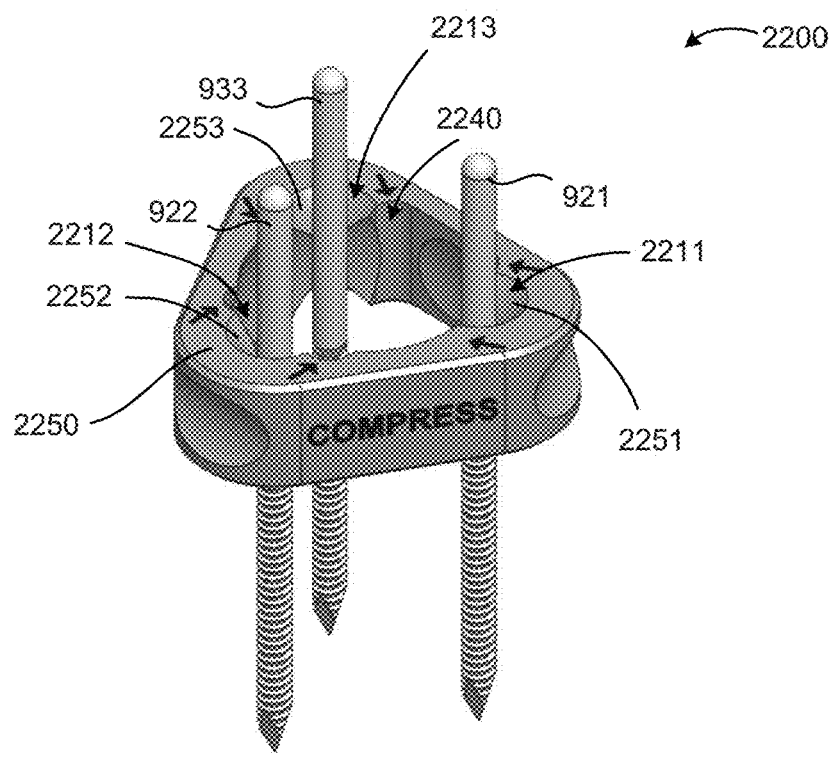
FIG. 24 illustrates a perspective top view of a compression block, according to another embodiment of the present disclosure.

FIGS. 22-24 illustrate various components for one or more bone disunion instrument systems, according to other embodiments of the present disclosure. Specifically, FIG. 22 shows a perspective top view of a placement block 2000; FIG. 23 shows a perspective top view of a distraction block 2100; and FIG. 24 shows a perspective top view of a compression block 2200, according to embodiments of the present disclosure.

The placement block 2000, the distraction block 2100, and/or the compression block 2200 may also be referred to herein as a block, a guide block, or an implant insertion block.

The placement block 2000, distraction block 2100, and compression block 1200 may be configured to aid the preparation and fusion of one or more bone disunions that may be formed between one or more bone portions during a surgical procedure by utilizing each block in combination one or more bone pins (e.g., the first bone pin 921, the second bone pin 922, a third bone pin 933, etc.) to place the first bone pin 921, the second bone pin 922, the third bone pin 933, etc., on the one or more bone portions proximate the one or more bone disunions, distract the one or more bone disunions during surface preparation, then compress the one or more bone disunions (and/or hold the one or more bone disunions under compression) to install one or more suitable implants (e.g., any of the implants described or contemplated herein) into/about the one or more bone disunions in order to stabilize/fixate/fuse the one or more bone disunions via the one or more implants, similar to other procedures already described herein.

In some embodiments, the placement block 2000 may include a first bone pin hole 2011, a second bone pin hole 2012, a third bone pin hole 2013, a placement block hole or placement block window 2040, a superior surface 2050, an inferior surface (not shown), a first inferior lead-in feature (not shown), a second inferior lead-in feature (not shown), a third inferior lead-in feature (not shown), a first superior lead-in feature 2051, a second superior lead-in feature 2052, and a third superior lead-in feature 2053.

In some embodiments, the distraction block 2100 may include a first bone pin hole 2111, a second bone pin hole 2112, a third bone pin hole 2113, a distraction block hole or distraction block window 2140, a superior surface 2150, an inferior surface (not shown), a first inferior lead-in feature (not shown), a second inferior lead-in feature (not shown), a third inferior lead-in feature (not shown), a first superior lead-in feature 2151, a second superior lead-in feature 2152, and a third superior lead-in feature 2153.

In some embodiments, the compression block 2200 may include a first bone pin hole 2211, a second bone pin hole 2212, a third bone pin hole 2213, a compression block hole or compression block window 2240, a superior surface 2250, an inferior surface (not shown), a first inferior lead-in feature (not shown), a second inferior lead-in feature (not shown), a third inferior lead-in feature (not shown), a first superior lead-in feature 2251, a second superior lead-in feature 2252, and a third superior lead-in feature 2253.

However, it will also be understood that in other embodiments, the placement block 2000, the distraction block 2100, and/or the compression block 2200 may be further modified to include more than three bone pin holes (e.g., four bone pin holes, five bone pin holes, etc.) in order to receive more than three bone pins to aid the preparation and fusion/stabilization of one or more bone disunions formed between one or more bone portions, similar to other surgical procedures described herein.

In some embodiments, the compression block window 2240 and one or more of the first bone pin hole 2211, the second bone pin hole 2212, and the third bone pin hole 2213 may be joined together, as shown in FIG. 24. However, it will also be understood that the windows of any guide block disclosed or contemplated herein may assume any shape, size, configuration, etc. Moreover, the windows of any guide block disclosed or contemplated herein may be fully or partially bounded by one or more sidewalls of the guide block.

In some embodiments, each of the placement block 2000, the distraction block 2100, and the compression block 2200 may (or may not) include a locking feature (not shown), as previously described herein with respect to FIGS. 9A-10. Moreover, it will also be understood that the placement block 2000, the distraction block 2100, and/or the compression block 2200 may (or may not) include any other feature (or functionality) of any guide block that is disclosed or contemplated herein.

Figure 15A:
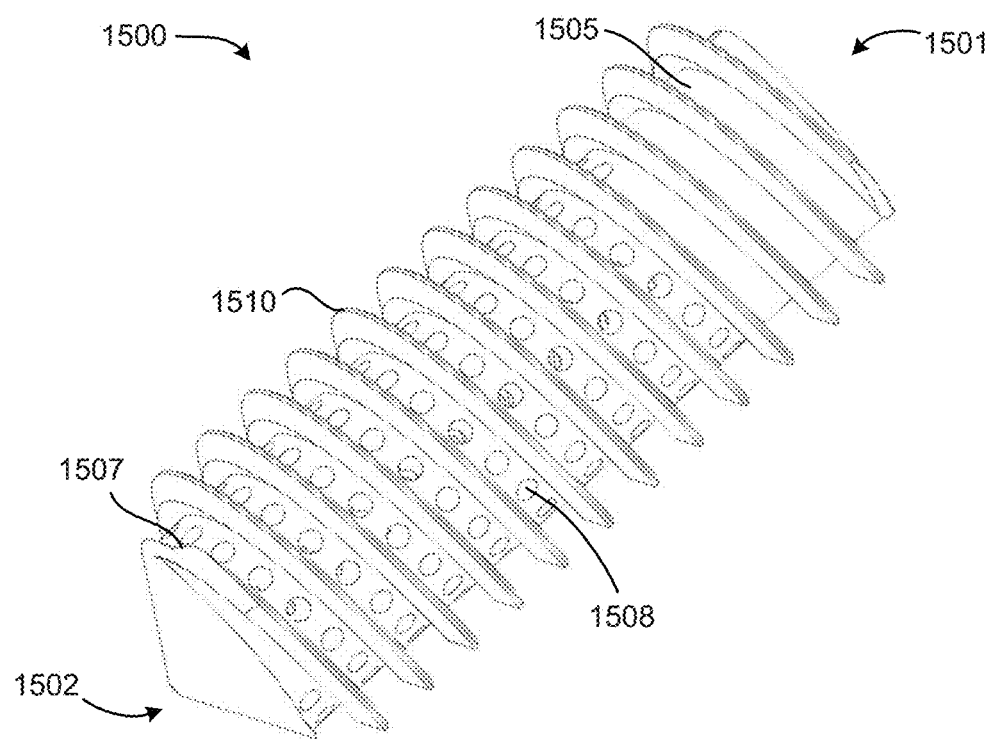
FIG. 15A illustrates a perspective side view of an intervertebral fastener, according to an embodiment of the present disclosure.
Figure 15B:
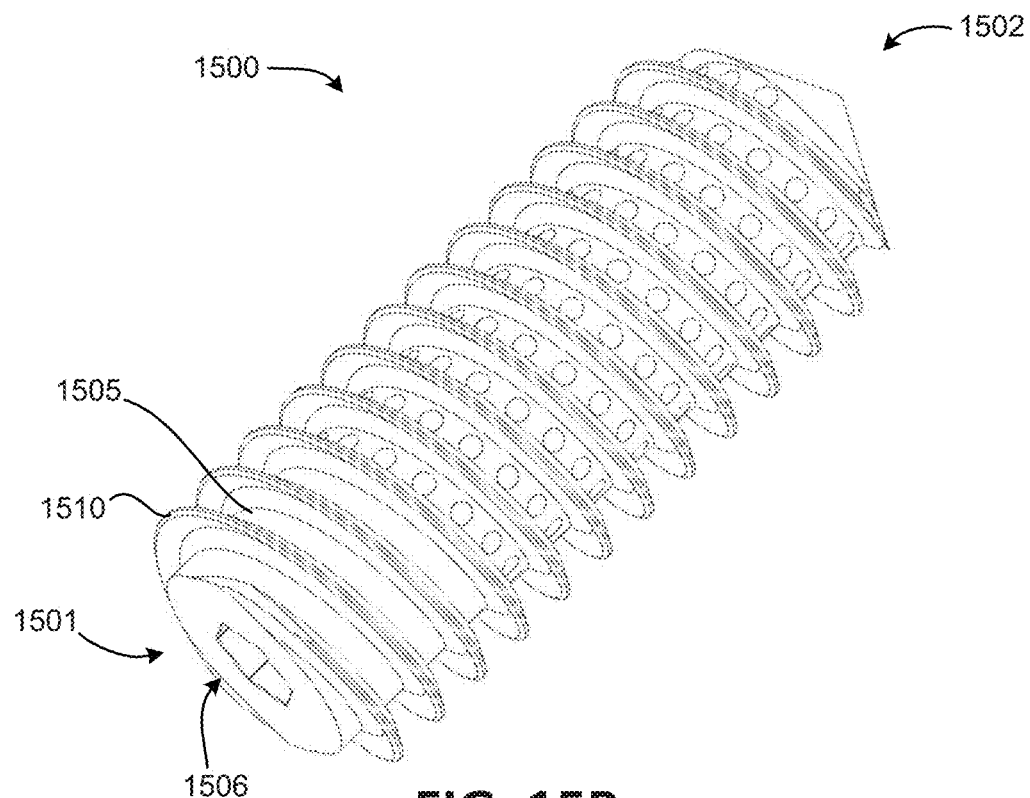
FIG. 15B illustrates another perspective side view of the intervertebral fastener of FIG. 15A.
Figure 15C:
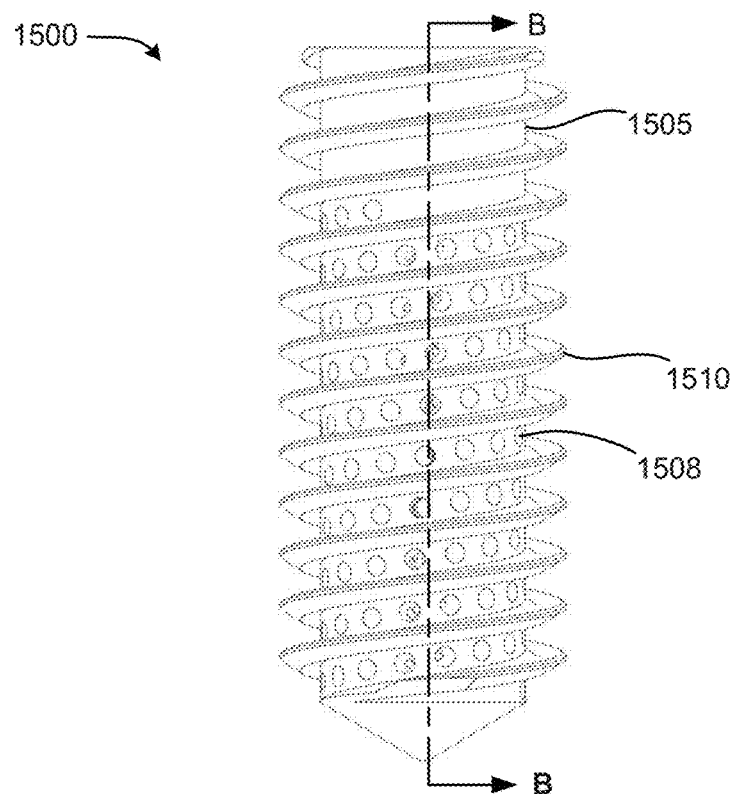
FIG. 15C illustrates a side view of the intervertebral fastener of FIG. 15A.
Figure 15D:
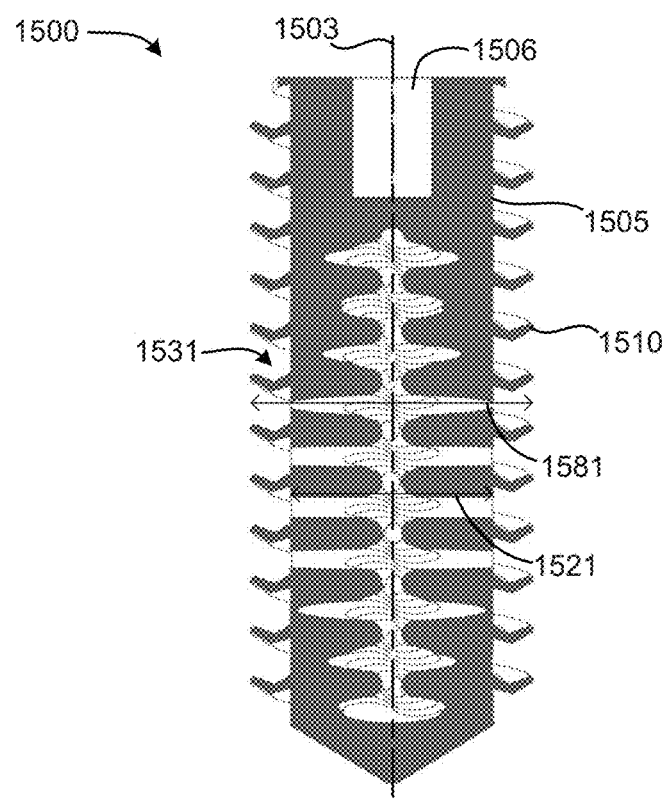
FIG. 15D illustrates a cross-sectional side view of the intervertebral fastener of FIG. 15A, taken along the line B-B.

FIGS. 15A-15D illustrate various views of a fastener, implant, intervertebral fastener/implant, or bone implant 1500, according to an embodiment of the present disclosure. Specifically, FIG. 15A is a perspective view of the bone implant 1500, FIG. 15B is another perspective view of the bone implant 1500, FIG. 15C is a side view of the bone implant 1500, and FIG. 15D is a cross-sectional side view of the bone implant 1500 taken along the line B-B in FIG. 15C.

The bone implant 1500 may generally include a shaft 1505 having a proximal end 1501, a distal end 1502, a longitudinal axis 1503, at least one helical thread 1510 disposed about the shaft 1505, and a torque connection interface 1506 formed in/on the proximal end 1501 of the shaft 1505.

In some embodiments, the distal end 1502 of the shaft 1505 may comprise a pointed or sharp tip.

In some embodiments, the shaft 1505 may include a central longitudinal passageway or cannulation configured to receive a pin or K-wire (not shown) therethrough.

In some embodiments, the shaft 1505 may include one or more fenestrations, pores, lattice-like structures, passages 1508, etc., configured to receive a bone cement, bone graft material, bone augment material, etc., therein. The passages 1508 may open on either side of the bone implant 1500 so that bone can grow through the shaft 1505, transverse to the axis of the shaft 1505, to permit bone to grow between bones on either side of the bone implant 1500, transversely through the shaft 1505.

In some embodiments, the bone implant 1500 may be configured to couple with additional spinal fixation devices, such as pedicle screws, rods, spikes, hooks, spacers, etc., (not shown) to form one or more spinal fixation systems.

In some embodiments, the shaft 1505 and/or the at least one helical thread 1510 may comprise one or more cutting flutes or self-tapping features 1507.

In some embodiments, the shaft 1505 may have a minor diameter 1521 generally defined by the shape of the shaft 1505, and a major diameter 1581 generally defined by the shape of the at least one helical thread 1510 disposed about the shaft 1505.

In some embodiments, at least one of the minor diameter 1521 and the major diameter 1581 may be constant along at least a portion of the shaft 1505.

In some embodiments, at least one of the minor diameter 1521 and the major diameter 1581 may vary along at least a portion of the shaft 1505.

In some embodiments, the minor diameter 1521 defined by the shape of the shaft 1505 may be generally constant moving from the proximal end 1501 of the shaft 1505 toward the distal end 1502 of the shaft 1505.

In some embodiments, the minor diameter 1521 defined by the shape of the shaft 1505 may comprise a cylindrical shape.

In some embodiments, at least a portion of the shaft 1505 may comprise at least one of: a cylindrical shape, a conical shape, a rectangular shape, straight sides, angled sides, conical sides, etc., or any combinations thereof.

In some embodiments, the major diameter 1581 defined by the shape of the at least one helical thread 1510 disposed about the shaft 1505 may comprise a cylindrical shape.

In some embodiments, the major diameter 1581 defined by the shape of the at least one helical thread 1510 disposed about the shaft 1505 may generally decrease moving from the proximal end 1501 of the shaft 1505 toward the distal end 1502 of the shaft 1505.

In some embodiments, a ratio of the major diameter 1581 to the minor diameter 1521 may be less than 1.50.

In some embodiments, a ratio of the major diameter 1581 to the minor diameter 1521 may be less than 1.25.

In some embodiments, a ratio of the major diameter 1581 to the minor diameter 1521 may be less than 1.10.

In some embodiments, a ratio of the major diameter 1581 to the minor diameter 1521 may be less than 1.05.

In some embodiments, the at least one helical thread 1510 may include at least one concave undercut surface 1531.

In some embodiments, the at least one concave undercut surface 1531 may be angled towards one of the proximal end 1501 and the distal end 1502 of the shaft 1505.

However, it will also be understood that the bone implant 1500 may include any thread configuration, feature, or morphology described or contemplated herein with respect to any fastener/implant to achieve optimal fixation within a given bone/tissue. For example, in some embodiments the at least one helical thread 1510 may comprise standard or inverted threading, a "dual start" thread configuration, crescent shapes, etc.

In some embodiments, when the intervertebral implant or bone implant 1500 is implanted within an intervertebral space between a superior vertebral body and an inferior vertebral body, the at least one concave undercut surface 1531 may engage the superior vertebral body and the inferior vertebral body, and the at least one concave undercut surface 1531 may be shaped to resist at least one force transmitted between the superior vertebral body and the inferior vertebral body to stabilize the intervertebral space.

In some embodiments, when the intervertebral implant or bone implant 1500 is implanted within a sacroiliac joint between a sacrum and an ilium of a pelvis, the at least one concave undercut surface 1531 may engage the sacrum and ilium bones, and the at least one concave undercut surface 1531 may be shaped to resist at least one force transmitted between the sacrum and the ilium to stabilize the sacroiliac joint.

In some embodiments, the intervertebral implant or bone implant 1500 may be implanted within an intervertebral space and/or a sacroiliac joint from a posterior direction. However, it will be understood that any of the implants described or contemplated herein may be implanted within any joint or bone from an anterior direction, a posterior direction, a lateral direction, a medial direction, an inferior direction, a superior direction, etc., and/or any combination of directions thereof (e.g., a postero-lateral direction, etc.).

Figure 16A:
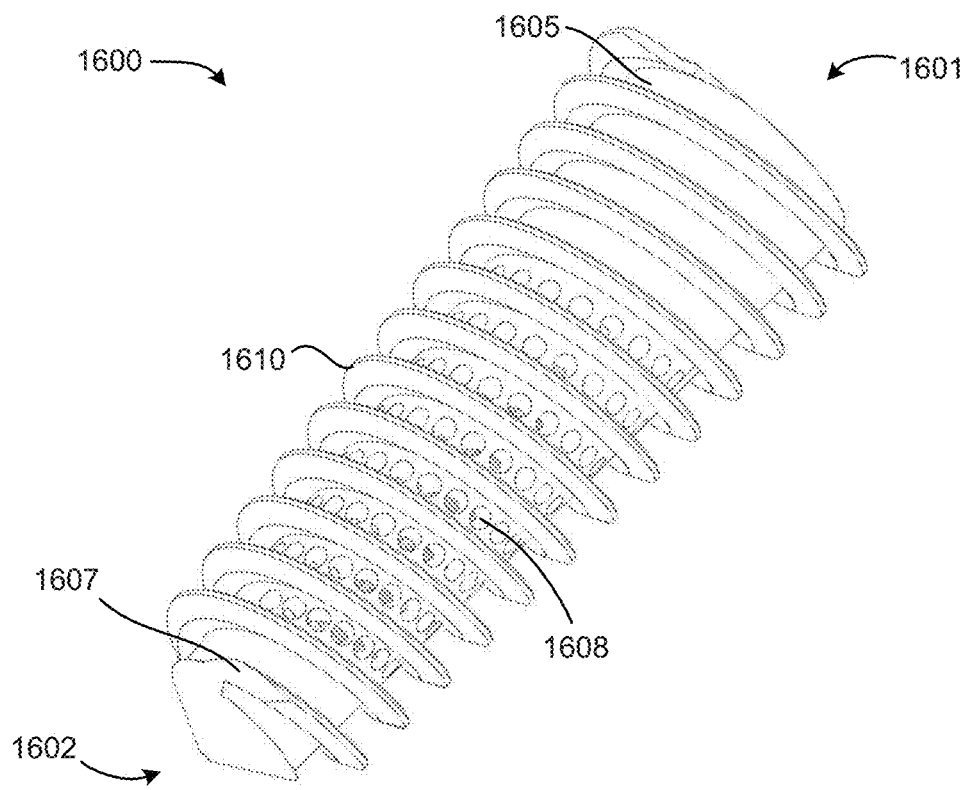
FIG. 16A illustrates a perspective side view of an intervertebral fastener, according to another embodiment of the present disclosure.
Figure 16B:
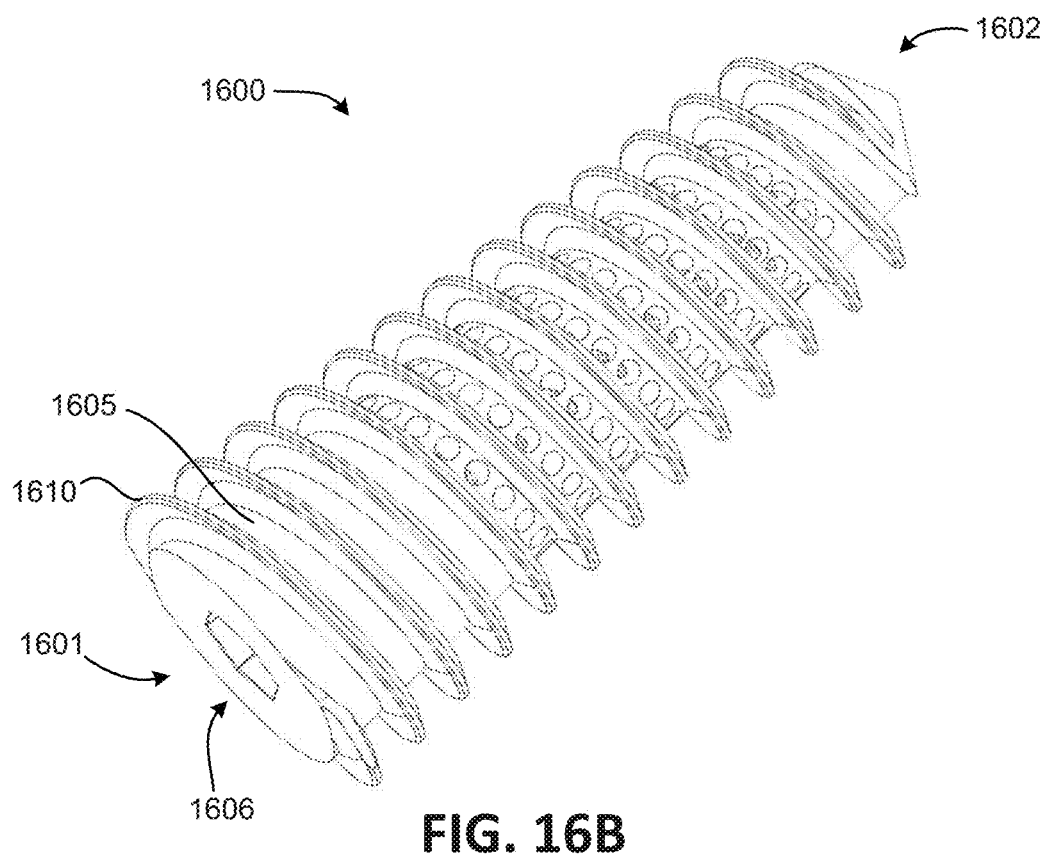
FIG. 16B illustrates another perspective side view of the intervertebral fastener of FIG. 16A.
Figure 16C:
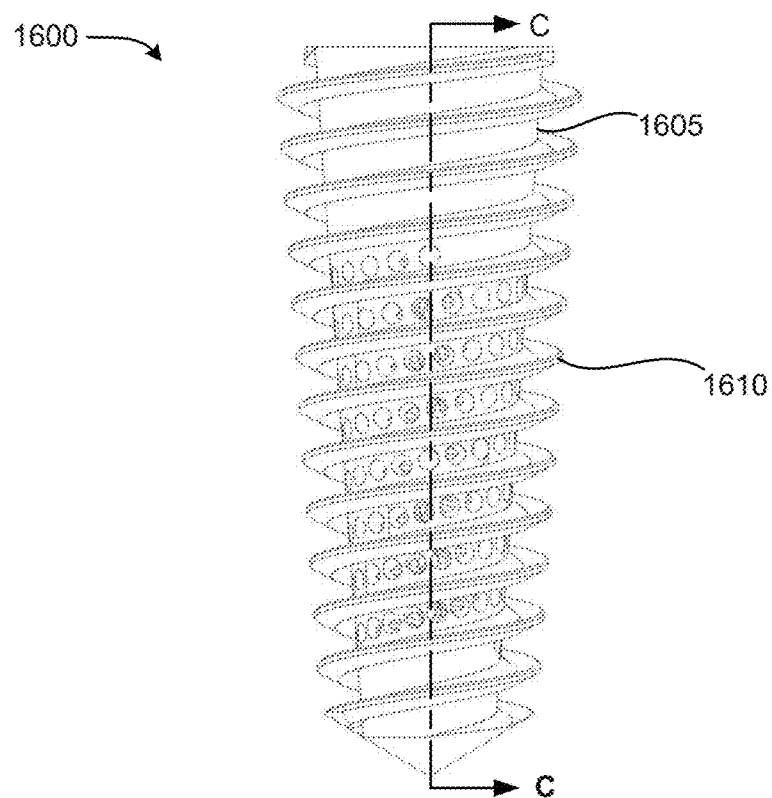
FIG. 16C illustrates a side view of the intervertebral fastener of FIG. 16A.
Figure 16D:
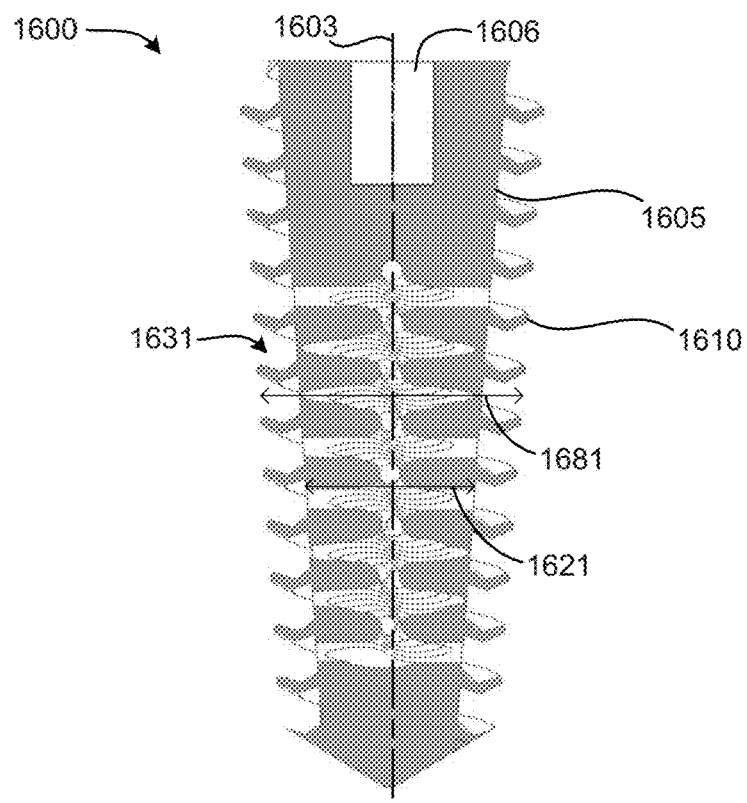
FIG. 16D illustrates a cross-sectional side view of the intervertebral fastener of FIG. 16A, taken along the line C-C.

FIGS. 16A-16D illustrate various views of a fastener, implant, intervertebral fastener/implant, or bone implant 1600, according to another embodiment of the present disclosure. Specifically, FIG. 16A is a perspective view of the bone implant 1600, FIG. 16B is another perspective view of the bone implant 1600, FIG. 16C is a side view of the bone implant 1600, and FIG. 16D is a cross-sectional side view of the bone implant 1600 taken along the line C-C in FIG. 16C.

The bone implant 1600 may generally include a tapered shaft 1605 having a proximal end 1601, a distal end 1602, a longitudinal axis 1603, at least one tapered helical thread 1610 disposed about the tapered shaft 1605, and a torque connection interface 1606 formed in/on the proximal end 1601 of the tapered shaft 1605.

In some embodiments, the distal end 1602 of the tapered shaft 1605 may comprise a pointed or sharp tip.

In some embodiments, the tapered shaft 1605 may include a central longitudinal passageway or cannulation configured to receive a pin or K-wire (not shown) therethrough.

In some embodiments, the tapered shaft 1605 may include one or more fenestrations, pores, lattice-like structures, passages 1608, etc., configured to receive a bone cement, bone graft material, bone augment material, etc., therein.

In some embodiments, the bone implant 1600 may be configured to couple with additional spinal fixation devices, such as pedicle screws, rods, spikes, hooks, spacers, etc., (not shown) to form one or more spinal fixation systems.

In some embodiments, the tapered shaft 1605 and/or the at least one tapered helical thread 1610 may comprise one or more cutting flutes or self-tapping features 1607.

In some embodiments, the tapered shaft 1605 may have a continuously variable minor diameter or minor diameter 1621 generally defined by the shape of the tapered shaft 1605, and a continuously variable major diameter or major diameter 1681 generally defined by the shape of the at least one tapered helical thread 1610 disposed about the tapered shaft 1605.

In some embodiments, at least one of the minor diameter 1621 and the major diameter 1681 may vary along at least a portion of the tapered shaft 1605.

In some embodiments, at least one of the minor diameter 1621 and the major diameter 1681 may be constant along at least a portion of the tapered shaft 1605.

In some embodiments, the minor diameter 1621 defined by the shape of the tapered shaft 1605 may generally decrease moving from the proximal end 1601 of the tapered shaft 1605 toward the distal end 1602 of the tapered shaft 1605.

In some embodiments, the minor diameter 1621 defined by the shape of the tapered shaft 1605 may comprise an at least partially conical shape.

In some embodiments, at least a portion of the tapered shaft 1605 may comprise at least one of: a conical shape, a cylindrical shape, a rectangular shape, straight sides, angled sides, conical sides, etc., or any combinations thereof.

In some embodiments, the major diameter 1681 defined by the shape of the at least one tapered helical thread 1610 disposed about the tapered shaft 1605 may comprise an at least partially conical shape.

In some embodiments, the major diameter 1681 defined by the shape of the at least one tapered helical thread 1610 disposed about the tapered shaft 1605 may generally decrease moving from the proximal end 1601 of the tapered shaft 1605 toward the distal end 1602 of the tapered shaft 1605.

In some embodiments, a ratio of the major diameter 1681 to the minor diameter 1621 may be less than 1.50.

In some embodiments, a ratio of the major diameter 1681 to the minor diameter 1621 may be less than 1.25.

In some embodiments, a ratio of the major diameter 1681 to the minor diameter 1621 may be less than 1.10.

In some embodiments, a ratio of the major diameter 1681 to the minor diameter 1621 may be less than 1.05.

In some embodiments, the at least one tapered helical thread 1610 may include at least one concave undercut surface 1631.

In some embodiments, the at least one concave undercut surface 1631 may be angled towards one of the proximal end 1601 and the distal end 1602 of the tapered shaft 1605.

However, it will also be understood that the bone implant 1600 may include any thread configuration, feature, or morphology described or contemplated herein with respect to any fastener/implant to achieve optimal fixation within a given bone/tissue. For example, in some embodiments the at least one tapered helical thread 1610 may comprise standard or inverted threading, a "dual start" thread configuration, crescent shapes, etc.

In some embodiments, when the intervertebral implant or bone implant 1600 is implanted within an intervertebral space between a superior vertebral body and an inferior vertebral body, the at least one concave undercut surface 1631 may engage the superior vertebral body and the inferior vertebral body, and the at least one concave undercut surface 1631 may be shaped to resist at least one force transmitted between the superior vertebral body and the inferior vertebral body to stabilize the intervertebral space.

In some embodiments, when the intervertebral implant or bone implant 1600 is implanted within a sacroiliac joint between a sacrum and an ilium of a pelvis, the at least one concave undercut surface 1631 may engage the sacrum and ilium bones, and the at least one concave undercut surface 1631 may be shaped to resist at least one force transmitted between the sacrum and the ilium to stabilize the sacroiliac joint.

In some embodiments, the intervertebral implant or bone implant 1600 may be implanted within an intervertebral space and/or a sacroiliac joint from a posterior direction. However, it will be understood that any of the implants described or contemplated herein may be implanted within any joint or bone from an anterior direction, a posterior direction, a lateral direction, a medial direction, an inferior direction, a superior direction, etc., and/or any combination of directions thereof (e.g., a postero-lateral direction, etc.).

Figure 17:
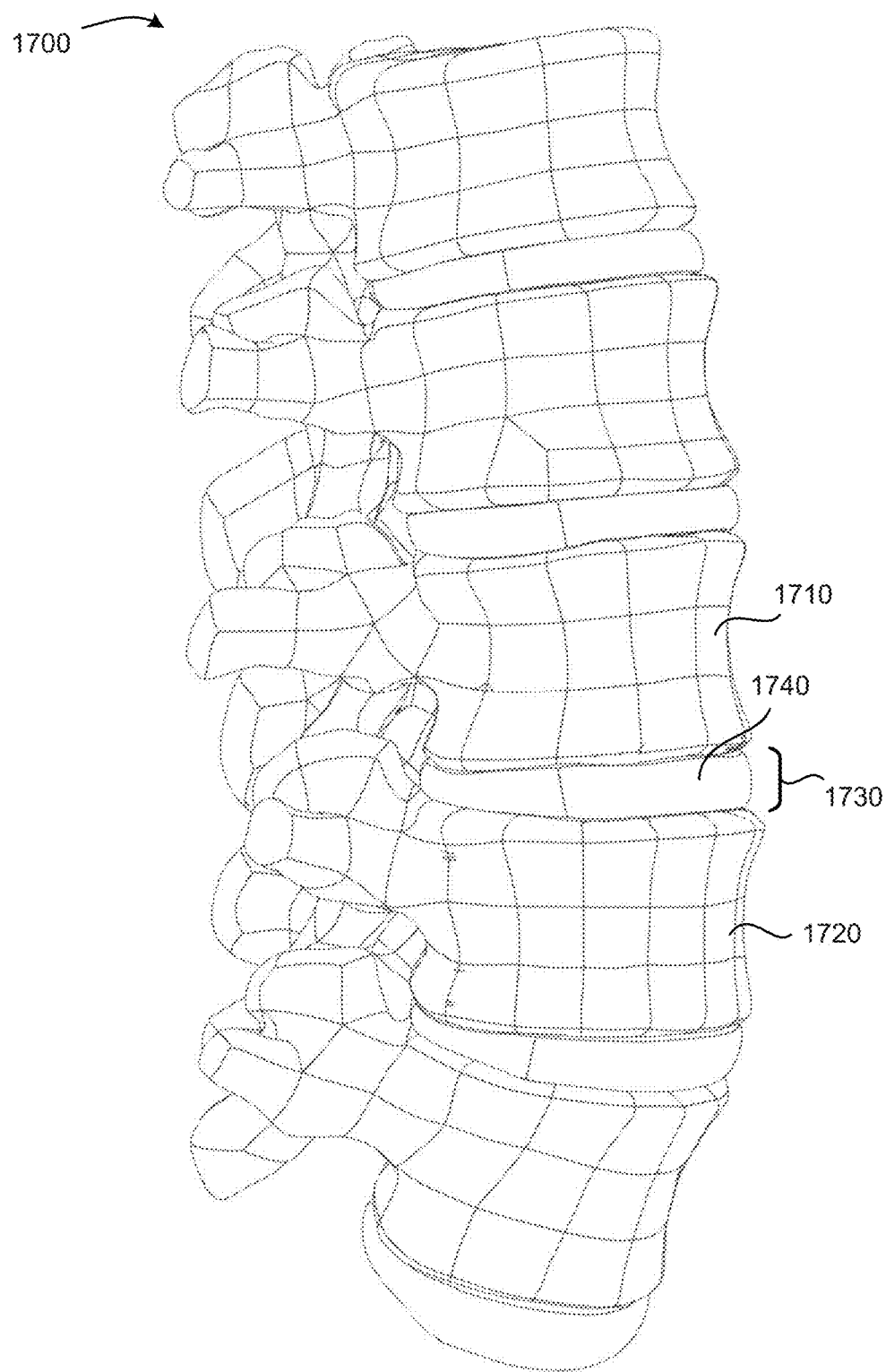
FIG. 17 illustrates a perspective side view of a vertebral column, prior to a surgical procedure.
Figure 18:
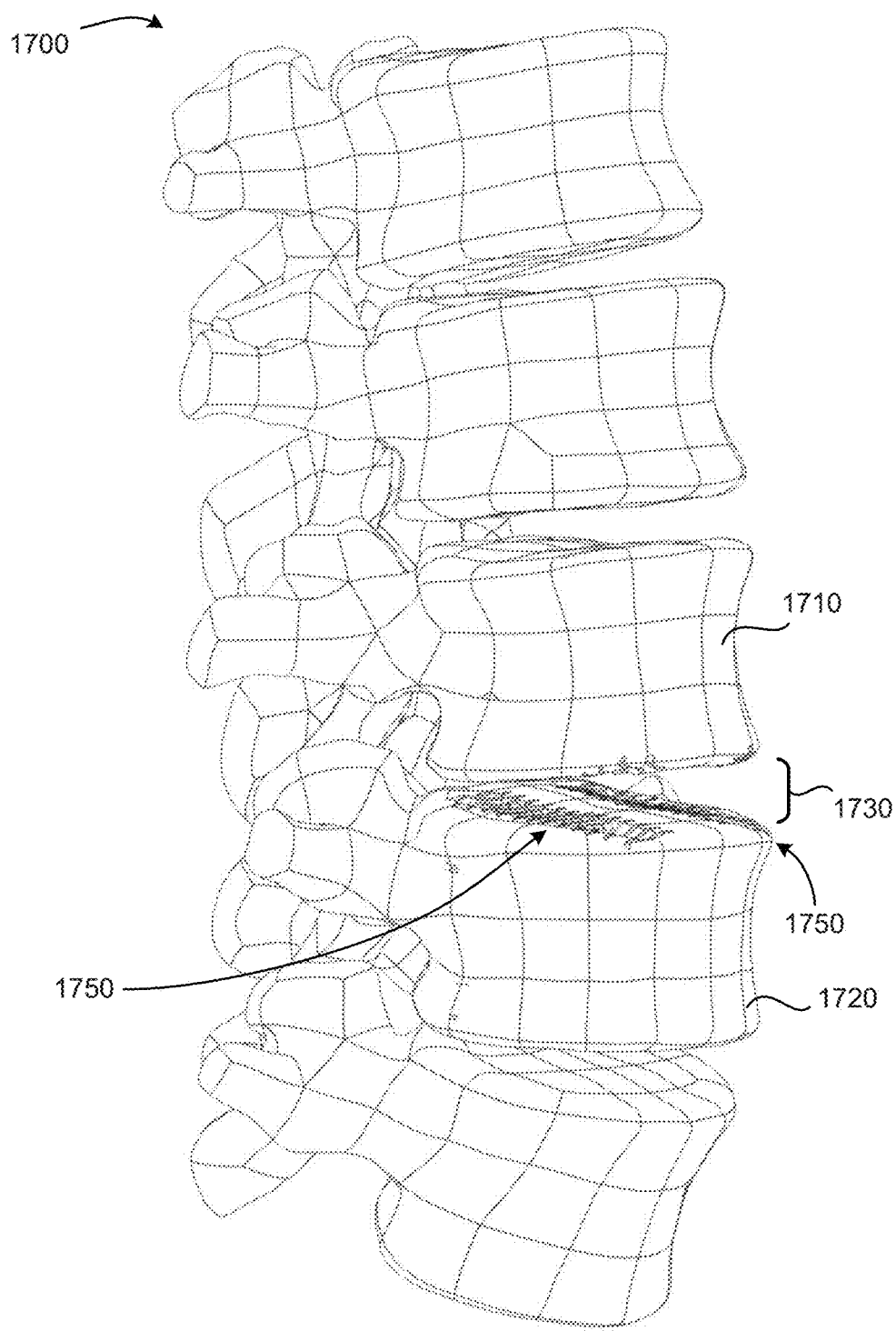
FIG. 18 illustrates a perspective side view of the vertebral column of FIG. 17 with at least a portion of an intervertebral disc removed and one or more tapped bone threads formed in a superior vertebral body and an inferior vertebral body.
Figure 19:
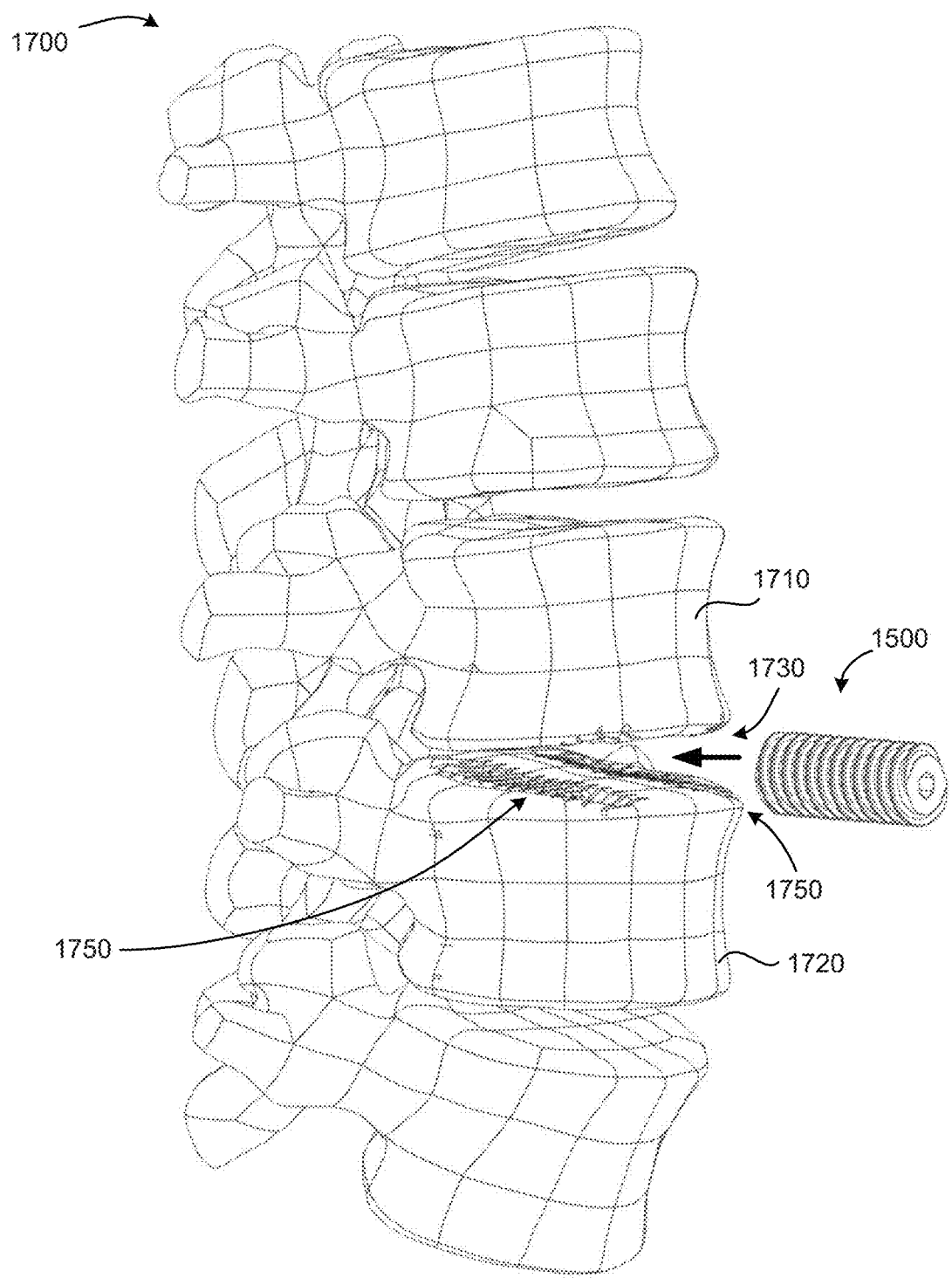
FIG. 19 illustrates the vertebral column of FIG. 18 with the intervertebral fastener of FIG. 15A placed adjacent the prepared intervertebral space, prior to insertion.
Figure 20:
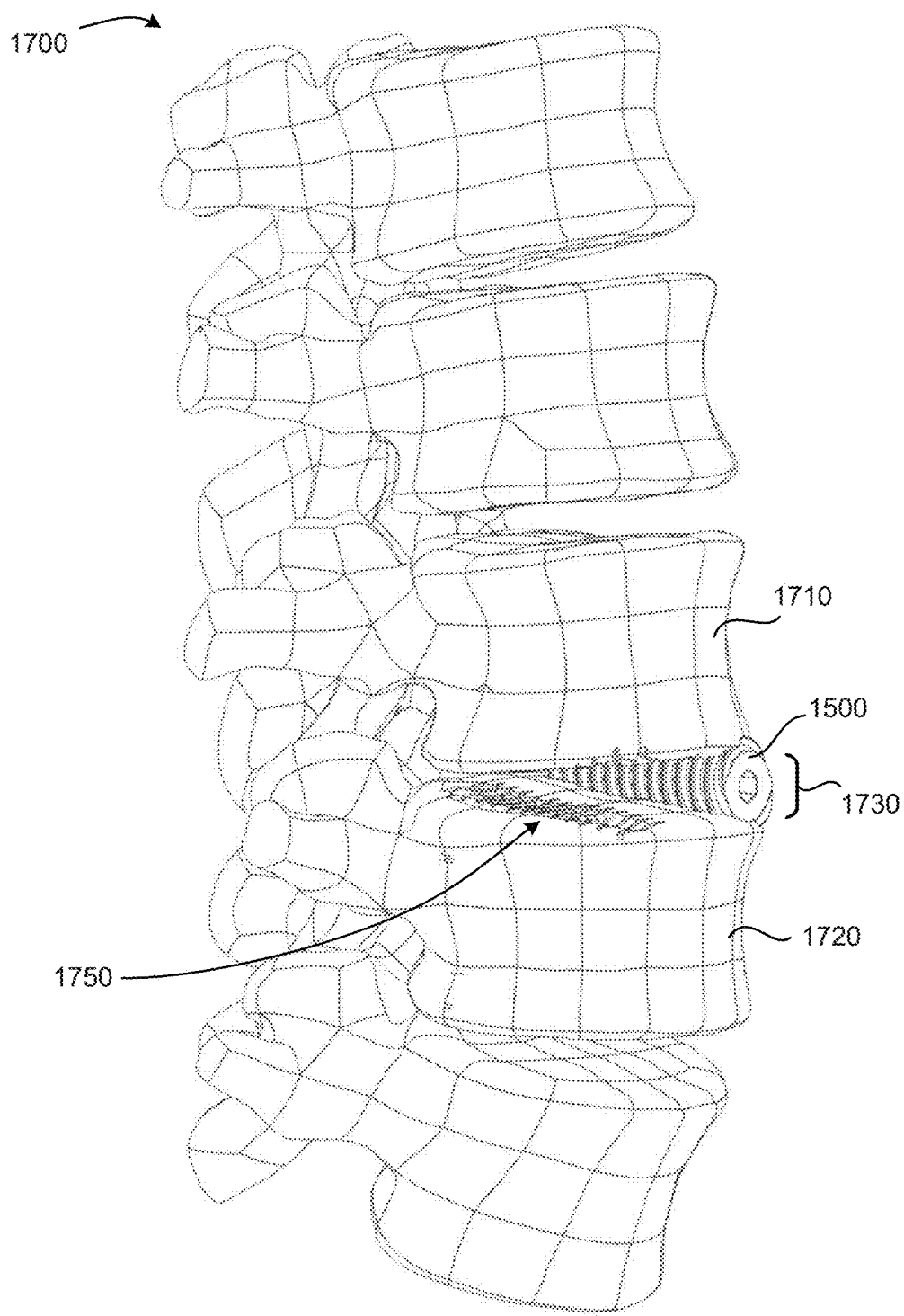
FIG. 20 illustrates the vertebral column of FIG. 19 with the intervertebral fastener inserted into the prepared intervertebral space.
Figure 21:
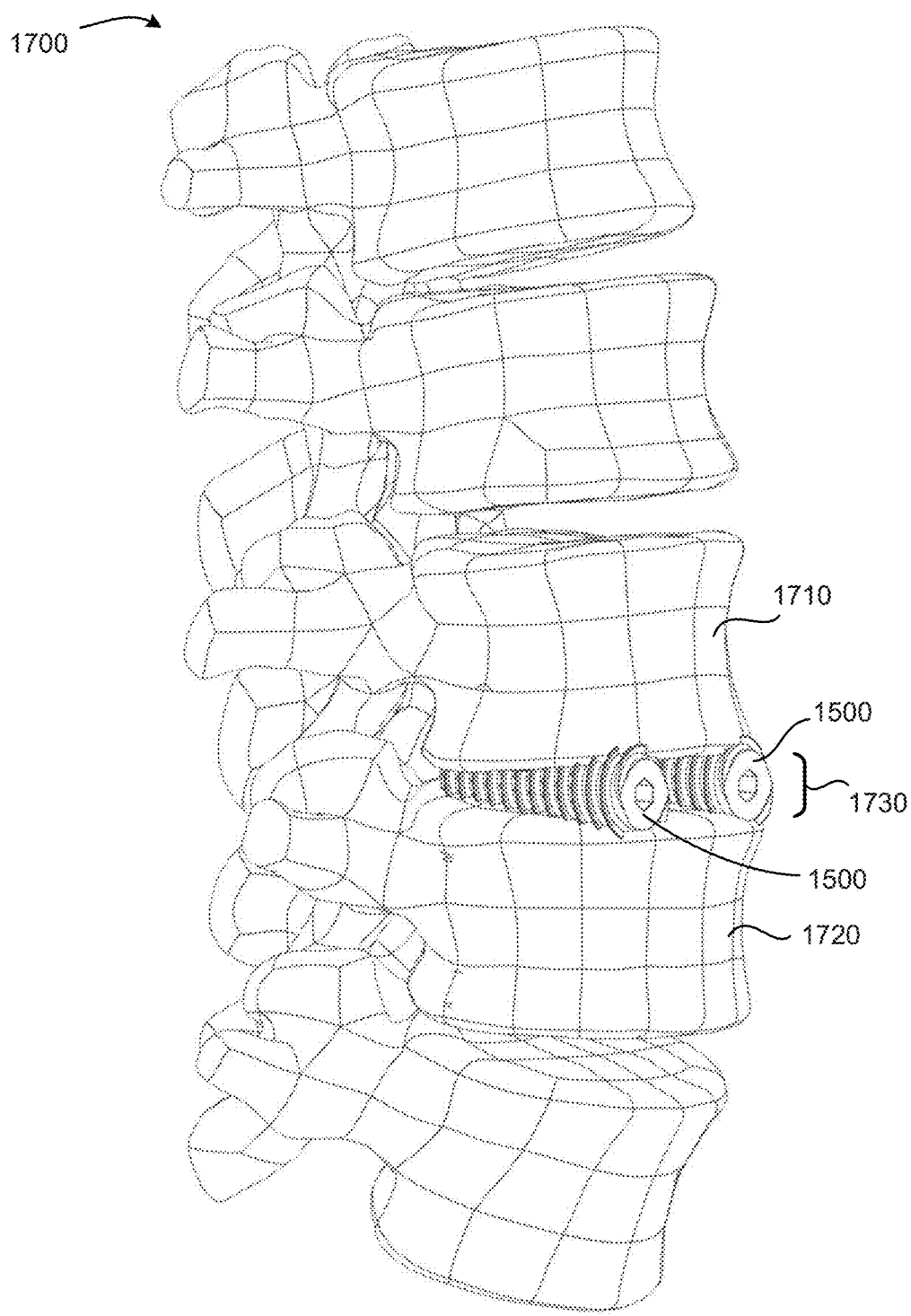
FIG. 21 illustrates the vertebral column of FIG. 20 with a second intervertebral fastener inserted into the prepared intervertebral space, adjacent the first intervertebral fastener.

FIGS. 17-21 illustrate a procedure for implanting an intervertebral implant within an intervertebral space 1730 between a superior vertebral body 1710 and an inferior vertebral body 1720. Specifically, FIG. 17 shows a vertebral column 1700, prior to the procedure; FIG. 18 shows the vertebral column 1700 of FIG. 17 with at least a portion of an intervertebral disc 1740 removed and at least one tapped bone thread 1750 formed in at least one of the superior vertebral body 1710 and the inferior vertebral body 1720; FIG. 19 illustrates the vertebral column 1700 of FIG. 18 with the intervertebral fastener or bone implant 1500 of FIG. 15A placed adjacent the prepared intervertebral space 1730, prior to insertion; FIG. 20 illustrates the vertebral column 1700 of FIG. 19 with the bone implant 1500 inserted into the prepared intervertebral space 1730; and FIG. 21 illustrates the vertebral column 1700 of FIG. 20 with a second intervertebral fastener or bone implant 1500 inserted into the prepared intervertebral space 1730, adjacent the first intervertebral fastener or bone implant 1500.

In some embodiments, a surgical procedure or method for implanting an intervertebral implant (e.g., such as the bone implant 1500 of FIG. 15A, or the bone implant 1600 of 16A) within the intervertebral space 1730 between the superior vertebral body 1710 and the inferior vertebral body 1720 may include: placing a distal end of a shaft of the intervertebral implant adjacent the intervertebral space 1730; engaging a concave undercut surface of a helical thread disposed about the shaft of the intervertebral implant with the superior vertebral body 1710 and the inferior vertebral body 1720; and rotating the intervertebral implant in a first rotational direction (e.g., clockwise or counter-clockwise) to insert the intervertebral implant within the intervertebral space 1730.

In some embodiments of the method, when the intervertebral implant is implanted within the intervertebral space 1730, the concave undercut surface may be shaped to resist at least one force transmitted between the superior vertebral body 1710 and the inferior vertebral body 1720 to stabilize the intervertebral space 1730.

In some embodiments, the method may also include preparing the intervertebral space 1730 to receive the intervertebral implant. Preparing the intervertebral space 1730 may include at least one of: removing at least a portion of the intervertebral disc 1740 intermediate the superior vertebral body 1710 and the inferior vertebral body 1720; distracting the superior vertebral body 1710 and the inferior vertebral body 1720 away from each other; compressing the superior vertebral body 1710 and the inferior vertebral body 1720 toward each other; drilling, reaming, broaching, etc., the superior vertebral body 1710 and/or the inferior vertebral body 1720.

In some embodiments, the method may also include forming or pre-tapping the at least one tapped bone thread 1750 in at least one of a superior vertebral endplate of the superior vertebral body 1710 and an inferior vertebral endplate of the inferior vertebral body 1720.

In some embodiments, the intervertebral implant may include self-tapping features and the method may or may not omit the step of forming or pre-tapping the at least one tapped bone thread 1750 in at least one of a superior vertebral endplate of the superior vertebral body 1710 and an inferior vertebral endplate of the inferior vertebral body 1720.

In some embodiments of the method, additional instrumentation (not shown) might be utilized to prepare the disc space and endplates, and/or hold the vertebral bodies in a fixed position during distraction, compression, implant insertion, etc.

In some embodiments of the method, the intervertebral implant may be a first intervertebral implant and the method may also include implanting a second intervertebral implant within the intervertebral space 1730 adjacent the first intervertebral implant.

In some embodiments of the method, at least one of a minor diameter of the shaft and a major diameter of the helical thread of the intervertebral implant may be constant along at least a portion of the shaft.

In some embodiments of the method, at least one of a minor diameter of the shaft and a major diameter of the helical thread of the intervertebral implant may vary along at least a portion of the shaft.

However, it will be understood the intervertebral implant may (or may not) include any shape, thread configuration, feature, morphology, etc., that is described or contemplated herein with respect to any fastener/implant.

In some embodiments, the intervertebral implant may include any size, length, diameter, shape, etc., to fit within a given intervertebral space 1730.

In some embodiments, the intervertebral implant may include any angulation (e.g., conical shape, etc.) to provide a desired spinal curvature for a patient.

In some embodiments, the intervertebral implant may be inserted into the intervertebral space 1730 from a posterior direction, an anterior direction, a lateral direction, or any combinations thereof.

Any procedures/methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Any of the fasteners described herein may be configured for removal and replacement during a revision procedure by simply unscrewing and removing the fastener from the bone/tissue in which the fastener resides. Moreover, the fasteners described herein may advantageously be removed from bone without removing any appreciable amount of bone during the removal process to preserve the bone. In this manner, fasteners may be mechanically integrated with the bone, while not being cemented to the bone or integrated via bony ingrowth, in order to provide an instant and removable connection between a fastener and a bone. Accordingly, revision procedures utilizing the fasteners described herein can result in less trauma to the bone and improved patient outcomes.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. Moreover, as defined herein the term "substantially" means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, instruments, and methods disclosed herein.

What is claimed is:

1. A bone disunion instrument system comprising:
    a first bone pin comprising:
        a first proximal end; and
        a first distal end configured to anchor in a first bone portion;
    a second bone pin comprising:
        a second proximal end; and
        a second distal end configured to anchor in a second bone portion, wherein the second bone portion is positioned adjacent the first bone portion and a bone disunion is formed intermediate the first bone portion and the second bone portion; and
    a guide block comprising:
        a first bone pin hole configured to receive the first bone pin therethrough;
        a second bone pin hole configured to receive the second bone pin therethrough; and
        a window formed through the guide block intermediate the first bone pin hole and the second bone pin hole, wherein, when the first bone pin is anchored in the first bone portion and inserted through the first bone pin hole, the second bone pin is anchored in the second bone portion and inserted through the second bone pin hole, and the guide block is slidingly moved along the first bone pin and the second bone pin toward the bone disunion:
            the first bone pin hole imparts a first force on the first bone pin along a first direction to compress or distract the first bone portion with respect to the second bone portion;
            the second bone pin hole imparts a second force on the second bone pin along a second direction to compress or distract the second bone portion with respect to the first bone portion; and
            the window is configured to provide access for an implant placed through the window to couple with at least one of the first bone portion and the second bone portion while the bone disunion is under compression or distraction in order to stabilize the bone disunion.

2. The bone disunion instrument system of claim 1, wherein the guide block comprises at least one of:
    a first inferior lead-in feature formed about the first bone pin hole on an inferior surface of the guide block;
    a second inferior lead-in feature formed about the second bone pin hole on the inferior surface of the guide block;
    a first superior lead-in feature formed about the first bone pin hole on a superior surface of the guide block; and
    a second superior lead-in feature formed about the second bone pin hole on the superior surface of the guide block.

3. The bone disunion instrument system of claim 2, wherein a first longitudinal axis of the first bone pin hole is parallel with a second longitudinal axis of the second bone pin hole.

4. The bone disunion instrument system of claim 3, wherein the first bone pin hole and the second bone pin hole are separated from each other by a first distance to compress the first bone portion and the second bone portion toward each other when the first bone pin is anchored in the first bone portion and inserted through the first bone pin hole, and the second bone pin is anchored in the second bone portion and inserted through the second bone pin hole.

5. The bone disunion instrument system of claim 3, wherein the first bone pin hole and the second bone pin hole are separated from each other by a second distance to distract the first bone portion and the second bone portion away from each other when the first bone pin is anchored in the first bone portion and inserted through the first bone pin hole, and the second bone pin is anchored in the second bone portion and inserted through the second bone pin hole.

6. The bone disunion instrument system of claim 3, wherein the first bone pin hole and the second bone pin hole are separated from each other by a third distance to hold the first bone portion and the second bone portion in a neutral position with respect to each other when the first bone pin is anchored in the first bone portion and inserted through the first bone pin hole, and the second bone pin is anchored in the second bone portion and inserted through the second bone pin hole.

7. The bone disunion instrument system of claim 3, further comprising:
    an insert guide configured to be at least partially received within the window, the insert guide comprising a guide hole formed therethrough; and
    a spade guide comprising:
        a spade portion at a distal end of the spade guide; and
        a pin portion at a proximal end of the spade guide, wherein, when the insert guide is at least partially received within the window, the spade portion is inserted into the bone disunion between the first bone portion and the second bone portion, and the pin portion is inserted through the guide hole:
the first bone pin hole is configured to guide the first bone pin into the first bone portion along a first trajectory defined by an orientation of the pin portion relative to the guide hole; and
the second bone pin hole is configured to guide the second bone pin into the second bone portion along a second trajectory defined by the orientation of the pin portion relative to the guide hole.

8. A bone disunion instrument system comprising:
a first bone pin comprising:
   a first proximal end; and
   a first distal end configured to anchor in a first bone portion;
a second bone pin comprising:
   a second proximal end; and
   a second distal end configured to anchor in a second bone portion, wherein the second bone portion is positioned adjacent the first bone portion and a bone disunion is formed intermediate the first bone portion and the second bone portion;
a spade guide comprising:
   a spade portion at a distal end of the spade guide; and
   a pin portion at a proximal end of the spade guide;
a placement block comprising:
   a first bone pin hole configured to receive the first bone pin therethrough;
   a second bone pin hole configured to receive the second bone pin therethrough; and
   a placement block hole intermediate the first bone pin hole and the second bone pin hole,
   wherein, when the spade portion of the spade guide is inserted into the bone disunion between the first bone portion and the second bone portion, and the pin portion of the spade guide is inserted through the placement block hole:
      the first bone pin hole is configured to guide the first bone pin into the first bone portion along a first trajectory defined by an orientation of the pin portion relative to the placement block hole; and
      the second bone pin hole is configured to guide the second bone pin into the second bone portion along a second trajectory defined by the orientation of the pin portion relative to the placement block hole; and
an implant insertion block comprising:
   a third bone pin hole;
   a fourth bone pin hole; and
   a window formed through the implant insertion block intermediate the third bone pin hole and the fourth bone pin hole,
   wherein, when the first bone pin is anchored in the first bone portion and inserted through the third bone pin hole, and the second bone pin is anchored in the second bone portion and inserted through the fourth bone pin hole:
      the window is configured to provide access for an implant placed through the window to couple with at least one of the first bone portion and the second bone portion and stabilize the bone disunion.

9. The bone disunion instrument system of claim 8, wherein the placement block comprises at least one of:

a first inferior lead-in feature formed about the first bone pin hole on an inferior surface of the placement block;
a second inferior lead-in feature formed about the second bone pin hole on the inferior surface of the placement block;
a first superior lead-in feature formed about the first bone pin hole on a superior surface of the placement block; and
a second superior lead-in feature formed about the second bone pin hole on the superior surface of the placement block.

10. The bone disunion instrument system of claim 9, wherein a first longitudinal axis of the first bone pin hole is parallel with a second longitudinal axis of the second bone pin hole.

11. The bone disunion instrument system of claim 10, wherein:
the spade portion comprises:
   a first substantially flat surface; and
   a second substantially flat surface opposite the first substantially flat surface,
wherein:
   the first substantially flat surface is configured to engage a first surface of the first bone portion within the bone disunion; and
   the second substantially flat surface is configured to engage a second surface of the second bone portion within the bone disunion to indicate an orientation of the bone disunion with the pin portion of the spade guide.

12. The bone disunion instrument system of claim 8, wherein the implant insertion block comprises at least one of:
a first inferior lead-in feature formed about the third bone pin hole on an inferior surface of the implant insertion block;
a second inferior lead-in feature formed about the fourth bone pin hole on the inferior surface of the implant insertion block;
a first superior lead-in feature formed about the third bone pin hole on a superior surface of the implant insertion block; and
a second superior lead-in feature formed about the fourth bone pin hole on the superior surface of the implant insertion block.

13. The bone disunion instrument system of claim 12, wherein the third bone pin hole is parallel with the fourth bone pin hole.

14. The bone disunion instrument system of claim 13, wherein the first bone pin hole and the second bone pin hole are separated from each other by a first distance to compress the first bone portion and the second bone portion toward each other when the first bone pin is anchored in the first bone portion and inserted through the first bone pin hole, and the second bone pin is anchored in the second bone portion and inserted through the second bone pin hole.

15. A bone disunion instrument system comprising:
a first bone pin comprising:
   a first proximal end; and
   a first distal end configured to anchor in a first bone portion;
a second bone pin comprising:
   a second proximal end; and
   a second distal end configured to anchor in a second bone portion, wherein the second bone portion is positioned adjacent the first bone portion and a bone disunion is formed intermediate the first bone portion and the second bone portion; and a guide block comprising:
   a first bone pin hole configured to receive the first bone pin therethrough;
   a second bone pin hole configured to receive the second bone pin therethrough; and
   a window formed through the guide block intermediate the first bone pin hole and the second bone pin hole, wherein the window is larger than the first bone pin hole and the second bone pin hole;
   wherein, when the first bone pin is anchored in the first bone portion and inserted through the first bone pin hole, and the second bone pin is anchored in the second bone portion and inserted through the second bone pin hole:
      the first bone pin hole imparts a first force on the first bone pin along a first direction to compress or distract the first bone portion with respect to the second bone portion;
      the second bone pin hole imparts a second force on the second bone pin along a second direction to compress or distract the second bone portion with respect to the first bone portion; and
      the window is configured to provide access for an implant placed through the window to couple with at least one of the first bone portion and the second bone portion while the bone disunion is under compression or distraction in order to stabilize the bone disunion.

16. The bone disunion instrument system of claim 15, wherein the guide block comprises at least one of:
   a first inferior lead-in feature formed about the first bone pin hole on an inferior surface of the guide block;
   a second inferior lead-in feature formed about the second bone pin hole on the inferior surface of the guide block;
   a first superior lead-in feature formed about the first bone pin hole on a superior surface of the guide block; and
   a second superior lead-in feature formed about the second bone pin hole on the superior surface of the guide block.

17. The bone disunion instrument system of claim 15, wherein a first longitudinal axis of the first bone pin hole is parallel with a second longitudinal axis of the second bone pin hole.

18. The bone disunion instrument system of claim 17, wherein the first bone pin hole and the second bone pin hole are separated from each other by a first distance to compress the first bone portion and the second bone portion toward each other when the first bone pin is anchored in the first bone portion and inserted through the first bone pin hole, and the second bone pin is anchored in the second bone portion and inserted through the second bone pin hole.

19. The bone disunion instrument system of claim 17, wherein the first bone pin hole and the second bone pin hole are separated from each other by a second distance to distract the first bone portion and the second bone portion away from each other when the first bone pin is anchored in the first bone portion and inserted through the first bone pin hole, and the second bone pin is anchored in the second bone portion and inserted through the second bone pin hole.

20. The bone disunion instrument system of claim 17, wherein the first bone pin hole and the second bone pin hole are separated from each other by a third distance to hold the first bone portion and the second bone portion in a neutral position with respect to each other when the first bone pin is anchored in the first bone portion and inserted through the first bone pin hole, and the second bone pin is anchored in the second bone portion and inserted through the second bone pin hole.

21. A bone disunion system comprising:
   a first bone pin comprising:
      a first proximal end; and
      a first distal end configured to anchor in a first bone portion;
   a second bone pin comprising:
      a second proximal end; and
      a second distal end configured to anchor in a second bone portion, wherein the second bone portion is positioned adjacent the first bone portion and a bone disunion is formed intermediate the first bone portion and the second bone portion;
   a guide block comprising:
      a first bone pin hole configured to receive the first bone pin therethrough;
      a second bone pin hole configured to receive the second bone pin therethrough; and
      a window formed through the guide block intermediate the first bone pin hole and the second bone pin hole; and
   an implant configured to be placed through the window of the guide block;
      wherein, when the first bone pin is anchored in the first bone portion and inserted through the first bone pin hole, and the second bone pin is anchored in the second bone portion and inserted through the second bone pin hole:
         the first bone pin hole imparts a first force on the first bone pin along a first direction to compress or distract the first bone portion with respect to the second bone portion;
         the second bone pin hole imparts a second force on the second bone pin along a second direction to compress or distract the second bone portion with respect to the first bone portion; and
         the window is configured to provide access for the implant placed through the window to couple with at least one of the first bone portion and the second bone portion while the bone disunion is under compression or distraction in order to stabilize the bone disunion.

22. The bone disunion system of claim 21, wherein the guide block comprises at least one of:
   a first inferior lead-in feature formed about the first bone pin hole on an inferior surface of the guide block;
   a second inferior lead-in feature formed about the second bone pin hole on the inferior surface of the guide block;
   a first superior lead-in feature formed about the first bone pin hole on a superior surface of the guide block; and
   a second superior lead-in feature formed about the second bone pin hole on the superior surface of the guide block.

23. The bone disunion system of claim 21, wherein a first longitudinal axis of the first bone pin hole is parallel with a second longitudinal axis of the second bone pin hole.

24. The bone disunion system of claim 23, wherein the first bone pin hole and the second bone pin hole are separated from each other by a first distance to compress the first bone portion and the second bone portion toward each other when the first bone pin is anchored in the first bone portion and inserted through the first bone pin hole, and the second bone pin is anchored in the second bone portion and inserted through the second bone pin hole.

25. The bone disunion system of claim 23, wherein the first bone pin hole and the second bone pin hole are separated from each other by a second distance to distract the first bone portion and the second bone portion away from each other when the first bone pin is anchored in the first bone portion and inserted through the first bone pin hole, and the second bone pin is anchored in the second bone portion and inserted through the second bone pin hole.

26. The bone disunion system of claim 23, wherein the first bone pin hole and the second bone pin hole are separated from each other by a third distance to hold the first bone portion and the second bone portion in a neutral position with respect to each other when the first bone pin is anchored in the first bone portion and inserted through the first bone pin hole, and the second bone pin is anchored in the second bone portion and inserted through the second bone pin hole.

* * * * *